United States Patent
Albrecht et al.

(10) Patent No.: US 9,624,244 B2
(45) Date of Patent: Apr. 18, 2017

(54) BENZO [B] ISOXAZOLOAZEPINE BROMODOMAIN INHIBITORS AND USES THEREOF

(71) Applicant: Constellation Pharmaceuticals, Inc., Cambridge, MA (US)

(72) Inventors: Brian K. Albrecht, Cambridge, MA (US); Victor S. Gehling, Somerville, MA (US); Alexander M. Taylor, Cambridge, MA (US); Rishi G. Vaswani, Newton, MA (US)

(73) Assignee: Constellation Pharmaceuticals, Inc., Cambridge, MA (US)

( * ) Notice: Subject to any disclaimer, the term of this patent is extended or adjusted under 35 U.S.C. 154(b) by 46 days.

(21) Appl. No.: 14/405,211

(22) PCT Filed: Jun. 6, 2013

(86) PCT No.: PCT/US2013/044449
§ 371 (c)(1),
(2) Date: Dec. 3, 2014

(87) PCT Pub. No.: WO2013/184878
PCT Pub. Date: Dec. 12, 2013

(65) Prior Publication Data
US 2015/0148333 A1  May 28, 2015

Related U.S. Application Data

(60) Provisional application No. 61/656,280, filed on Jun. 6, 2012.

(51) Int. Cl.
*A61K 31/55* (2006.01)
*C07D 498/04* (2006.01)
*C07D 498/10* (2006.01)

(52) U.S. Cl.
CPC ............ *C07D 498/10* (2013.01); *A61K 31/55* (2013.01); *C07D 498/04* (2013.01)

(58) Field of Classification Search
CPC .............................. A61K 31/55; C07D 498/04
USPC .......................................... 514/215; 540/578
See application file for complete search history.

(56) References Cited

U.S. PATENT DOCUMENTS

| | | | |
|---|---|---|---|
| 3,523,939 A | 8/1970 | Fryer et al. | |
| 3,681,343 A | 8/1972 | Hester, Jr. | |
| 3,709,898 A | 1/1973 | Hester, Jr. | |
| 3,763,144 A | 10/1973 | Hellerback et al. | |
| 3,781,289 A | 12/1973 | Hester, Jr. | |
| 3,850,942 A | 11/1974 | Hester et al. | |
| 3,886,141 A | 5/1975 | Chase | |
| 3,903,103 A | 9/1975 | Hester, Jr. | |
| 3,966,736 A | 6/1976 | Szmuszkovicz | |
| 4,110,455 A | 8/1978 | von Bebenburg et al. | |
| 4,155,904 A | 5/1979 | Schlesinger | |
| 4,327,026 A | 4/1982 | Branca et al. | |
| 4,374,773 A | 2/1983 | Branca et al. | |
| 4,377,522 A | 3/1983 | Branca et al. | |
| 4,455,307 A | 6/1984 | Hester, Jr. | |
| 4,820,834 A | 4/1989 | Evans et al. | |
| 4,959,361 A | 9/1990 | Walser | |
| 4,992,437 A | 2/1991 | Naka et al. | |
| 5,004,741 A | 4/1991 | Evans et al. | |
| 5,175,159 A | 12/1992 | Bock et al. | |
| 5,185,331 A | 2/1993 | Freidinger et al. | |
| 5,185,442 A | 2/1993 | Weber et al. | |
| 5,206,234 A | 4/1993 | Bock et al. | |
| 5,382,579 A | 1/1995 | Okano et al. | |

(Continued)

FOREIGN PATENT DOCUMENTS

| | | | |
|---|---|---|---|
| CA | 2020806 A1 | 1/1991 | |
| CA | 2032222 A1 | 6/1991 | |

(Continued)

OTHER PUBLICATIONS

Proctor, George R., et al., "Azabenzycycloheptones, Part 19, Formation of Some Heterocyclic Annulated Compounds from 1,2,3,4-tetrahydro-1-benzazepine derivatives," Journal of the Chemical Society, Perkin Transactions 1, Chemical Society, Letchworth, GB, Jan. 1, 1978, pp. 862-879.

Venkateswarlu, Peesapati, et al., "Synthesis and Biological Activity of Some New Heterocyclic Annelated Compounds from 2,3,4,5-tetrahydro-1-benzazepines," Indian Journal of Chemistry: IJC, Council of Scientific and Industrial Research, IN., vol. 35B, Dec. 1, 1996, pp. 1287-1293.

Grey, R., et al., "Structure-Based Design of 3-Aryl-6-Amino-Triazolo[4,3-b] Pyridazine Inhibitors of Pim-1 Kinase," Bioorg. Med, Chem, Lett., vol. 19, No. 11, Jun. 1, 2009, pp. 3019-3022.

(Continued)

*Primary Examiner* — Brenda Coleman
(74) *Attorney, Agent, or Firm* — McCarter & English, LLP; Steven G. Davis; Michael J. DeGrazia

(57) ABSTRACT

The present invention relates to compounds useful as inhibitors of bromodomain-containing proteins. The invention also provides pharmaceutically acceptable compositions comprising compounds of the present invention and methods of using said compositions in the treatment of various disorders.

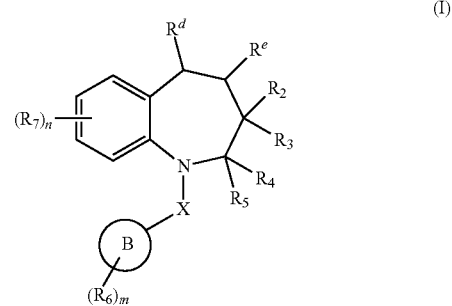

6 Claims, No Drawings

(56) References Cited

U.S. PATENT DOCUMENTS

| | | |
|---|---|---|
| 5,409,909 A | 4/1995 | Okano et al. |
| 5,428,004 A | 6/1995 | Earley et al. |
| 5,439,905 A | 8/1995 | Naka et al. |
| 5,550,126 A | 8/1996 | Horwell et al. |
| 5,593,988 A | 1/1997 | Tahara et al. |
| 5,681,833 A | 10/1997 | Pineiro et al. |
| 5,683,998 A | 11/1997 | Shibayama et al. |
| 5,698,552 A | 12/1997 | Weber et al. |
| 5,712,274 A | 1/1998 | Sueoka et al. |
| 5,721,231 A | 2/1998 | Moriwaki et al. |
| 5,733,905 A | 3/1998 | Albright et al. |
| 5,739,129 A | 4/1998 | Aquino et al. |
| 5,753,647 A | 5/1998 | Weber et al. |
| 5,753,649 A | 5/1998 | Tahara et al. |
| 5,760,031 A * | 6/1998 | Albright ............... C07D 221/12 514/215 |
| 5,795,887 A | 8/1998 | Aquino et al. |
| 5,840,895 A | 11/1998 | Ohtsuka et al. |
| 5,843,941 A | 12/1998 | Marsters, Jr. et al. |
| 5,869,483 A | 2/1999 | Albright et al. |
| 5,929,069 A | 7/1999 | Shudo |
| 6,121,256 A | 9/2000 | Shudo |
| 6,433,167 B1 | 8/2002 | Fujita et al. |
| 6,458,782 B1 | 10/2002 | Kagechika et al. |
| 6,476,017 B2 | 11/2002 | Shudo |
| 6,649,366 B2 | 11/2003 | Chubinskaya et al. |
| 6,777,408 B1 | 8/2004 | Liberatore et al. |
| 7,015,213 B1 | 3/2006 | Bigg et al. |
| 7,160,880 B1 | 1/2007 | Feldman et al. |
| 7,250,410 B2 | 7/2007 | Bourguignon et al. |
| 7,435,730 B2 | 10/2008 | Feldman et al. |
| 7,442,795 B2 | 10/2008 | Bryans et al. |
| 7,473,689 B2 | 1/2009 | Feldman et al. |
| 7,482,337 B2 | 1/2009 | Himmelsbach et al. |
| 7,485,635 B2 | 2/2009 | Feldman et al. |
| 7,528,127 B2 | 5/2009 | Feldman et al. |
| 7,696,212 B2 | 4/2010 | Himmelsbach et al. |
| 8,796,261 B2 | 8/2014 | Albrecht et al. |
| 9,249,161 B2 | 2/2016 | Albrecht et al. |
| 2001/0039272 A1 | 11/2001 | Shudo |
| 2002/0052358 A1 | 5/2002 | Chubinskaya et al. |
| 2004/0053919 A1 | 3/2004 | Chubinskaya et al. |
| 2004/0138214 A1 | 7/2004 | Himmelsbach et al. |
| 2004/0152888 A1 | 8/2004 | Bourguignon et al. |
| 2006/0128695 A1 | 6/2006 | Bourguignon et al. |
| 2007/0093475 A1 | 4/2007 | Feldman et al. |
| 2007/0105844 A1 | 5/2007 | Glick et al. |
| 2007/0135419 A1 | 6/2007 | Feldman et al. |
| 2007/0135420 A1 | 6/2007 | Feldman et al. |
| 2007/0135421 A1 | 6/2007 | Feldman et al. |
| 2009/0093457 A1 | 4/2009 | Himmelsbach et al. |
| 2010/0041643 A1 | 2/2010 | Adachi et al. |
| 2010/0144703 A1 | 6/2010 | Himmelsbach et al. |
| 2010/0256123 A1 | 10/2010 | Sakuma et al. |
| 2010/0286127 A1 | 11/2010 | Miyoshi et al. |
| 2010/0331316 A1 | 12/2010 | Paoletti et al. |
| 2011/0230460 A1 | 9/2011 | Kempen et al. |
| 2014/0135316 A1 | 5/2014 | Albrecht et al. |
| 2014/0371206 A1 | 12/2014 | Albrecht et al. |
| 2015/0148337 A1 | 5/2015 | Albrecht et al. |

FOREIGN PATENT DOCUMENTS

| | | |
|---|---|---|
| CA | 2032427 A1 | 6/1991 |
| CA | 2050268 A1 | 3/1992 |
| CA | 2056809 A1 | 6/1992 |
| CA | 2059353 A1 | 7/1992 |
| CA | 2062456 A1 | 9/1992 |
| CA | 2071092 A1 | 12/1992 |
| CA | 1327570 C | 3/1994 |
| CA | 02258053 A1 | 12/1997 |
| DE | 2640599 A1 | 3/1978 |
| DE | 3936828 A1 | 5/1990 |
| DE | 4006471 A1 | 9/1990 |
| DE | 4027470 A1 | 3/1992 |
| DE | 4107521 A1 | 9/1992 |
| DE | 4128581 A1 | 3/1993 |
| DE | 4219659 A1 | 12/1993 |
| EP | 0169392 A2 | 1/1986 |
| EP | 0315698 A1 | 5/1989 |
| EP | 0328924 A2 | 8/1989 |
| EP | 0342587 A2 | 11/1989 |
| EP | 0348523 A1 | 1/1990 |
| EP | 0367110 A1 | 5/1990 |
| EP | 0407955 A1 | 1/1991 |
| EP | 0480455 A1 | 4/1992 |
| EP | 495473 A1 | 7/1992 |
| EP | 0514125 A1 | 11/1992 |
| EP | 0559891 A1 | 9/1993 |
| EP | 0656361 A4 | 1/1995 |
| EP | 636625 A2 | 2/1995 |
| EP | 0661284 A4 | 5/1995 |
| EP | 0692483 A4 | 11/1995 |
| EP | 0989131 A1 | 3/2000 |
| EP | 1297836 A1 | 4/2003 |
| EP | 1887008 A1 | 2/2008 |
| EP | 2239264 A1 | 10/2010 |
| FR | 2154511 A1 | 5/1973 |
| FR | 2220257 A1 | 10/1974 |
| GB | 1409693 A | 10/1975 |
| GB | 2259013 A | 3/1993 |
| JP | 7179471 | 7/1995 |
| JP | 11228576 | 8/1999 |
| JP | 2959591 B2 | 10/1999 |
| JP | 3223290 B2 | 10/2001 |
| JP | 03264588 B2 | 3/2002 |
| JP | 03264589 B2 | 3/2002 |
| JP | 04226993 B2 | 2/2009 |
| WO | 9303717 A1 | 3/1993 |
| WO | 9307129 A1 | 4/1993 |
| WO | 9312791 A1 | 7/1993 |
| WO | 9313776 A1 | 7/1993 |
| WO | 9319052 A1 | 9/1993 |
| WO | 9406801 A1 | 3/1994 |
| WO | 9426723 A2 | 11/1994 |
| WO | 9514694 A1 | 6/1995 |
| WO | 9528399 A1 | 10/1995 |
| WO | 9711061 A1 | 3/1997 |
| WO | 9747622 A1 | 12/1997 |
| WO | 9811111 A1 | 3/1998 |
| WO | 9828268 A2 | 7/1998 |
| WO | 9858930 A1 | 12/1998 |
| WO | 9929324 A1 | 6/1999 |
| WO | 0006157 A1 | 2/2000 |
| WO | 0012547 A2 | 3/2000 |
| WO | 0054778 A1 | 9/2000 |
| WO | 0069836 A1 | 11/2000 |
| WO | 0147510 A2 | 7/2001 |
| WO | 02098865 A2 | 12/2002 |
| WO | 03/074525 A1 | 9/2003 |
| WO | 2004041258 A2 | 5/2004 |
| WO | 2004041820 A1 | 5/2004 |
| WO | 2004/058769 A2 | 7/2004 |
| WO | 2005/002590 A1 | 1/2005 |
| WO | 2005099759 A1 | 10/2005 |
| WO | 2006052360 A1 | 4/2006 |
| WO | 2006129623 A1 | 12/2006 |
| WO | 2007016087 A2 | 2/2007 |
| WO | 2007050587 A2 | 5/2007 |
| WO | 2007/079820 A1 | 7/2007 |
| WO | 2008023847 A1 | 2/2008 |
| WO | 2008109856 A2 | 9/2008 |
| WO | 2009059191 A1 | 5/2009 |
| WO | 2009081349 A1 | 7/2009 |
| WO | 2009152589 A1 | 12/2009 |
| WO | 2010008459 A1 | 1/2010 |
| WO | 2010049466 A1 | 5/2010 |
| WO | 2010121164 A2 | 10/2010 |
| WO | 2010128685 A1 | 11/2010 |
| WO | 2011037128 A1 | 3/2011 |
| WO | 2011054553 A1 | 5/2011 |
| WO | 2011054841 A1 | 5/2011 |
| WO | 2011054843 A1 | 5/2011 |

(56) References Cited

FOREIGN PATENT DOCUMENTS

| WO | 2011054844 A1 | 5/2011 |
|---|---|---|
| WO | 2011054845 A1 | 5/2011 |
| WO | 2011054846 A1 | 5/2011 |
| WO | 2011054848 A1 | 5/2011 |
| WO | 2011054851 A1 | 5/2011 |
| WO | 2011079315 A1 | 6/2011 |
| WO | 2011/123678 A2 | 10/2011 |
| WO | 2011143651 A1 | 11/2011 |
| WO | 2011143657 A1 | 11/2011 |
| WO | 2011143660 A2 | 11/2011 |
| WO | 2011143669 A2 | 11/2011 |
| WO | 2011/161031 A1 | 12/2011 |
| WO | 2012/075383 A2 | 6/2012 |
| WO | 2013024104 A1 | 2/2013 |
| WO | 2013030150 A1 | 3/2013 |
| WO | 2013033268 A2 | 3/2013 |
| WO | 2013033269 A1 | 3/2013 |
| WO | 2013033270 A2 | 3/2013 |
| WO | 2013033420 A1 | 3/2013 |

OTHER PUBLICATIONS

Filippakopoulos, et al., "Selective Inhibition of BET Bromodomains," Nature, Dec. 30, 2010, vol. 468, pp. 1067-1073.

Kosychova, L., et al., "Synthesis of Substitute 5,6-Dihydro-4H-[1,2,4]Triazolo[4,3-a][1,5]Benzodiazepines," Chemistry of Heterocyclic Compounds, vol. 40, No. 6, Jun. 2004, pp. 811-815.

Gussio, Rick, et al., "All-Atom Models for the Non-Nucleoside Binding Site of HIV-1 Reverse Transcriptase Complexed with Inhibitors: A 3D QSAR Approach," J. Med. Chem., Apr. 12, 1996, vol. 39, No. 8, pp. 1645-1650.

International Search Report and Written Opinion, dated Jul. 23, 2013, Int'l Appl'n No. PCT/US2013/044449, Int'l Filing Date Jun. 6, 2013.

International Search Report and Written Opinion, dated Feb. 21, 2013, Int'l Appl'n No. PCT/US2012/042825, Int'l Filing Date Jun. 15, 2012.

International Preliminary Report on Patentability, dated Nov. 5, 2013, Int'l Appl'n No. PCT/US2012/036569, Int'l Filing Date May 4, 2012.

International Search Report and Written Opinion, dated Jul. 23, 2013, Int'l Appl'n No. PCT/US2013/044444, Int'l Filing Date Jun. 6, 2013.

International Search Report and Written Opinion, dated Apr. 17, 2012, Int'l Appl'n No. PCT/US2011/063173, Int'l Filing Date Dec. 2, 2011.

International Preliminary Report on Patentability, mailed Jan. 3, 2014, International Application No. PCT/US2012/042825; International Filing Date: Jun. 15, 2012, 10 pages.

Terrett, N.K., et al., "Imidazoú2',3',:6,5 3/4 Dipyridoú3,2-B:2',3'-E 3/4-1,4-Diazepines: Non- Nucleoside HIV-1 Reverse Transcriptase Inhibitors with Greater Enzyme Affinity than Nevirapine," Bioorganic & Medicinal Chemistry Letters, vol. 12, No. 2, Dec. 1, 1992, pp. 1745-1750, XP002912883.

Kosychova, et al., "Synthesis of New [1,2,4]triazolo[4,3-a][1,5]benzodiaze—pine derivatives," Lietuvos Mokslu Akademija. Chemija, vol. 22, No. 1, Jan. 1, 2011, pp. 60-64, XP055136653.

Kosychova, et al., "Synthesis of novel 5,6-dihydro-4H-[1,2,4]triazolo[4,3-a][1,5]benzodiazepines," Rigas Tehniskas Universitates Zinatniskie Raksti. Serija 1: Materialzinatne Un Lietiska Kimija, vol. 22, Jan. 1, 2010, pp. 94-99, XP009179817.

Di Bracco, M., et al., "1,5-Benzodiazepines. Part XII. Synthesis and Biological Evaluations of Tricyclic and Tetracyclic 1,5-benzodiazepine Derivatives as Nevirapine Analogues," European Journal of Medicinal Chemistry, vol. 36, No. 11-12, Dec. 1, 2001, pp. 935-949, XP027205317.

Jiban K. Chakrabarti, et al., "Chemistry of Adamantane. Part XI. 1,2-Disubstituted Adamantanes. Synthesis and Reactions of Adamantano[2,1- b ]- and protoadamantano-[4,5- b ] [1,5] benzodiazepines," Journal of Heterocyclic Chemistry, vol. 15, No. 5, Aug. 1, 1978, pp. 705-710, XP055136791.

Szarvasi, E., et al., "(4H)Dihydro-5,6(s)-triazolo-(4,3-a)benzodiazepines-1,5 a activite analgesique et anti-inflammatoire," European Journal of Medicinal Chemistry, vol. 13, No. 2, Mar. 1, 1978, pp. 113-119, XP009179828.

* cited by examiner

BENZO [B] ISOXAZOLOAZEPINE BROMODOMAIN INHIBITORS AND USES THEREOF

RELATED APPLICATIONS

This application is a 35 U.S.C. §371 national stage filing of International Application No. PCT/US2013/044449, filed Jun. 6, 2013, which claims the benefit of U.S. Provisional Application No. 61/656,280, filed Jun. 6, 2012. The entire teachings of the above applications are incorporated herein by reference.

TECHNICAL FIELD OF THE INVENTION

The present invention relates to compounds useful as inhibitors of one or more bromodomain-containing proteins.

BACKGROUND OF THE INVENTION

Packaging the 3 billion nucleotides of the human genome into the nucleus of a cell requires tremendous compaction. To accomplish this feat, DNA in our chromosomes is wrapped around spools of proteins called histones to form dense repeating protein/DNA polymers known as chromatin: the defining template for gene regulation. Far from serving as mere packaging modules, chromatin templates form the basis of a newly appreciated and fundamentally important set of gene control mechanisms termed epigenetic regulation. By conferring a wide range of specific chemical modifications to histones and DNA, epigenetic regulators modulate the structure, function, and accessibility of our genome, thereby exerting a tremendous impact on gene expression. Hundreds of epigenetic effectors have recently been identified, many of which are chromatin-binding proteins or chromatin-modifying enzymes. Significantly, an increasing number of these proteins have been associated with a variety of disorders such as neurodegenerative disorders, metabolic diseases, inflammation, and cancer. Thus, highly selective therapeutic agents directed against this emerging class of gene regulatory proteins promise new approaches to the treatment of human diseases.

SUMMARY OF THE INVENTION

It has now been found that compounds described herein, and pharmaceutically acceptable compositions thereof, are effective as inhibitors of one or more bromodomain-containing proteins. Such compounds include those of Formula (I):

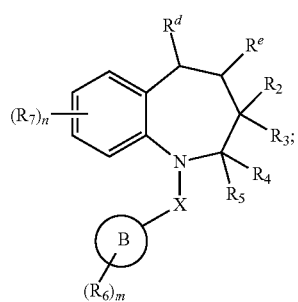

(I)

or a pharmaceutically acceptable salt thereof, wherein each of $R^d$, $R^e$, $R_1$, $R_2$, $R_3$, $R_4$, $R_5$, X, $R_6$, m, $R_7$, and n are as defined and described herein.

The provided compounds, and pharmaceutically acceptable compositions thereof, are useful for treating a variety of diseases, disorders or conditions associated with abnormal cellular responses triggered by events mediated by bromodomain-containing proteins. Such diseases, disorders, or conditions include those described herein.

The provided compounds are also useful for the study of bromodomain-containing proteins in biological and pathological phenomena, the study of intracellular signal transduction pathways mediated by bromodomain-containing proteins, and the comparative evaluation of new inhibitors of bromodomain-containing proteins.

DETAILED DESCRIPTION OF CERTAIN EMBODIMENTS

1. General Description of Compounds of the Invention

In certain embodiments, the present invention provides a compound of Formula (I):

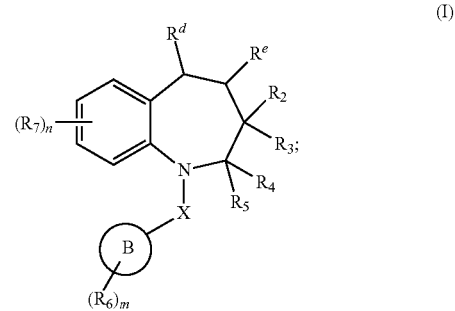

(I)

or a pharmaceutically acceptable salt thereof, wherein:

Ring B is absent; or a 3-7 membered saturated or partially unsaturated carbocyclic ring, phenyl, an 8-10 membered bicyclic saturated, partially unsaturated, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$R^d$ and $R^e$ taking together with their intervening atoms form an isoxazolyl optionally substituted with $R_1$;

$R_1$ is hydrogen or $C_{1-6}$ aliphatic;

$R_2$-$R_5$ are each independently hydrogen, halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, —OC(O)N(R')$_2$, or —(CH$_2$)$_p$R$^x$;

each of $R_2$ and $R_3$, $R_2$ and $R_4$, $R_3$ and $R_5$, or $R_4$ and $R_5$ are taken together with their intervening atoms to form CO, or an optionally substituted 3-7 membered saturated or partially unsaturated spiro-fused ring having 0-2 heteroatoms independently selected from nitrogen, oxygen, and sulfur; and X is hydrogen, $SO_2$, CO, a covalent bond, or an optionally substituted bivalent $C_{1-6}$ hydrocarbon chain wherein one methylene unit is optionally replaced by —NR'—, —N(R')C(O)—, —C(O)N(R')—, —N(R')SO$_2$—, —SO$_2$N(R')—, —O—, —C(O)—, —OC(O)—, —C(O)O—, —S—, —SO— or —SO$_2$—; or When ring B is absent, X is hydrogen or substituted $C_{1-6}$ aliphatic; and $R^x$ is halogen, optionally substituted $C_{1-6}$ aliphatic, —OR, —SR, —CN, —N(R')$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$;

each R is independently hydrogen or an optionally substituted group selected from $C_{1-6}$ aliphatic, phenyl, a 3-7 membered saturated or partially unsaturated carbocyclic ring, a 7-10 membered bicyclic saturated, partially unsaturated, or aryl ring, a 5-6 membered monocyclic heteroaryl ring having 1-3 heteroatoms independently selected from nitrogen, oxygen, and sulfur, a 4-7 membered saturated or partially unsaturated heterocyclic ring having 1-2 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, and a 8-10 membered bicyclic heteroaryl ring having 1-4 heteroatoms independently selected from nitrogen, oxygen, and sulfur;

each R' is independently —R, —C(O)R, —C(S)R, —CO$_2$R, —C(O)N(R)$_2$, —C(S)N(R)$_2$, —S(O)R, —SO$_2$R, or —SO$_2$N(R)$_2$; or two R' on the same nitrogen are taken together with their intervening atoms to form an optionally substituted group selected from a 4-7 membered monocyclic saturated or partially unsaturated ring having 1-2 heteroatoms independently selected from nitrogen, oxygen, and sulfur, and a 7-12 membered bicyclic saturated, partially unsaturated, or aromatic fused ring having 1-3 heteroatoms independently selected from nitrogen, oxygen, and sulfur;

each of m and n is independently 0-4, as valency permits; and each of $R_6$ and $R_7$ are independently —R, halogen, ($C_1$-$C_6$)alkyl, halogen, ($C_1$-$C_6$)haloalkyl, ($C_1$-$C_6$)alkoxy, ($C_1$-$C_6$)haloalkoxy, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$.

2. Compounds and Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987; the entire contents of each of which are incorporated herein by reference.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Optionally, the present structures include the replacement of one or more hydrogen atoms by deuterium. Alternatively, hydrogen is present at natural abundance at all positions. Such compounds are useful, for example, as analytical tools, as probes in biological assays, or as therapeutic agents in accordance with the present invention.

Where a particular enantiomer is preferred, it may, in some embodiments be provided substantially free of the corresponding enantiomer, and may also be referred to as "optically enriched." "Optically enriched," as used herein, means that the compound is made up of a significantly greater proportion of one enantiomer. In certain embodiments the compound is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen, et al., *Tetrahedron* 33:2725 (1977); Eliel, E. L. *Stereochemistry of Carbon Compounds* (McGraw-Hill, N.Y., 1962); Wilen, S. H. *Tables of Resolving Agents and Optical Resolutions* p. 268 (E. L. Eliel, Ed., Univ. of Notre Dame Press, Notre Dame, Ind. 1972).

As used herein, natural abundance refers to the abundance of isotopes of a chemical element as naturally found where the relative atomic mass (a weighted average) of these isotopes is the atomic weight listed for the element in the periodic table.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The terms "halo" and "halogen" as used herein refer to an atom selected from fluorine (fluoro, —F), chlorine (chloro, —Cl), bromine (bromo, —Br), and iodine (iodo, —I).

The term "alkyl," as used herein, refers to a monovalent saturated, straight- or branched-chain hydrocarbon radical derived from an aliphatic moiety containing between one and six carbon atoms by removal of a single hydrogen atom. In some embodiments, alkyl contains 1-5 carbon atoms. In another embodiment, alkyl contains 1-4 carbon atoms. In still other embodiments, alkyl contains 1-3 carbon atoms. In yet another embodiment, alkyl contains 1-2 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like.

The term "alkenyl," as used herein, denotes a monovalent group derived from a straight- or branched-chain aliphatic moiety having at least one carbon-carbon double bond by the removal of a single hydrogen atom. In certain embodiments, alkenyl contains 2-6 carbon atoms. In certain embodiments, alkenyl contains 2-5 carbon atoms. In some embodiments, alkenyl contains 2-4 carbon atoms. In another embodiment, alkenyl contains 2-3 carbon atoms. Alkenyl groups include, for example, ethenyl ("vinyl"), propenyl ("allyl"), butenyl, 1-methyl-2-buten-1-yl, and the like.

The term "alkynyl," as used herein, refers to a monovalent group derived from a straight- or branched-chain aliphatic moiety having at least one carbon-carbon triple bond by the removal of a single hydrogen atom. In certain embodiments, alkynyl contains 2-6 carbon atoms. In certain embodiments, alkynyl contains 2-5 carbon atoms. In some embodiments, alkynyl contains 2-4 carbon atoms. In another embodiment, alkynyl contains 2-3 carbon atoms. Representative alkynyl groups include, but are not limited to, ethynyl, 2-propynyl ("propargyl"), 1-propynyl, and the like.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-6 carbon atoms. In some embodiments, aliphatic groups contain 1-4 carbon atoms, and in yet other embodiments aliphatic groups contain 1-3 carbon atoms. Aliphatic groups include, but are not limited to, alkyl, alkenyl, alkynyl, carbocycle. Suitable aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "unsaturated", as used herein, means that a moiety has one or more units of unsaturation.

The terms "cycloaliphatic", "carbocycle", "carbocyclyl", "carbocyclo", or "carbocyclic", used alone or as part of a larger moiety, refer to a saturated or partially unsaturated cyclic aliphatic monocyclic or bicyclic ring systems, as described herein, having from 3 to 18 carbon ring atoms, wherein the aliphatic ring system is optionally substituted as defined above and described herein. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic", "carbocycle", "carbocyclyl", "carbocyclo", or "carbocyclic" also include aliphatic rings that are fused to one or more aromatic or nonaromatic rings, such as decahydronaphthyl, tetrahydronaphthyl, decalin, or bicyclo[2.2.2]octane, where the radical or point of attachment is on an aliphatic ring.

As used herein, the term "partially unsaturated" refers to a ring moiety that includes at least one double or triple bond between ring atoms but is not aromatic. The term "partially unsaturated" is intended to encompass rings having multiple sites of unsaturation, but is not intended to include aryl or heteroaryl moieties, as herein defined.

The term "aryl" used alone or as part of a larger moiety as in "aralkyl", "aralkoxy", or "aryloxyalkyl", refers to monocyclic, bicyclic, and carbocyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl (abbreviated as "Ph"), biphenyl, naphthyl, anthracyl and the like, which may bear one or more substituents. Also included within the scope of the term "aryl", as it is used herein, is a group in which an aromatic ring is fused to one or more non-aromatic rings, such as indanyl, phthalimidyl, naphthimidyl, phenantriidinyl, or tetrahydronaphthyl, and the like.

The terms "heteroaryl" and "heteroar-", used alone or as part of a larger moiety, e.g., "heteroaralkyl", or "heteroaralkoxy", refer to groups having 5 to 10 ring atoms, preferably 5, 6, 8, or 9 ring atoms; and from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloalkyl, heteroaryl, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloalkyl rings, such as indolinyl, 3H-indolyl, chromanyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently, e.g., halogen; —(CH$_2$)$_{0-4}$R°; —(CH$_2$)$_{0-4}$OR°; —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH═CHPh, which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{04}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched) alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$alkyl, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below. Alternatively, R° is independently hydrogen, C$_{1-6}$alkyl, —CH$_2$Ph, and, —O(CH$_2$)$_{0-1}$Ph wherein Ph (phenyl) is optionally substituted with halogen, (C$_1$-C$_6$)alkoxy, (C$_1$-C$_6$)haloalkoxy, (CpC$_6$)alkyl, (C$_1$-C$_6$)haloalkyl, —CN, —NO$_2$, —NH$_2$, or, —OH.

Suitable monovalent substituents on R° (or the ring formed by taking two independent occurrences of R° together with their intervening atoms), are, e.g., independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$alkyl, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include, e.g., the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$alkyl which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$alkyl which may be substituted as defined below, or an unsubstituted 5-6-membered saturated, partially unsaturated, or aryl ring having 0-4 heteroatoms independently selected from nitrogen, oxygen, or sulfur. Alternatively, R* is hydrogen, C$_{1-6}$alkyl, —CH$_2$Ph, and, —O(CH$_2$)$_{0-1}$Ph wherein Ph (phenyl) is optionally substituted with halogen, (C$_1$-C$_6$)alkoxy, (C$_1$-C$_6$)haloalkoxy, (C$_1$-C$_6$)alkyl, (C$_1$-C$_6$)haloalkyl, —CN, —NO$_2$, —NH$_2$, or, —OH.

Suitable substituents on the alkyl group of R* include, e.g., halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently C$_{1-4}$alkyl, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include, e.g., —R$^\dagger$, —NR$^\dagger$$_2$, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, $C_{1-6}$alkyl which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the alkyl group of R† are independently, e.g., halogen, —R•, -(haloR•), —OH, —OR•, —O(haloR•), —CN, —C(O)OH, —C(O)OR•, —NH₂, —NHR•, —NR•₂, or —NO₂, wherein each R• is unsubstituted or where preceded by "halo" is substituted only with one or more halogens, and is independently $C_{1-4}$alkyl, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "inhibitor" is defined as a compound that binds to and/or inhibits the target bromodomain-containing protein (such as a BET protein, e.g., BRD2, BRD3, BRD4, and/or BRDT) with measurable affinity. In certain embodiments, an inhibitor has an $IC_{50}$ and/or binding constant of less about 50 μM, less than about 1 μM, less than about 500 nM, less than about 100 nM, or less than about 10 nM.

The terms "measurable affinity" and "measurably inhibit," as used herein, means a measurable change in activity of at least one bromodomain-containing protein between a sample comprising a provided compound, or composition thereof, and at least one histone methyltransferase, and an equivalent sample comprising at least one bromodomain-containing protein, in the absence of said compound, or composition thereof.

3. Description of Exemplary Compounds

In a first embodiment, the present invention provides a compound of Formula (I),

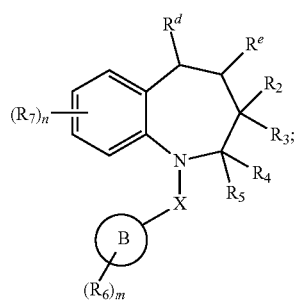

(I)

or a pharmaceutically acceptable salt thereof, wherein the variables are as described above.

In a second embodiment, the compound of Formula (I) is of Formula (Ia) or (Ib):

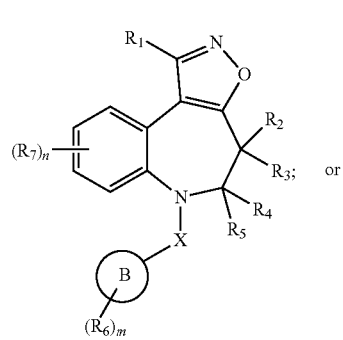

(Ia)

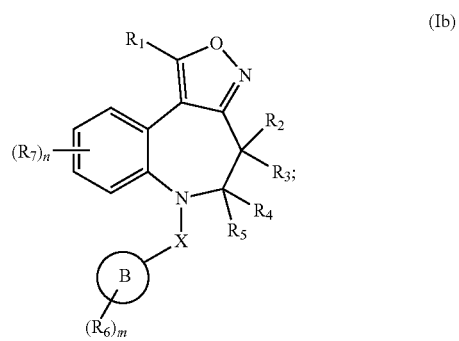

(Ib)

or a pharmaceutically acceptable salt thereof, wherein the variables in structural Formulae (Ia) and (Ib) are as described in the first embodiment.

In a third embodiment, the compound of Formula (I) is of Formula (II) or (III):

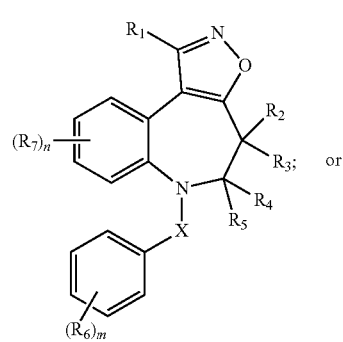

(II)

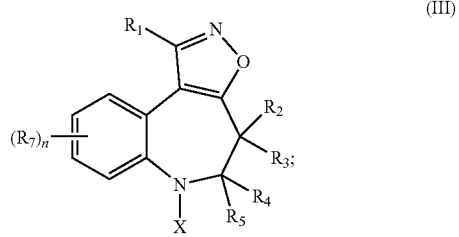

(III)

or a pharmaceutically acceptable salt thereof, wherein the variables in structural Formulae (II) and (III) are as described in the first and second embodiment.

In a fourth embodiment, the compound of Formula (I) is of Formula (IV) or (V):

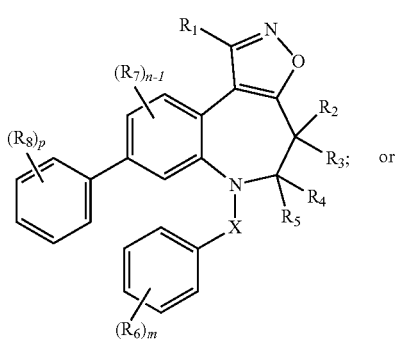

(IV)

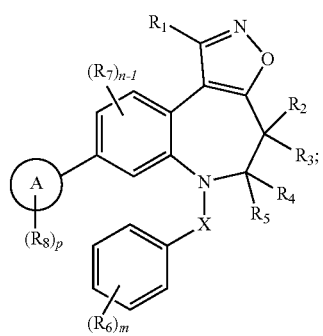

(V)

or a pharmaceutically acceptable salt thereof, wherein

Ring A is a 5-6 membered monocyclic heteroaryl ring or a monocyclic partially saturated heterocyclic ring, each of which having one to three heteroatoms independently selected from nitrogen and oxygen;

each of p, m, and n are independently 0-2 as valency permits;

$R_8$ is independently optionally substituted phenyl, halogen, $(C_1-C_3)$alkyl, halogen, $(C_1-C_3)$haloalkyl, $(C_1-C_3)$alkoxy, $(C_1-C_3)$haloalkoxy, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$; and b is 0-3, wherein the remaining variables of structural Formulae (IV) and (V) are as described in the first, second, and third embodiment.

In a fifth embodiment, compounds having the formulae described above are of Formula (II):

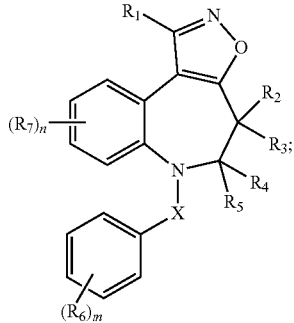

(II)

or a pharmaceutically acceptable salt thereof, wherein $R_7$ is optionally substituted phenyl, halogen, $(C_1-C_3)$alkyl, halogen, $(C_1-C_3)$haloalkyl, $(C_1-C_3)$alkoxy, $(C_1-C_3)$haloalkoxy, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$, wherein the remaining variables of structural Formulae (II) are as described in the first, second, third, and fourth embodiment.

In a sixth embodiment, compounds having the formulae described above are of Formula (VIII), (IX), or (X):

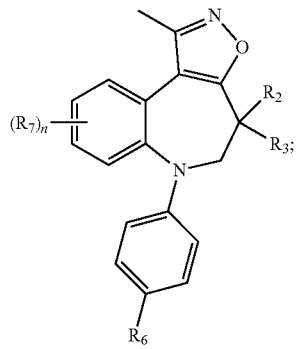

(VIII)

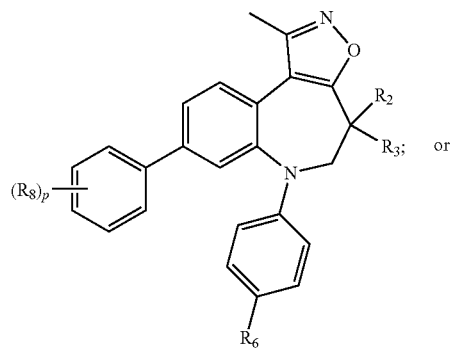

(IX)

or

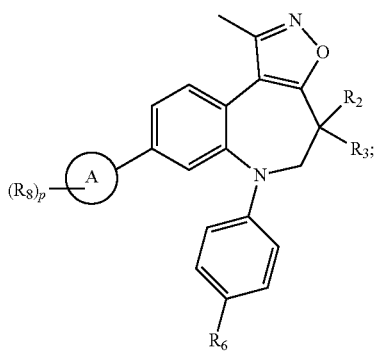

(X)

or a pharmaceutically acceptable salt thereof, wherein the variables are as described in the first, second, third, fourth, and fifth embodiment.

Alternatively, Ring A in structural Formulae (I)-(X) is pyridinyl, pyrazolyl, isoxazolyl, pyridinonyl, or pyrazinyl, wherein the remainder of the variables are as described in the first, second, third, fourth, fifth, and sixth embodiment.

In a seventh embodiment of compounds of the formulae (I)-(X), $R_2$ and $R_4$, if present, are each independently hydrogen, $(C_1-C_6)$alkyl, $(C_1-C_6)$haloalkyl, $(C_1-C_6)$alkoxy, $(C_1-C_6)$haloalkoxy, —N(R')$_2$, —CO, halogen, —CN, —SR, —OH, or —(CH$_2$)$_b$R$^x$;

$R_3$ and $R_5$, if present, are each independently hydrogen or $(C_1-C_6)$alkyl; or each of $R_2$ and $R_3$ or $R_4$ and $R_5$ are taken together with their intervening atoms to form an optionally substituted 3-7 membered cycloalkyl; and X is CO, a covalent bond, or $(C_1-C_3)$alkyl;

each of $R_6$ and $R_7$ are independently optionally substituted phenyl, halogen, $(C_1-C_3)$alkyl, halogen, $(C_1-C_3)$haloalkyl, $(C_1-C_3)$alkoxy, $(C_1-C_3)$haloalkoxy, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$;

each R and R' are independently hydrogen, $(C_1-C_3)$alkyl, halogen, $(C_1-C_3)$haloalkyl, $(C_1-C_3)$alkoxy, $(C_1-C_3)$haloalkoxy, or phenyl optionally substituted with one or more halogen, $(C_1-C_6)$alkyl, $(C_1-C_6)$haloalkyl, $(C_1-C_6)$alkoxy, $(C_1-C_6)$haloalkoxy, —CN, —C(O)R, or —CO$_2$R; and $R^x$ is halogen, $(C_1-C_6)$alkoxy, $(C_1-C_6)$haloalkoxy, —OR, —SR, —CN, —N(R')$_2$, —C(O)R, —CO$_2$R, —C(O)N(R')$_2$, —C(O)C(O)R, —C(O)CH$_2$C(O)R, —N(R')C(O)R, —N(R')C(O)N(R')$_2$, —OC(O)R, or —OC(O)N(R')$_2$; and the remaining variables are as described in the first, second, third, fourth, fifth, and sixth embodiment.

In an eighth embodiment of compounds of the formulae (I)-(X), $R_2$ and $R_4$, if present, are each independently hydrogen, $(C_1-C_3)$alkyl, —N(R')$_2$, —CO, or —(CH$_2$)R'$_2$, (CH$_2$)OH, (CH$_2$)CN, (CH$_2$)CON(R')$_2$, or (CH$_2$)COR';

$R_3$ and $R_5$, if present, are each hydrogen; or $R_2$ and $R_3$ taken together with their intervening atoms to form a 3-7 membered cycloalkyl;

$R_6$ is halogen, —CN, $(C_1-C_6)$alkyl, —C(O)N(R')$_2$, or —SO$_2$R;

$R_7$ is $(C_1-C_3)$alkyl, halogen, $(C_1-C_3)$haloalkyl, $(C_1-C_3)$alkoxy, $(C_1-C_3)$haloalkoxy —C(O)N(R')$_2$, or —CN;

$R_8$ is $(C_1-C_3)$alkyl, halogen, $(C_1-C_3)$haloalkyl, $(C_1-C_3)$alkoxy, $(C_1-C_3)$haloalkoxy, —CN, —(CH$_2$)NH$_2$, (CH$_2$)OH, (CH$_2$)CN, (CH$_2$)CON(Me)$_2$, or (CH$_2$)CONH$_2$; and each R and R' are independently hydrogen or $(C_1-C_3)$alkyl; and the remaining variables are as described in the first, second, third, fourth, fifth, sixth, and seventh embodiment.

In a ninth embodiment of compounds of the formulae (I)-(X), $R_1$ is methyl;

$R_2$ is hydrogen, —NH$_2$, $(C_1-C_3)$alkyl, —(CH$_2$)$_2$OH, —CH$_2$C(O)NH$_2$, —CH$_2$C(O)N(Me)$_2$, or —CH$_2$CN, or —CO; or $R_2$ and $R_3$ taken together with their intervening atoms to form a cyclopropyl; and $R_4$ is hydrogen;

X is a covalent bond;

$R_6$ is halogen, —CN, $(C_1-C_3)$alkyl, —C(O)NH$_2$, or —SO$_2$Me;

$R_7$ is $(C_1-C_3)$alkyl, —C(O)NH$_2$, halogen, or —CN; and $R_8$ is $(C_1-C_3)$alkyl, NH$_2$, or —(CH$_2$)CONH$_2$; and the remaining variables are as described in the first, second, third, fourth, fifth, sixth, seventh, and eighth embodiment.

In other embodiments, the present invention relates to compounds as exemplified and pharmaceutically acceptable salts thereof.

In some embodiments, compounds described herein are of a formula selected from:

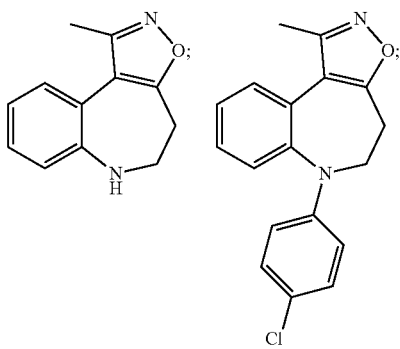

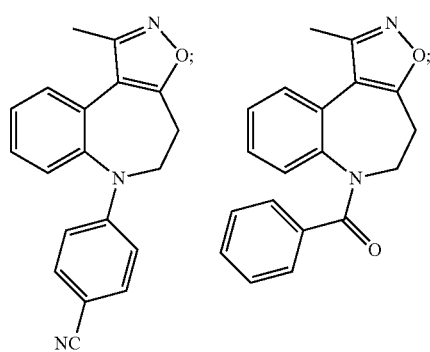

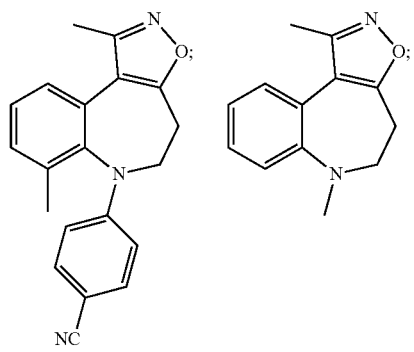

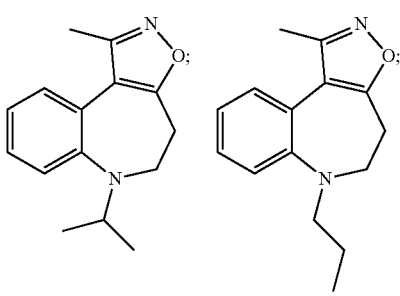

-continued
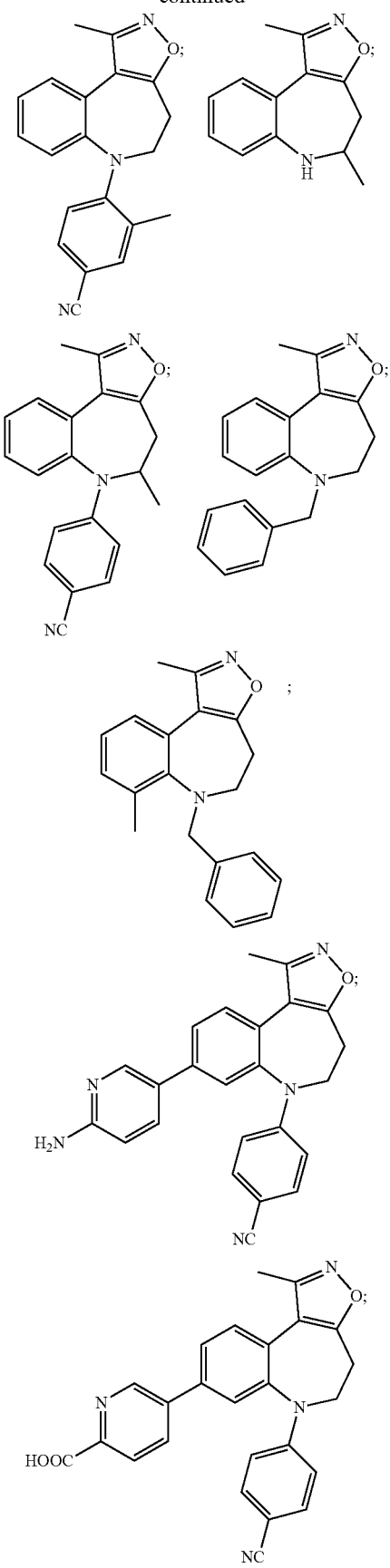
-continued
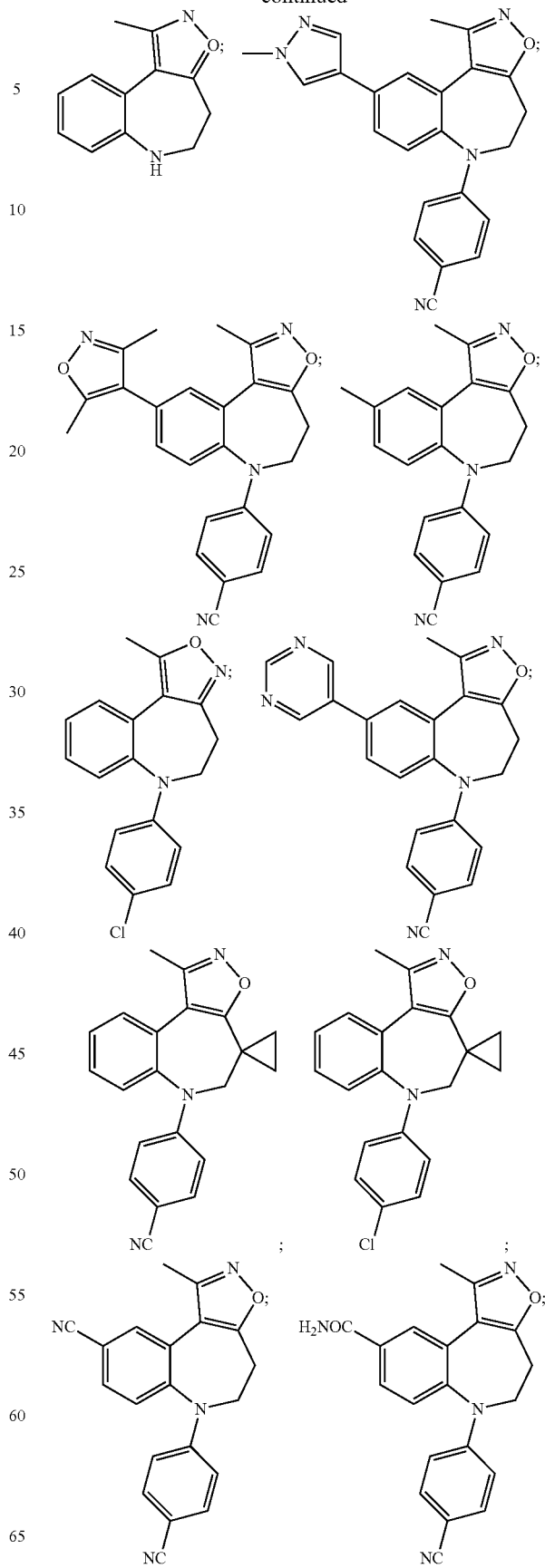

-continued
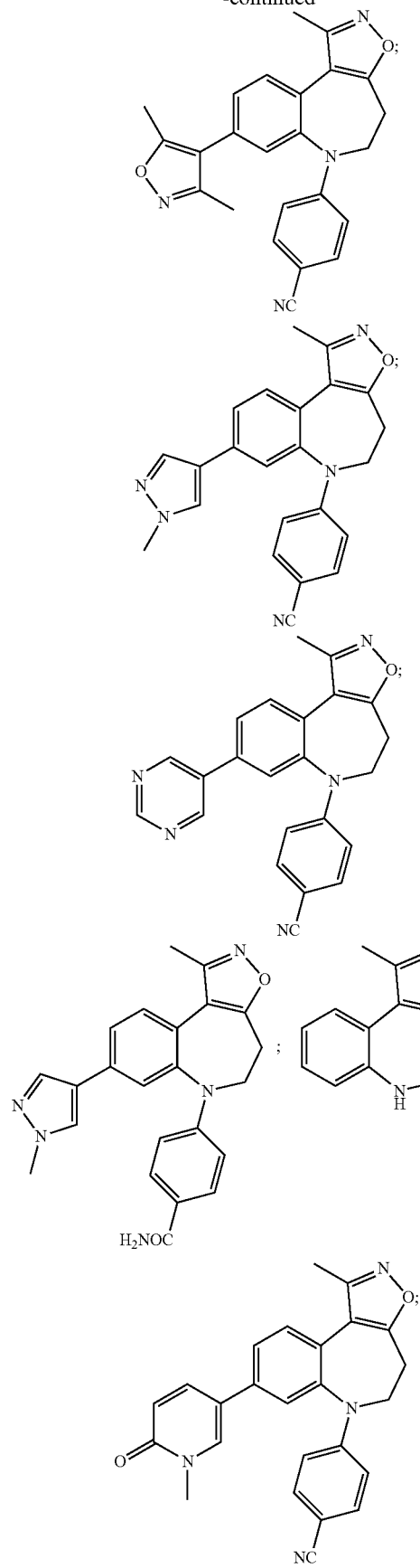
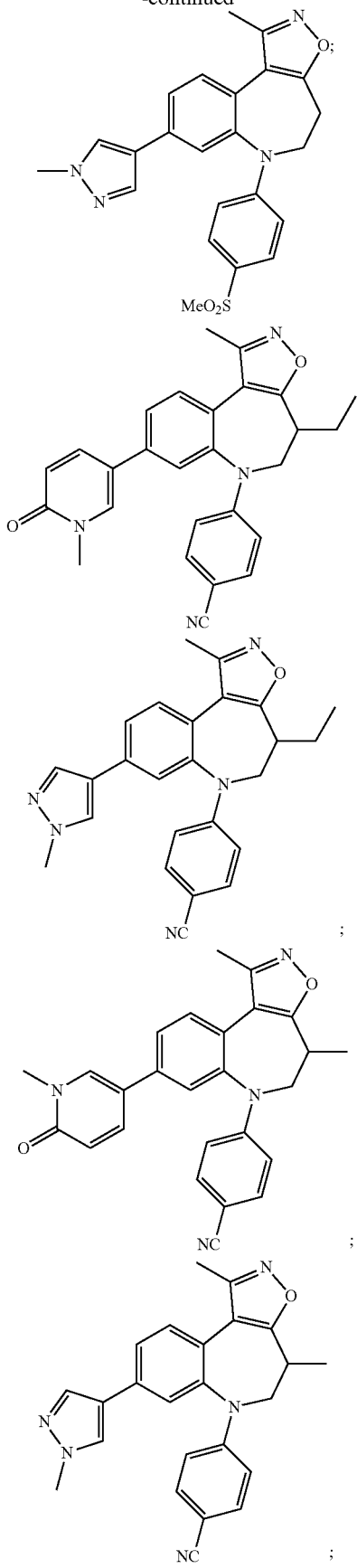

-continued

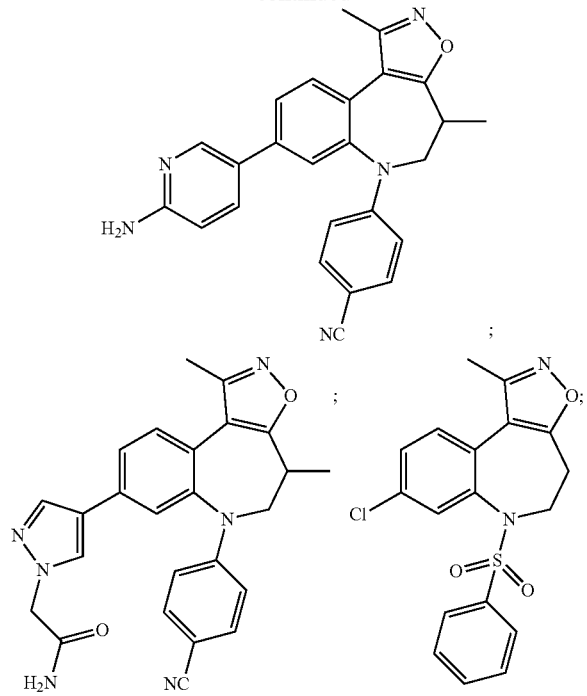

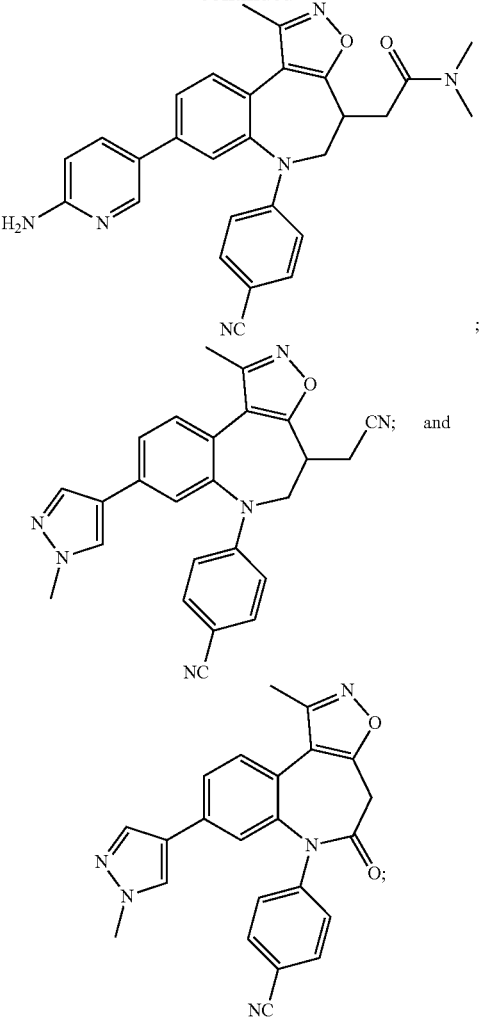

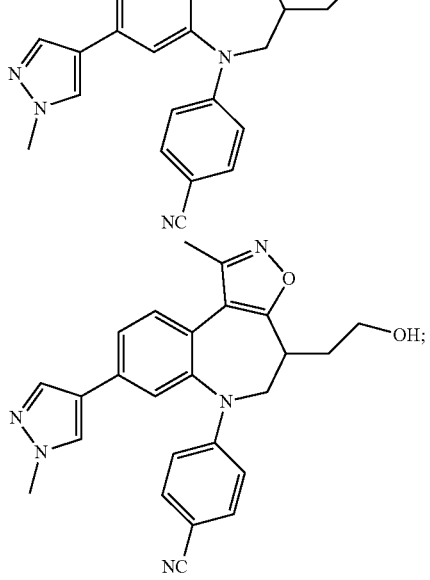

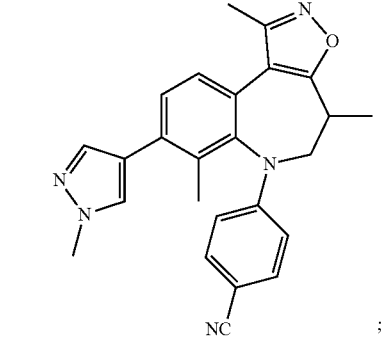

or a pharmaceutically acceptable salt thereof.

In certain embodiments, the present invention provides a method of treating a patient (e.g., a human) with a disorder modulated by a bromodomain-containing protein (such as a BET protein, e.g., BRD2, BRD3, BRD4, and/or BRDT) comprising the step of administering to the patient an effective amount of the compound with any compound described herein, or a pharmaceutically acceptable salt or composition thereof.

4. Uses, Formulation and Administration

Pharmaceutically Acceptable Compositions

According to another embodiment, the present invention provides a method of treating a patient (e.g., a human) with a disorder modulated by RORΓ using a composition comprising a compound of Formula (I) and a pharmaceutically acceptable carrier, adjuvant, or vehicle. In certain embodiments, the amount of compound of Formula (I) in a provided composition is such that is effective to measurably act as an inverse agonist or antagonist to RORΓ, in a biological sample or in a patient. In certain embodiments, a provided composition is formulated for administration to a patient in need of such composition. In some embodiments, a provided composition is formulated for oral administration to a patient.

The term "patient," as used herein, means an animal, such as a mammal, such as a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

Provided compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable compositions provided herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promotors to enhance bioavailability, fluorocarbons, and/or other conventional solubilizing or dispersing agents.

Pharmaceutically acceptable compositions provided herein may be formulated for oral administration. Such formulations may be administered with or without food. In some embodiments, pharmaceutically acceptable compositions of this disclosure are administered without food. In other embodiments, pharmaceutically acceptable compositions of this disclosure are administered with food.

The amount of provided compounds that may be combined with carrier materials to produce a composition in a single dosage form will vary depending upon the patient to be treated and the particular mode of administration. Provided compositions may be formulate such that a dosage of between 0.01-100 mg/kg body weight/day of the inhibitor can be administered to a patient receiving these compositions.

It should also be understood that a specific dosage and treatment regimen for any particular patient will depend upon a variety of factors, including age, body weight, general health, sex, diet, time of administration, rate of excretion, drug combination, the judgment of the treating physician, and the severity of the particular disease being treated. The amount of a provided compound in the composition will also depend upon the particular compound in the composition.

Uses of Compounds and Pharmaceutically Acceptable Compositions

Compounds and compositions described herein are generally useful for the inhibition of activity of one or more proteins involved in epigenetic regulation. Thus, in some embodiments, the present invention provides a method of inhibiting one or more proteins involved in epigenetic regulation, such as proteins containing acetyl-lysine recognition motifs, also known as bromodomains (e.g., BET proteins, such as BRD2, BRD3, BRD4, and/or BRDT), by administering a provided compound or composition.

Epigenetics is the study of heritable changes in gene expression caused by mechanisms other than changes in the underlying DNA sequence. Molecular mechanisms that play a role in epigenetic regulation include DNA methylation and chromatin/histone modifications. Chromatin recognition, in particular, is critical in many epigenetic phenomena.

Chromatin, the organized assemblage of nuclear DNA and histone proteins, is the basis for a multitude of vital nuclear processes including regulation of transcription, replication, DNA-damage repair and progression through the cell cycle. A number of factors, such as chromatin-modifying enzymes, have been identified that play an important role in maintaining the dynamic equilibrium of chromatin (Margueron, et al. (2005) Curr. Opin. Genet. Dev. 15:163-176).

Histones are the chief protein components of chromatin. They act as spools around which DNA winds, and they play a role in gene regulation. There are a total of six classes of histones (H1, H2A, H2B, H3, H4, and H5) organized into two super classes: core histones (H2A, H2B, H3, and H4) and linker histones (H1 and H5). The basic unit of chromatin is the nucleosome, which consists of about 147 base pairs of DNA wrapped around the histone octamer, consisting of two copies each of the core histones H2A, H2B, H3, and H4 (Luger, et al. (1997) Nature 389:251-260).

Histones, particularly residues of the amino termini of histones H3 and H4 and the amino and carboxyl termini of histones H2A, H2B and H1, are susceptible to a variety of post-translational modifications including acetylation, methylation, phosphorylation, ribosylation sumoylation, ubiquitination, citrullination, deimination, and biotinylation. The core of histones H2A and H3 can also be modified. Histone modifications are integral to diverse biological processes such as gene regulation, DNA repair, and chromosome condensation.

One type of histone modification, lysine acetylation, is recognized by bromodomain-containing proteins. Bromodomain-containing proteins are components of transcription factor complexes and determinants of epigenetic memory (Dey, et al. (2009) Mol. Biol. Cell 20:4899-4909). There are 46 human proteins containing a total of 57 bromodomains discovered to date. One family of bromodomain-containing proteins, BET proteins (BRD2, BRD3, BRD4, and BRDT) have been used to establish proof-of-concept for targeting protein-protein interactions of epigenetic "readers," as opposed to chromatin-modifying enzymes, or so-called epigenetic "writers" and "erasers" (Filippakopoulos, et al. "Selective Inhibition of BET Bromodomains," (*Nature*, 2010, 468, 1067-1073); Nicodeme, et al. "Suppression of Inflammation by a Synthetic Histone Mimic," (*Nature*, 2010, 468, 1119-1123)).

Examples of proteins inhibited by the compounds and compositions described herein and against which the methods described herein are useful include bromodomain-containing proteins, such as BET proteins, such as BRD2, BRD3, BRD4, and/or BRDT, or an isoform or mutant thereof.

The activity of a provided compound, or composition thereof, as an inhibitor of a bromodomain-containing protein, such as a BET protein, such as BRD2, BRD3, BRD4, and/or BRDT, or an isoform or mutant thereof, may be assayed in vitro, in vivo, or in a cell line. In vitro assays include assays that determine inhibition of bromodomain-containing proteins, such as BET proteins, such as BRD2, BRD3, BRD4, and/or BRDT, or a mutant thereof. Alternatively, inhibitor binding may be determined by running a competition experiment where a provided compound is incubated with a bromodomain-containing protein, such as a BET protein, such as BRD2, BRD3, BRD4, and/or BRDT bound to known ligands, labeled or unlabeled. Detailed conditions for assaying a provided compound as an inhibitor of a bromodomain-containing protein, such as a BET protein, such as BRD2, BRD3, BRD4, and/or BRDT or a mutant thereof, are set forth in the Examples below.

Acetylated histone recognition and bromodomain-containing proteins (such as BET proteins) have been implicated in proliferative disease. BRD4 knockout mice die shortly after implantation and are compromised in their ability to maintain an inner cell mass, and heterozygotes display pre- and postnatal growth defects associated with reduced proliferation rates. BRD4 regulates genes expressed during M/G1, including growth-associated genes, and remains bound to chromatin throughout the cell cycle (Dey, et al. (2009) Mol. Biol. Cell 20:4899-4909). BRD4 also physically associates with Mediator and P-TEFb (CDK9/cyclin T1) to facilitate transcriptional elongation (Yang, et al. (2005) Oncogene 24:1653-1662; Yang, et al. (2005) Mol. Cell 19:535-545). CDK9 is a validated target in chronic lymphocytic leukemia (CLL), and is linked to c-Myc-dependent transcription (Phelps, et al. Blood 113:2637-2645; Rahl, et al. (2010) Cell 141:432-445).

BRD4 is translocated to the NUT protein in patients with lethal midline carcinoma, an aggressive form of human squamous carcinoma (French, et al. (2001) Am. J. Pathol. 159:1987-1992; French, et al. (2003) Cancer Res. 63:304-307). In vitro analysis with RNAi supports a causal role for BRD4 in this recurrent t(15; 19) chromosomal translocation. Pharmacologic inhibition of the BRD4 bromodomains results in growth arrest/differentiation of BRD4-NUT cell lines in vitro and in vivo (Filippakopoulos, et al. "Selective Inhibition of BET Bromodomains," (*Nature,* 2010, 468, 1067-1073)).

Bromodomain-containing proteins (such as BET proteins) have also been implicated in inflammatory diseases. BET proteins (e.g., BRD2, BRD3, BRD4, and BRDT) regulate assembly of histone acetylation-dependent chromatin complexes that control inflammatory gene expression (Hargreaves, et al. (2009) Cell 138:129-145; LeRoy, et al. (2008) Mol. Cell 30:51-60; Jang, et al. (2005) Mol. Cell 19:523-534; Yang, et al. (2005) Mol. Cell 19:535-545). Key inflammatory genes (secondary response genes) are down-regulated upon bromodomain inhibition of the BET subfamily, and non-responsive genes (primary response genes) are poised for transcription. BET bromodomain inhibition protects against LPS-induced endotoxic shock and bacteria-induced sepsis in vivo (Nicodeme, et al. "Suppression of Inflammation by a Synthetic Histone Mimic," (*Nature,* 2010, 468, 1119-1123)).

Bromodomain-containing proteins (such as BET proteins) also play a role in viral disease. For example, BRD4 is implicated in human papilloma virus (HPV). In the primary phase of HPV infection of basal epithelia, the viral genome is maintained in an extra-chromosomal episome. In some strains of HPV, BRD4 binding to the HPV E2 protein functions to tether the viral genome to chromosomes. E2 is critical for both the repression of E6/E7 and the activation of HPV viral genes. Disruption of BRD4 or the BRD4-E2 interaction blocks E2-dependent gene activation. BRD4 also functions to tether other classes of viral genomes to host chromatin (e.g., Herpesvirus, Epstein-Barr virus).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed, i.e., therapeutic treatment. In other embodiments, treatment may be administered in the absence of symptoms. For example, treatment may be administered to a susceptible individual prior to the onset of symptoms (e.g., in light of a history of symptoms and/or in light of genetic or other susceptibility factors), i.e., prophylactic treatment. Treatment may also be continued after symptoms have resolved, for example to prevent or delay their recurrence.

In certain embodiments, a provided compound inhibits one or more of BRD2, BRD3, BRD4, BRDT, and/or another member of the bromodomain-containing proteins, or a mutant thereof. In some embodiments, a provided compound inhibits two or more of BRD2, BRD3, BRD4, BRDT, and/or another member of the bromodomain-containing proteins, or a mutant thereof. Provided compounds are inhibitors of one or more of the bromodomain-containing proteins, such as BRD2, BRD3, BRD4, and/or BRDT and are therefore useful for treating one or more disorders associated with activity of one or more of the bromodomain-containing proteins, such as BRD2, BRD3, BRD4, and/or BRDT. Thus, in certain embodiments, the present invention provides a method for treating a bromodomain-containing protein-mediated disorder, such as a BET-mediated, a BRD2-mediated, a BRD3-mediated, a BRD4-mediated disorder, and/or a BRDT-mediated disorder comprising the step of inhibiting a bromodomain-containing protein, such as a BET protein, such as BRD2, BRD3, BRD4, and/or BRDT, or a mutant thereof, by administering to a patient in need thereof a provided compound, or a pharmaceutically acceptable composition thereof.

As used herein, the terms "bromodomain-containing protein-mediated", "BET-mediated", "BRD2-mediated", "BRD3-mediated", "BRD4-mediated", and/or "BRDT-mediated" disorders or conditions means any disease or other deleterious condition in which one or more of the bromodomain-containing proteins, such as BET proteins, such as BRD2, BRD3, BRD4 and/or BRDT, or a mutant thereof, are known to play a role. Accordingly, another embodiment of the present invention relates to treating or lessening the severity of one or more diseases in which one or more of the bromodomain-containing proteins, such as BET proteins, such as BRD2, BRD3, BRD4, and/or BRDT, or a mutant thereof, are known to play a role.

Diseases and conditions treatable according to the methods of this invention include, but are not limited to, cancer and other proliferative disorders, inflammatory diseases, sepsis, autoimmune disease, and viral infection. In one embodiment, a human patient is treated with a compound of Formula (I) and a pharmaceutically acceptable carrier, adjuvant, or vehicle, wherein said compound is present in an amount to measurably inhibit bromodomain-containing protein activity (such as BET protein, e.g., BRD2, BRD3, BRD4, and/or BRDT) in the patient.

The invention further relates to a method for treating or ameliorating cancer or another proliferative disorder by administration of an effective amount of a compound according to this invention to a mammal, in particular a human in need of such treatment. In some aspects of the invention, the disease to be treated by the methods of the present invention is cancer. Examples of cancers treated using the compounds and methods described herein include, but are not limited to, adrenal cancer, acinic cell carcinoma, acoustic neuroma, acral lentigious melanoma, acrospiroma, acute eosinophilic leukemia, acute erythroid leukemia, acute lymphoblastic leukemia, acute megakaryoblastic leukemia, acute monocytic leukemia, actue promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogeous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pineaoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, preimary peritoneal cancer, prostate cancer, pancreatic cancer, pharyngeal cancer, pseudomyxoma periotonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In some embodiments, the present invention provides a method of treating a benign proliferative disorder. Such benign proliferative disorders include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratosis, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The invention further relates to a method for treating infectious and noninfectious inflammatory events and autoimmune and other inflammatory diseases by administration of an effective amount of a provided compound to a mammal, in particular a human in need of such treatment. Examples of autoimmune and inflammatory diseases, disorders, and syndromes treated using the compounds and methods described herein include inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherssclerosis, Addison's disease, Parkinson's disease, Alzheimer's disease, Type I diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituatarism, Guillain-Barre syndrome, Behcet's disease, scleracierma, mycosis fungoides, acute inflammatory responses (such as acute respiratory distress syndrome and ischemia/reperfusion injury), and Graves' disease.

In some embodiments, the present invention provides a method of treating systemic inflammatory response syndromes such as LPS-induced endotoxic shock and/or bacteria-induced sepsis by administration of an effective amount of a provided compound to a mammal, in particular a human in need of such treatment.

The invention further relates to a method for treating viral infections and diseases by administration of an effective amount of a provided compound to a mammal, in particular a human in need of such treatment. Examples of viral infections and diseases treated using the compounds and methods described herein include episome-based DNA viruses including, but not limited to, human papillomavirus, Herpesvirus, Epstein-Barr virus, human immunodeficiency virus, hepatis B virus, and hepatitis C virus.

The invention further provides a method of treating a subject, such as a human, suffering from one of the above-mentioned conditions, illnesses, disorders or diseases. The method comprises administering a therapeutically effective amount of one or more provided compounds, which function by inhibiting a bromodomain and, in general, by modulating gene expression, to induce various cellular effects, in particular induction or repression of gene expression, arresting cell proliferation, inducing cell differentiation and/or inducing apoptosis, to a subject in need of such treatment.

The invention further provides a therapeutic method of modulating protein methylation, gene expression, cell proliferation, cell differentiation and/or apoptosis in vivo in diseases mentioned above, in particular cancer, inflammatory disease, and/or viral disease comprising administering to a subject in need of such therapy a pharmacologically active and therapeutically effective amount of one or more provided compounds.

The invention further provides a method of regulating endogenous or heterologous promoter activity by contacting a cell with a provided compound.

The invention further relates to the use of provided compounds for the production of pharmaceutical compositions which are employed for the treatment and/or prophylaxis and/or amelioration of the diseases, disorders, illnesses and/or conditions as mentioned herein.

The invention further relates to the use of provided compounds for the production of pharmaceutical compositions which are employed for the treatment and/or prophylaxis of diseases and/or disorders responsive or sensitive to the inhibition of bromodomain-containing proteins, particularly those diseases mentioned above, such as e.g. cancer, inflammatory disease, viral disease.

Compounds or compositions described herein may be administered using any amount and any route of administration effective for treating or lessening the severity of cancer or other proliferative disorder. The exact amount required will vary from subject to subject, depending on the species, age, and general condition of the subject, the severity of the infection, the particular agent, its mode of administration, and the like. Provided compounds are preferably formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this disclosure can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, provided compounds may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

According to some embodiments, the invention relates to a method of inhibiting bromodomain-containing proteins in a biological sample comprising the step of contacting said biological sample with a provided compound, or a composition thereof.

According to some embodiments, the invention relates to a method of inhibiting a bromodomain-containing protein, such as a BET protein, such as BRD2, BRD3, BRD4 and/or BRDT, or a mutant thereof, activity in a biological sample comprising the step of contacting said biological sample with a provided compound, or a composition thereof.

The term "biological sample", as used herein, includes, without limitation, cell cultures or extracts thereof, biopsied material obtained from a mammal or extracts thereof, and blood, saliva, urine, feces, semen, tears, or other body fluids or extracts thereof.

Inhibition of activity of a protein, e.g., a bromodomain-containing protein, such as a BET protein, such as BRD2, BRD3, BRD4 and/or BRDT, or a mutant thereof, in a biological sample is useful for a variety of purposes that are known to one of skill in the art. Examples of such purposes include, but are not limited to, blood transfusion, organ-transplantation, biological specimen storage, and biological assays.

According to another embodiment, the invention relates to a method of inhibiting activity of one or more bromodomain-containing protein, such as a BET protein, such as BRD2, BRD3, BRD4, and/or BRDT, or a mutant thereof, in a patient comprising the step of administering to said patient a provided compound, or a composition comprising said compound. In certain embodiments, the present invention provides a method for treating a disorder mediated by one or more bromodomain-containing proteins, such as a BET protein, such as BRD2, BRD3, BRD4, and/or BRDT, or a mutant thereof, in a patient in need thereof, comprising the step of administering to said patient a provided compound or pharmaceutically acceptable composition thereof. Such disorders are described in detail herein.

Depending upon the particular condition, or disease, to be treated, additional therapeutic agents that are normally administered to treat that condition may also be present in the compositions of this disclosure or administered separately as a part of a dosage regimen. As used herein, additional therapeutic agents that are normally administered to treat a particular disease, or condition, are known as "appropriate for the disease, or condition, being treated."

In some embodiments, the additional therapeutic agent is an epigenetic drug. As used herein, the term "epigenetic drug" refers to a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, but are not limited to, vorinostat.

Other therapies, chemotherapeutic agents, or other antiproliferative agents may be combined with a provided compound to treat proliferative diseases and cancer. Examples of therapies or anticancer agents that may be used in combination with compounds of formula I include surgery, radiotherapy (e.g., gamma-Radiation, neutron beam radiotherapy, electron beam radiotherapy, proton therapy, brachytherapy, and systemic radioactive isotopes), endocrine therapy, a biologic response modifier (e.g., an interferon, an interleukin, tumor necrosis factor (TNF), hyperthermia and cryotherapy, an agent to attenuate any adverse effects (e.g., an antiemetic), and any other approved chemotherapeutic drug.

A provided compound may also be used to advantage in combination with one or more antiproliferative compounds. Such antiproliferative compounds include an aromatase inhibitor; an anti-estrogen; an anti-androgen; a gonadorelin agonist; a topoisomerase I inhibitor; a topoisomerase II inhibitor; a microtubule active agent; an alkylating agent; a retinoid, a carontenoid, or a tocopherol; a cyclooxygenase inhibitor; an MMP inhibitor; an mTOR inhibitor; an antimetabolite; a platin compound; a methionine aminopeptidase inhibitor; a bisphosphonate; an antiproliferative antibody; a heparanase inhibitor; an inhibitor of Ras oncogenic isoforms; a telomerase inhibitor; a proteasome inhibitor; a compound used in the treatment of hematologic malignancies; a Flt-3 inhibitor; an Hsp90 inhibitor; a kinesin spindle protein inhibitor; a MEK inhibitor; an antitumor antibiotic; a nitrosourea; a compound targeting/decreasing protein or lipid kinase activity, a compound targeting/decreasing protein or lipid phosphatase activity, or any further anti-angiogenic compound.

Exemplary aromatase inhibitors include steroids, such as atamestane, exemestane and formestane, and non-steroids, such as aminoglutethimide, roglethimide, pyridoglutethimide, trilostane, testolactone, ketoconazole, vorozole, fadrozole, anastrozole and letrozole.

Exemplary anti-estrogens include tamoxifen, fulvestrant, raloxifene and raloxifene hydrochloride. Anti-androgens include, but are not limited to, bicalutamide. Gonadorelin agonists include, but are not limited to, abarelix, goserelin and goserelin acetate.

Exemplary topoisomerase I inhibitors include topotecan, gimatecan, irinotecan, camptothecin and its analogues, 9-nitrocamptothecin and the macromolecular camptothecin conjugate PNU-166148. Topoisomerase II inhibitors include, but are not limited to, the anthracyclines such as doxorubicin, daunorubicin, epirubicin, idarubicin and nemorubicin, the anthraquinones mitoxantrone and losoxantrone, and the podophillotoxines etoposide and teniposide.

Exemplary microtubule active agents include microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; colchicine and epothilones and derivatives thereof.

Exemplary alkylating agents include cyclophosphamide, ifosfamide, melphalan or nitrosoureas such as carmustine and lomustine.

Exemplary cyclooxygenase inhibitors include Cox-2 inhibitors, 5-alkyl substituted 2-arylaminophenylacetic acid and derivatives, such as celecoxib, rofecoxib, etoricoxib, valdecoxib or a 5-alkyl-2-arylaminophenylacetic acid, such as lumiracoxib.

Exemplary matrix metalloproteinase inhibitors ("MMP inhibitors") include collagen peptidomimetic and nonpeptidomimetic inhibitors, tetracycline derivatives, batimastat, marimastat, prinomastat, metastat, BMS-279251, BAY 12-9566, TAA211, MMI270B, and AAJ996.

Exemplary mTOR inhibitors include compounds that inhibit the mammalian target of rapamycin (mTOR) and possess antiproliferative activity such as sirolimus, everolimus, CCI-779, and ABT578.

Exemplary antimetabolites include 5-fluorouracil (5-FU), capecitabine, gemcitabine, DNA demethylating compounds, such as 5-azacytidine and decitabine, methotrexate and edatrexate, and folic acid antagonists such as pemetrexed.

Exemplary platin compounds include carboplatin, cisplatin, cisplatinum, and oxaliplatin.

Exemplary methionine aminopeptidase inhibitors include bengamide or a derivative thereof and PPI-2458.

Exemplary bisphosphonates include etridonic acid, clodronic acid, tiludronic acid, pamidronic acid, alendronic acid, ibandronic acid, risedronic acid and zoledronic acid.

Exemplary antiproliferative antibodies include trastuzumab, trastuzumab-DM1, cetuximab, bevacizumab, rituximab, PRO64553, and 2C4. The term"antibody" is meant to include intact monoclonal antibodies, polyclonal antibodies, multispecific antibodies formed from at least two intact antibodies, and antibody fragments, so long as they exhibit the desired biological activity.

Exemplary heparanase inhibitors include compounds that target, decrease or inhibit heparin sulfate degradation, such as PI-88 and OGT2115.

The term "an inhibitor of Ras oncogenic isoforms," such as H-Ras, K-Ras, or N-Ras, as used herein refers to a compound which targets, decreases, or inhibits the oncogenic activity of Ras; for example, a farnesyl transferase inhibitor such as L-744832, DK8G557, tipifarnib, and lonafarnib.

Exemplary telomerase inhibitors include compounds that target, decrease or inhibit the activity of telomerase, such as compounds which inhibit the telomerase receptor, such as telomestatin.

Exemplary proteasome inhibitors include compounds that target, decrease or inhibit the activity of the proteasome including, but not limited to, bortezomib.

The phrase "compounds used in the treatment of hematologic malignancies" as used herein includes FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Exemplary Flt-3 inhibitors include PKC412, midostaurin, a staurosporine derivative, SU11248 and MLN518.

Exemplary HSP90 inhibitors include compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The phrase "a compound targeting/decreasing a protein or lipid kinase activity; or a protein or lipid phosphatase activity; or any further anti-angiogenic compound" as used herein includes a protein tyrosine kinase and/or serine and/or threonine kinase inhibitor or lipid kinase inhibitor, such as a) a compound targeting, decreasing or inhibiting the activity of the platelet-derived growth factor-receptors (PDGFR), such as a compound which targets, decreases, or inhibits the activity of PDGFR, such as an N-phenyl-2-pyrimidine-amine derivatives, such as imatinib, SU101, SU6668 and GFB-111; b) a compound targeting, decreasing or inhibiting the activity of the fibroblast growth factor-receptors (FGFR); c) a compound targeting, decreasing or inhibiting the activity of the insulin-like growth factor receptor I (IGF-IR), such as a compound which targets, decreases, or inhibits the activity of IGF-IR; d) a compound targeting, decreasing or inhibiting the activity of the Trk receptor tyrosine kinase family, or ephrin B4 inhibitors; e) a compound targeting, decreasing or inhibiting the activity of the Ax1 receptor tyrosine kinase family; f) a compound targeting, decreasing or inhibiting the activity of the Ret receptor tyrosine kinase; g) a compound targeting, decreasing or inhibiting the activity of the Kit/SCFR receptor tyrosine kinase, such as imatinib; h) a compound targeting, decreasing or inhibiting the activity of the c-Kit receptor tyrosine kinases, such as imatinib; i) a compound targeting, decreasing or inhibiting the activity of members of the c-Abl family, their gene-fusion products (e.g. Bcr-Abl kinase) and mutants, such as an N-phenyl-2-pyrimidine-amine derivative, such as imatinib or nilotinib; PD180970; AG957; NSC 680410; PD173955; or dasatinib; j) a compound targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK), such as a staurosporine derivative disclosed in U.S. Pat. No. 5,093,330, such as midostaurin; examples of further compounds include UCN-01, safingol, BAY 43-9006, bryostatin 1, perifosine; ilmofosine; RO 318220 and RO 320432; GO 6976; lsis 3521; LY333531/LY379196; a isochinoline compound; a farnesyl transferase inhibitor; PD184352 or QAN697, or AT7519; k) a compound targeting, decreasing or inhibiting the activity of a protein-tyrosine kinase, such as imatinib mesylate or a tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl) methyl]amino}-benzoic acid adamantyl ester; NSC 680410, adaphostin); 1) a compound targeting, decreasing or inhibiting the activity of the epidermal growth factor family of receptor tyrosine kinases (EGFR, ErbB2, ErbB3, ErbB4 as homo- or heterodimers) and their mutants, such as CP 358774, ZD 1839, ZM 105180; trastuzumab, cetuximab, getfitinib, erlotinib, OSI-774, C1-1033, EKB-569, GW-2016, antibodies E1.1, E2.4, E2.5, E6.2, E6.4, E2.11, E6.3 and E7.6.3, and 7H-pyrrolo-[2,3-d]pyrimidine derivatives; and m) a compound targeting, decreasing or inhibiting the activity of the c-Met receptor.

Exemplary compounds that target, decrease or inhibit the activity of a protein or lipid phosphatase include inhibitors of phosphatase 1, phosphatase 2A, or CDC25, such as okadaic acid or a derivative thereof.

Further anti-angiogenic compounds include compounds having another mechanism for their activity unrelated to protein or lipid kinase inhibition, e.g. thalidomide and TNP-470.

Additional exemplary chemotherapeutic compounds, one or more of which may be used in combination with provided compounds, include: daunorubicin, adriamycin, Ara-C, VP-16, teniposide, mitoxantrone, idarubicin, carboplatinum, PKC412, 6-mercaptopurine (6-MP), fludarabine phosphate, octreotide, SOM230, FTY720, 6-thioguanine, cladribine, 6-mercaptopurine, pentostatin, hydroxyurea, 2-hydroxy-1H-isoindole-1,3-dione derivatives, 1-(4-chloroanilino)-4-(4-pyridylmethyl)phthalazine or a pharmaceutically acceptable salt thereof, 1-(4-chloroanilino)-4-(4-pyridylmethyl) phthalazine succinate, angiostatin, endostain, anthranilic acid amides, ZD4190, ZD6474, SU5416, SU6668, bevacizumab, rhuMAb, rhuFab, macugon; FLT-4 inhibitors, FLT-3 inhibitors, VEGFR-2 IgGI antibody, RPI 4610, bevacizumab, porfimer sodium, anecortave, triamcinolone, hydrocortisone, 11-α-epihydrocotisol, cortexolone, 17α-hydroxy-progesterone, corticosterone, desoxycorticosterone, testosterone, estrone, dexamethasone, fluocinolone, a plant alkaloid, a hormonal compound and/or antagonist, a biological response modifier, such as a lymphokine or interferon, an antisense oligonucleotide or oligonucleotide derivative, shRNA or siRNA, or a miscellaneous compound or compound with other or unknown mechanism of action.

For a more comprehensive discussion of updated cancer therapies see, The Merck Manual, Seventeenth Ed. 1999, the entire contents of which are hereby incorporated by reference. See also the National Cancer Institute (CNI) website (www.nci.nih.gov) and the Food and Drug Administration (FDA) website for a list of the FDA approved oncology drugs.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinrole, pramipexole, bromocriptine, pergolide, trihexephendyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

The above-mentioned compounds, one or more of which can be used in combination with a provided compound, can be prepared and administered as described in the art.

Provided compounds can be administered alone or in combination with one or more other therapeutic compounds, possible combination therapy taking the form of fixed combinations or the administration of a provided compound and one or more other therapeutic compounds being staggered or given independently of one another, or the combined administration of fixed combinations and one or more other therapeutic compounds. Provided compounds can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Such additional agents may be administered separately from a composition containing a provided compound, as part of a multiple dosage regimen. Alternatively, those agents may be part of a single dosage form, mixed together with a provided compound in a single composition. If administered as part of a multiple dosage regimen, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, an embodiment of the invention provides a single unit dosage form comprising a provided compound, an additional therapeutic agent, and a pharmaceutically acceptable carrier, adjuvant, or vehicle for use in the methods of the invention.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions should be formulated such that a dosage of between 0.01-100 mg/kg body weight/day of a provided compound can be administered.

In those compositions which comprise an additional therapeutic agent, that additional therapeutic agent and the provided compound may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this disclosure will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Provided compounds, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a provided compound. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation of Compounds of Formula I

Example 1

Synthesis of 1-(3-methylisoxazol-5-yl)cyclopropanecarboxylic acid

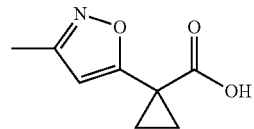

To a vigorously stirred solution of ethyl 2-(3-methylisoxazol-5-yl)acetate (17.83 g, 105 mmol) in toluene (180 mL) was sequentially added tetra-n-butylammonium bromide (3.69 g, 11.45 mmol), 1,2-dibromoethane (15.0 mL, 174 mmol), and 50% sodium hydroxide (55.0 mL, 1067 mmol). The reaction mixture was vigorously stirred at room temperature. After 24 h, organic layer was removed, the aqueous layer was subsequently cooled to 0° C., and acidified to pH 1 with 6 N HCl. The reaction mixture turned heterogeneous and the product precipitated out of solution. The solids were filtered, washed with water (3×250 mL), and dried to give 1-(3-methylisoxazol-5-yl)cyclopropanecarboxylic acid (13.39 g, 80 mmol, 76% yield) as white solids. m/z (ESI) 168 [M+H]⁺.

General procedure for alkylation of 2-(3-methylisoxazol-5-yl)acetic acid

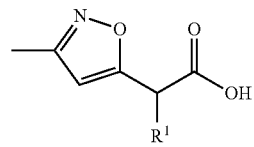

To a round-bottomed flask charged with 2-(3-methylisoxazol-5-yl)acetic acid (1 eq.) and THF (~0.2 M) at −78° C. was added nBuLi (2.2 eq.) and the solution stirred at −78° C. for 5 min before warming to 0° C. for 20 min. After 20 min, the solution was cooled to −78° C. and alkyl halide (~2 eq.) was added and the solution stirred for 1 h at −78° C.

This solution was quenched via the addition of sat. aq. NaHCO$_3$ and diluted with ether. The layers were separated and the aqueous layer was washed with ether (1×). The ether layer was discarded and the aqueous phase was acidified with 1N HCl before extracting with EtOAc. The combined organics layer was washed with brine, dried over Na$_2$SO$_4$, filtered, and concentrated to afford the alkylated isoxazole in sufficient purity to be used directly in the next step.

General Scheme for Synthesis of
Isoxazole-Azepines

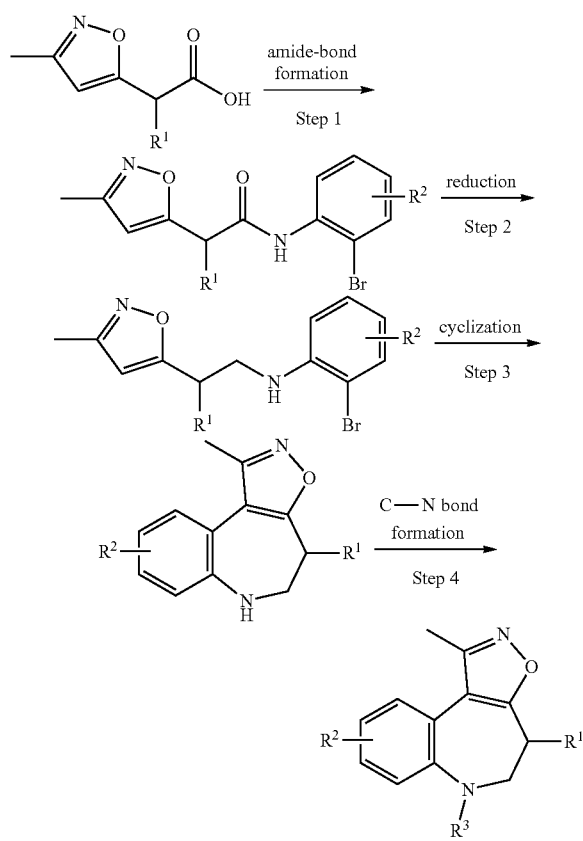

Step 1: General Procedure for Amide Bond Formation

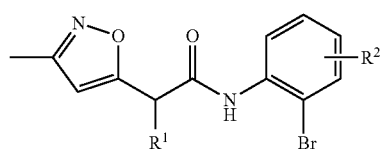

To a suspension of the appropriate isoxazole carboxylic acid (1 eq.) in CH$_2$Cl$_2$ (~1 M) was sequentially added DMF (0.1 eq.) and oxalyl chloride (1.1 eq.) dropwise. Vigorous gas evolution was observed and stirring was continued for 30 min after bubbling ceased. This mixture was cooled in an ice bath and diluted with CH$_2$Cl$_2$ (~0.2 M final conc.) before addition of the bromo-aniline (1 eq.). To this heterogeneous mixture was slowly added Et$_3$N (1 eq.) and the reaction was warmed to room temperature and stirred until complete (~2 h) as judged by LCMS. The reaction mixture was partitioned between EtOAc and Water. The biphasic mixture was filtered over a pad of Celite to facilitate phase separation. The aqueous phase was extracted with EtOAc (3×). The combined organic extracts were washed with water, brine, dried over Na$_2$SO$_4$, filtered, and concentrated to afford the crude residue. The crude residue was triturated with EtOAc:Hex (1:5) and filtered to afford the desired aniline as dark brown solids. Alternatively, the crude product could be purified via silica gel chromatography to afford the desired amide (50%).

Step 2: General Procedure for Amide Reduction

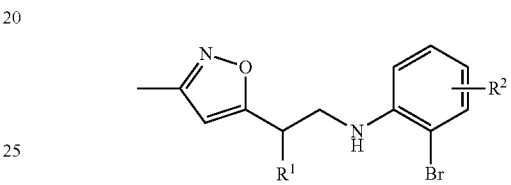

To a solution of the isoxazole-amide (1 eq.) in THF (~0.3 M) was added BH$_3$.THF (2 eq.). The reaction vessel was fitted with a reflux condenser and heated to reflux until the reaction was complete as judged by LCMS (~2 h). The solution was then cooled to room temperature before dropwise addition of MeOH (caution gas evolution). After bubbling had ceased the solution was heated to 65° C. for 2 h. The solution was cooled to room temperature and concentrated. The crude residue was purified via silica gel chromatography to afford the desired aniline (50%).

Step 3: General Procedure for Cyclization

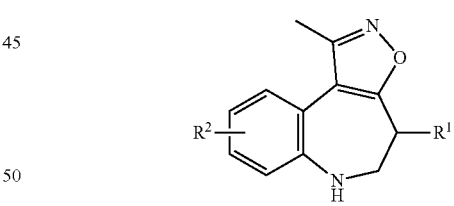

A resealable vial was charged with isoxazole-aniline (1 eq.), KOAc (2 eq.), tetrabutylammonium chloride (1 eq.), and a stirbar. The vial was sealed before being evacuated/purged with N$_2$ (3×). The solids were suspended in DMAc (~0.3 M), and the mixture was stirred at 135° C. until complete as judged by LCMS (2-8 h). The solution was then cooled to room temperature and partitioned between EtOAc and water. The aqueous layer was acidified with 1N HCl (pH~1) and extracted with EtOAc (3×). The combined organics layer was washed with sat. aq. NaHCO$_3$ and brine, dried over Na$_2$SO$_4$, filtered, and concentrated. The crude residue was purified via silica gel chromatography to afford the cyclized product (~30-60%).

Step 4: General Procedure for C—N Bond Formation

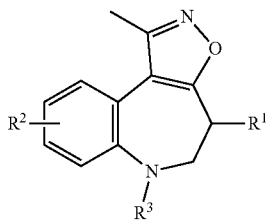

A resealable vial was charged with isoxazole azepine (1 eq.), aryl iodide (1.3 eq.), chloro(2-dicyclohexylphosphino-2',6'-di-i-propoxy-1,1'-biphenyl)[2-(2-aminoethylphenyl)]palladium(II) [CAS 1028206-60-1] (0.02 eq.), cesium carbonate (2.4 eq.), and a stirbar before being evacuated/backfilled with $N_2$ (3×). To this vial was added dioxane (0.1 M) and the mixture was heated to 100° C. until complete as judged by LCMS (generally 2-10 h). The solution was then cooled to room temperature and diluted with EtOAc. The mixture was filtered over celite and the filtrate concentrated. The crude residue was purified via silica gel chromatography to afford the desired isoxazole azepine. (70-95%).

Example 2

Synthesis of 1-methyl-5,6-dihydro-4H-benzo[b]isoxazolo[4,5-d]azepine (100)

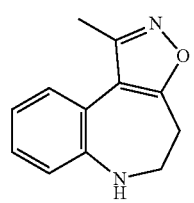

This compound was synthesized following the general procedures outlined above starting from 2-(3-methylisoxazol-5-yl)acetic acid and 2-bromoaniline LC/MS: 201 [M+1].

Example 3

Compounds 101-108 were Synthesized Following the General Procedures Outlined Above

| Compound # | Formula | NMR | LCMS |
|---|---|---|---|
| 101 | 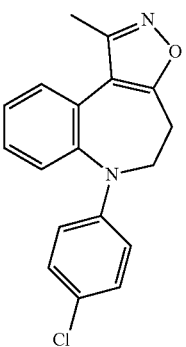 [SMILES: Cc1noc2c1-c1ccccc1N(c1ccc(Cl)cc1)CC2] | $^1$H NMR (400 MHz, DMSO-d6) δ 7.84-7.80 (m, 1H), 7.43-7.31 (m, 3H), 7.15 (d, J = 9.16 Hz, 2H), 6.72 (d, J = 9.16 Hz, 2H), 3.92 (t, J = 6.18 Hz, 2H), 3.26 (t, J = 6.18 Hz, 2H), 2.45 (s, 3H) | 311 |
| 102 | 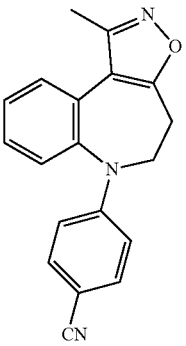 [SMILES: Cc1noc2c1-c1ccccc1N(c1ccc(C#N)cc1)CC2] | $^1$H NMR (400 MHz, DMSO-d6) δ 7.85 (dd, J = 1.37, 7.78 Hz, 1H), 7.54 (d, J = 8.93 Hz, 2H), 7.50-7.35 (m, 3H), 6.82 (d, J = 8.01 Mz, 2H), 4.28-3.87 (m, 2H), 3.38-3.27 (m, 2H), 2.45 (s, 3H) | 302 |

-continued

| Compound # | Formula | NMR | LCMS |
|---|---|---|---|
| 103 | | ¹H NMR (400 MHz, DMSO-d6) δ 7.65 (d, J = 7.78 Hz, 3H), 7.48-7.19 (m, 4H), 4.73-4.53 (m, 1H), 3.55-3.36 (m, 2H), 3.21 (dd, J = 3.55, 17.51 Hz, 1H), 2.41 (s, 3H), 2.07 (s, 3H) | 457 |
| 104 | | ¹H NMR (400 MHz, DMSO-d6) δ 8.10 (s, 1 H), 7.85 (dd, J = 1.9, 8.1 Hz, 1 H), 7.82 (d, J = 0.6 Hz, 1 H), 7.74 (d, J = 8.3 Hz, 1 H), 7.47-7.39 (m, 4 H), 7.39 (s, 1 H), 3.82 (s, 3 H), 2.53 (s, 3 H), 1.28 (d, J = 10.2 Hz, 4 H) | 328 |
| 105 | | ¹H NMR (400 MHz, DMSO-d6) δ 7.74-7.80 (m, 1H), 7.39-7.30 (m, 2H), 7.27-7.22 (m, 1H), 7.16-7.10 (m, 2H), 6.83-6.76 (m, 2H), 3.90 (s, 2H), 2.43 (s, 3H), 1.23 (s, 4H) | 337 |
| 106 | | 1H NMR (400 MHz, DMSO-d6) δ 7.63 (s, 1H), 7.52 (d, J = 9.14 Hz, 2H), 7.27-7.19 (m, 2H), 6.84-6.76 (m, 2H), 4.12-3.86 (m, 2H), 3.30 (br. s, 2H), 2.45 (s, 3H), 2.42 (s, 3H) | 316 |

| Compound # | Formula | NMR | LCMS |
|---|---|---|---|
| 107 | 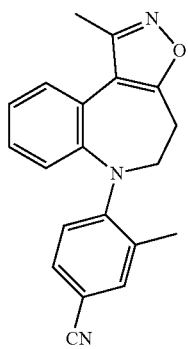 [SMILES: Cc1cc(C#N)ccc1N1CCc2onc(C)c2-c2ccccc21] | ¹H NMR (400 MHz, DMSO-d6) δ 7.79-7.69 (m, 2H), 7.60 (d, J = 8.24 Hz, 1H), 7.57 (dd, J = 0.57, 1.95 Hz, 1H), 7.14 (dtd, J = 1.60, 7.41, 18.83 Hz, 2H), 6.54 (dd, J = 1.49, 7.90 Hz, 1H), 3.96 (br. s., 2H), 3.13 (t, J = 5.84 Hz, 2H), 2.49 (s, 3H), 1.56 (s, 3H) | 316 |
| 108 | 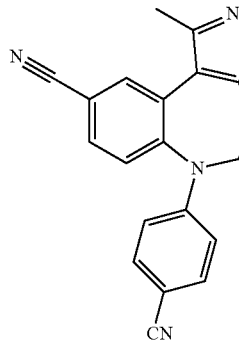 | ¹H NMR (400 MHz, DMSO-d6) δ 8.28 (d, J = 1.87 Hz, 1H), 7.84 (dd, J = 1.87, 8.31 Hz, 1H), 7.59 (dd, J = 1.87, 8.52 Hz, 3H), 6.92 (d, J = 8.93 Hz, 2H), 4.03 (d, J = 3.95 Hz, 2H), 3.29 (t, J = 6.02 Hz, 2H), 2.53-2.47 (m, 3H) | 327 |

General Suzuki coupling protocol.

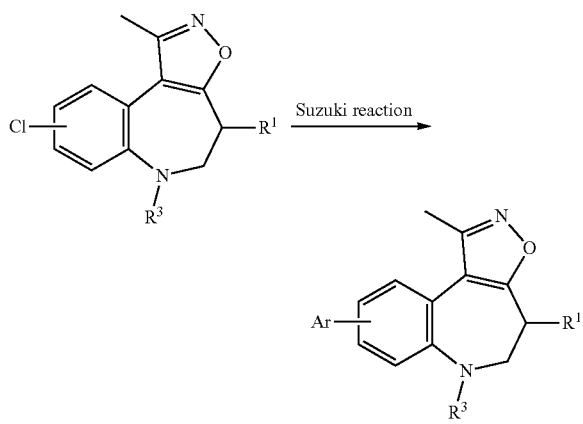

To a resealable vial charged with chloro-aniline (1 eq., accessible following the general synthetic scheme) was added $Pd_2(dba)_3$ (0.02 eq.), tri-tert-butylphosphonium tetrafluoroborate (0.04 eq.), potassium phosphate hydrate (2.4 eq.), and boronic acid/boronic ester reagent (2-3 eq.). The vial was sealed and evacuated/backfilled with $N_2$ (3×) before addition of 20:1 dioxane:water (0.2 M) and heating the solution to 100° C. until complete as judged by LCMS (generally 1-2 h). The reaction was cooled to room temperature and diluted with EtOAc. The mixture was filtered over Celite and the filtrate concentrated. The crude product was purified via silica gel chromatography to afford the coupled isoxazole azepine products. (50-85%)

Example 4
Compounds 109-125 were Synthesized According to the General Procedures
| Compound # | Formula | NMR | LCMS |
|---|---|---|---|
| 109 | 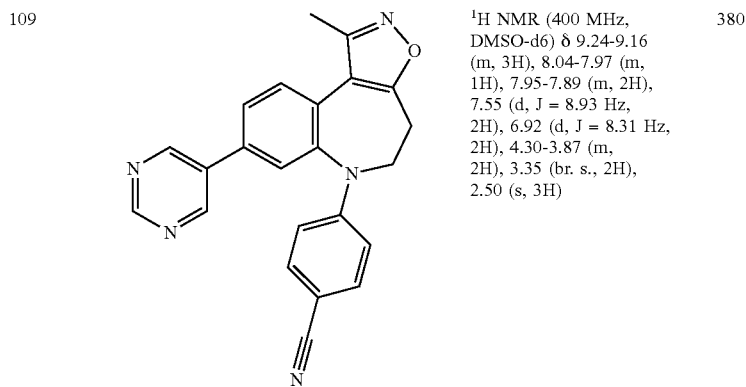 | $^1$H NMR (400 MHz, DMSO-d6) δ 9.24-9.16 (m, 3H), 8.04-7.97 (m, 1H), 7.95-7.89 (m, 2H), 7.55 (d, J = 8.93 Hz, 2H), 6.92 (d, J = 8.31 Hz, 2H), 4.30-3.87 (m, 2H), 3.35 (br. s., 2H), 2.50 (s, 3H) | 380 |
| 110 | 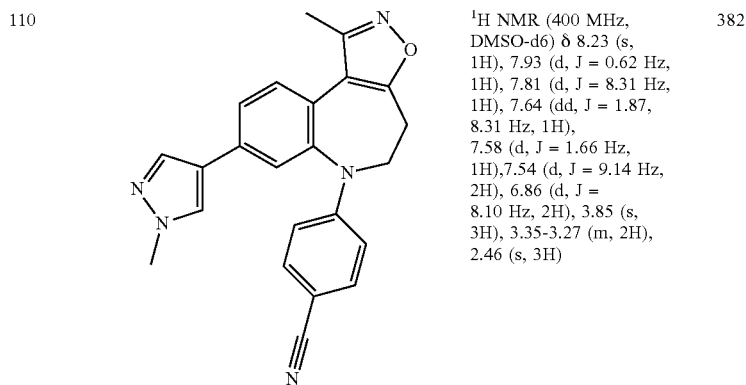 | $^1$H NMR (400 MHz, DMSO-d6) δ 8.23 (s, 1H), 7.93 (d, J = 0.62 Hz, 1H), 7.81 (d, J = 8.31 Hz, 1H), 7.64 (dd, J = 1.87, 8.31 Hz, 1H), 7.58 (d, J = 1.66 Hz, 1H), 7.54 (d, J = 9.14 Hz, 2H), 6.86 (d, J = 8.10 Hz, 2H), 3.85 (s, 3H), 3.35-3.27 (m, 2H), 2.46 (s, 3H) | 382 |
| 111 | 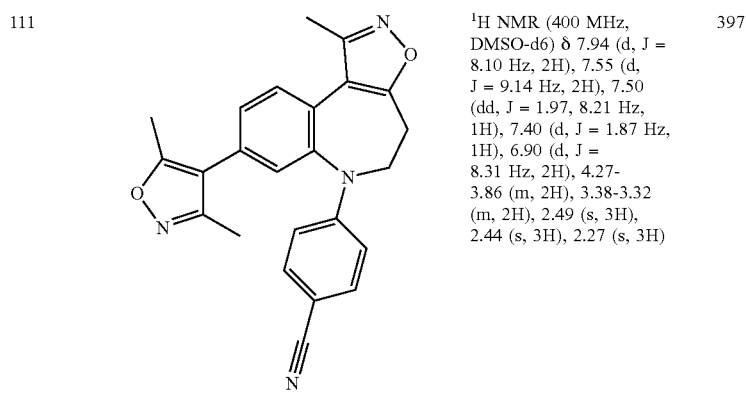 | $^1$H NMR (400 MHz, DMSO-d6) δ 7.94 (d, J = 8.10 Hz, 2H), 7.55 (d, J = 9.14 Hz, 2H), 7.50 (dd, J = 1.97, 8.21 Hz, 1H), 7.40 (d, J = 1.87 Hz, 1H), 6.90 (d, J = 8.31 Hz, 2H), 4.27-3.86 (m, 2H), 3.38-3.32 (m, 2H), 2.49 (s, 3H), 2.44 (s, 3H), 2.27 (s, 3H) | 397 |

-continued

| Compound # | Formula | NMR | LCMS |
|---|---|---|---|
| 112 | | 1H NMR (400 MHz, DMSO-d6) δ 9.27-9.21 (m, 2H), 8.18 (d, J = 2.08 Hz, 2H), 7.86 (d, J = 2.08 Hz, 1H), 7.84 (d, J = 2.28 Hz, 1H), 7.62-7.52 (m, 3H), 6.93-6.86 (m, 2H), 4.15-3.99 (m, 2H), 3.34 (t, J = 6.23 Hz, 2H), 2.56 (s, 3H) | 380 |
| 113 | | $^1$H NMR (400 MHz, DMSO-d6) δ 7.75 (d, J = 1.9 Hz, 1 H), 7.56 (d, J = 9.1 Hz, 2 H), 7.50-7.41 (m, 3 H), 6.88 (d, J = 8.5 Hz, 2 H), 4.02 (d, J = 7.1 Hz, 2 H), 2.50 (s, 6 H), 2.32 (s, 3 H) | 397 |
| 114 | | $^1$H NMR (400 MHz, DMSO-d6) δ 8.26 (s, 1H), 7.97 (d, J = 0.83 Hz, 1H), 7.92 (d, J = 2.08 Hz, 1H), 7.59 (dd, J = 2.08, 8.10 Hz, 1H), 7.56-7.51 (m, 2H), 7.35 (d, J = 8.31 Hz, 1H), 6.85 (d, J = 8.10 Hz, 2H), 3.90 (s, 3H), 3.57 (s, 2H), 2.52 (s, 3H) | 382 |
| 115 | | $^1$H NMR (400 MHz, DMSO-d6) δ 13.15-12.83 (m, 1H), 8.02 (d, J = 8.31 Hz, 2H), 7.98 (d, J = 8.31 Hz, 1H), 7.90-7.83 (m, 3H), 7.77 (d, J = 2.08 Hz, 1H), 7.56 (d, J = 8.93 Hz, 2H), 6.91 (d, J = 8.31 Hz, 2H), 4.29-3.89 (m, 2H), 2.51 (s, 3H) | 422 |

-continued

| Compound # | Formula | NMR | LCMS |
|---|---|---|---|
| 116 | | ¹H NMR (400 MHz, DMSO-d6) δ 8.38 (d, J = 2.14 Hz, 1H), 8.31 (dd, J = 2.29, 9.31 Hz, 1H), 8.03 (br. s., 2H), 7.94 (d, J = 8.24 Hz, 1H), 7.79-7.72 (m, 2H), 7.55 (d, J = 9.00 Hz, 2H), 7.02 (d, J = 9.16 Hz, 1H), 6.89 (d, J = 7.93 Hz, 2H), 4.33-3.84 (m, 2H), 3.34 (br. s., 2H), 2.48 (s, 3H) | 395 |
| 117 | | ¹H NMR (400 MHz, DMSO-d6) δ 8.25 (d, J = 2.29 Hz, 1H), 7.93-7.84 (m, 2H), 7.71-7.62 (m, 2H), 7.55 (d, J = 8.93 Hz, 2H), 6.87 (d, J = 7.06 Hz, 2H), 6.47 (d, J = 9.35 Hz, 1H), 4.33 (br. s., 2H), 3.49 (s, 3H), 3.32 (br. s., 2H), 2.47 (s, 3H) | 409 |
| 118 | | ¹H NMR (400 MHz, Acetone) δ 7.85 (s, 1 H), 7.67 (d, J = 8.2 Hz, 2 H), 7.63 (s, 1 H), 7.51 (d, J = 8.2 Hz, 2 H), 7.42-7.22 (m, 1 H), 6.28-6.08 (m, 1 H), 4.69 (m, 1 H), 3.94 (s, 3 H), 3.90 (m., 1 H), 3.37-3.23 (m., 1 H), 2.44 (s, 3 H), 2.17 (s, 3 H), 1.43-1.32 (m, 3 H) | 410 |
| 119 | | ¹H NMR (400 MHz, DMSO-d6) δ 8.22 (s, 1H), 7.92 (s, 1H), 7.80 (d, J = 8.31 Hz, 1H), 7.69 (d, J = 8.72 Hz, 2H), 7.62 (s, 1H), 7.56 (s, 1H), 7.02-6.91 (m, 2H), 6.76 (d, J = 8.52 Hz, 2H), 4.11-3.96 (m, 2H), 3.84 (s, 3H), 3.30 (br. s., 2H), 2.47 (s, 3H) | 400 |

-continued

| Compound # | Formula | NMR | LCMS |
|---|---|---|---|
| 120 | | ¹H NMR (400 MHz, DMSO-d6) δ 8.97-8.97 (m, 1 H), 8.24 (s, 1 H), 7.94 (s, 1 H), 7.82 (d, J = 8.3 Hz, 1 H), 7.70-7.55 (m, 4 H), 6.92 (br. s., 2 H), 4.29-3.94 (m, 2 H), 3.88 (s, 3 H), 3.32-3.24 (m, 2 H), 3.09 (s, 3 H), 2.47 (s, 3 H) | 435 |
| 121 | | ¹H NMR (400 MHz, DMSO-d6) δ 8.22 (s, 1 H), 7.92 (s, 1 H), 7.79 (d, J = 8.3 Hz, 1 H), 7.67-7.43 (m, 4 H), 6.96-6.74 (m, 2 H), 4.64-4.42 (m, 1 H), 3.83 (s, 3 H), 3.56 (m, 2 H), 2.44 (s, 3 H), 1.88-1.69 (m, 2 H), 0.91 (t, J = 7.5 Hz, 3 H) | 410 |
| 122 | | ¹H NMR (400 MHz, DMSO-d6) δ 8.23 (d, J = 2.5 Hz, 1 H), 7.9-7.82 (m, 2 H), 7.71-7.61 (m, 2 H), 7.54 (d, J = 8.3 Hz, 2 H), 6.87 (br. s., 2 H), 6.46 (d, J = 9.8 Hz, 1 H), 4.64-4.45 (m, 1 H), 3.67-3.57 (m, 2 H), 3.53-3.41 (s, 3 H), 2.45 (s, 3 H), 1.79 (dd, J = 7.3, 13.9 Hz, 2 H), 0.91 (t, J = 7.4 Hz, 3 H) | 437 |
| 123 | | ¹H NMR (400 MHz, DMSO-d₆) δ 8.30 (d, J = 2.5 Hz, 1 H), 7.85 (d, J = 8.3 Hz, 1 H), 7.74 (dd, J = 2.6, 8.6 Hz, 1 H), 7.66 (dd, J = 2.0, 8.4 Hz, 1H), 7.57 (d, J = 1.9 Hz, 1 H), 7.54 (d, J = 9.1 Hz, 2 H), 7.02-6.85 (m, 2 H), 6.51 (d, J = 8.7 Hz, 1 H), 6.15 (s, 2 H), 4.60-4.44 (m, 1 H), 3.69-3.55 (m, 1 H), 3.30 (s, 1 H), 2.47 (s, 3 H), 1.32 (d, J = 6.9 Hz, 3 H) | 408 |

| Compound # | Formula | NMR | LCMS |
|---|---|---|---|
| 124 | 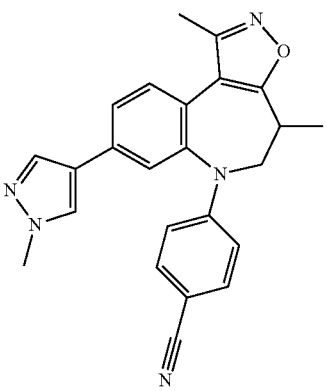 [SMILES: Cc1noc2c1-c1ccc(-c3cnn(C)c3)cc1N(c1ccc(C#N)cc1)CC2C] | ¹H NMR (400 MHz, DMSO-d₆) δ 8.23 (s, 1 H), 7.93 (s, 1 H), 7.80 (d, J = 8.3 Hz, 1 H), 7.63 (dd, J = 1.9, 8.3 Hz, 1 H), 7.58 (d, J = 1.9 Hz, 1 H), 7.55 (d, J = 8.9 Hz, 2 H), 6.91 (br. s., 2 H), 4.52 (d, J = 10.0 Hz, 1 H), 3.84 (s, 3 H), 3.69-3.54 (m, 1 H), 3.32-3.18 (m, 1 H), 2.46 (s, 3 H), 1.31 (d, J = 6.9 Hz, 3 H) | 396 |
| 125 | 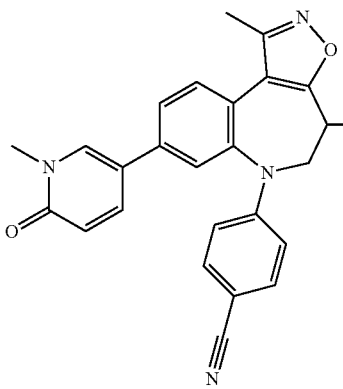 | ¹H NMR (400 MHz, DMSO-d₆) δ 8.25 (d, J = 2.7 Hz, 1 H), 7.92-7.83 (m, 2 H), 7.70-7.62 (m, 2 H), 7.55 (d, J = 9.1 Hz, 2 H), 6.92 (br. s., 2 H), 6.47 (d, J = 9.3 Hz, 1 H), 4.63-4.44 (m, 1 H), 3.71-3.54 (m, 1 H), 3.49 (s, 3 H), 3.29-3.19 (m, 1 H), 2.47 (s, 3 H), 1.32 (d, J = 6.9 Hz, 3 H) | 423 |

Example 5

Synthesis of 6-(4-cyanophenyl)-1-methyl-5,6-dihydro-4H-benzo[b]isoxazolo[4,5-d]azepine-9-carboxamide (126)

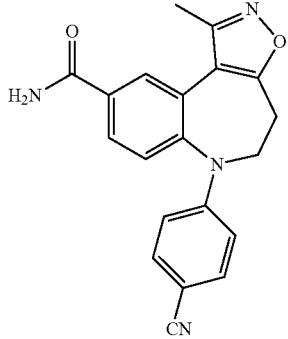 [SMILES: Cc1noc2c1-c1cc(C(N)=O)ccc1N(c1ccc(C#N)cc1)CC2]

Step 1: Synthesis of ethyl 6-(4-cyanophenyl)-1-methyl-5,6-dihydro-4H-benzo[b]isoxazolo[4,5-d]azepine-9-carboxylate

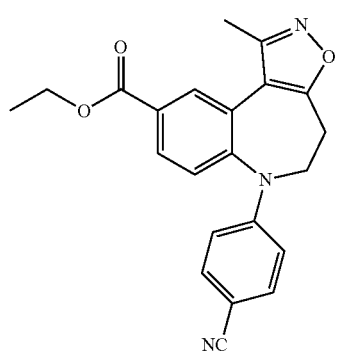 [SMILES: CCOC(=O)c1ccc2c(c1)-c1c(C)noc1CCN2c1ccc(C#N)cc1]

A disposable tube was charged with 4-(9-chloro-1-methyl-4H-benzo[b]isoxazolo[4,5-d]azepin-6(5H)-yl)benzonitrile (available following the general isoxazole azepine synthesis) (104 mg, 0.310 mmol), dcpp (18.96 mg, 0.031 mmol), PdOAc₂ (3.48 mg, 0.015 mmol), K₂CO₃ (86 mg, 0.619 mmol), and a stirbar before being evacuated and backfilled with CO (g) three times. DMF (1 mL) was added, followed by ethanol (36.2 μl, 0.619 mmol), and the mixture was stirred at 100° C. overnight. The reaction mixture was diluted with ethyl acetate, filtered, washed three times with brine, concentrated with Celite, and purified by silica gel chromatography (eluting with hexanes/ethyl acetate/isopropanol) to yield ethyl 6-(4-cyanophenyl)-1-methyl-5,6-dihydro-4H-benzo[b]isoxazolo[4,5-d]azepine-9-carboxylate (17 mg, 0.14 mmol) as a colorless oil. LC/MS: 374 [M+1].

Step 2: Synthesis of 6-(4-cyanophenyl)-1-methyl-5,6-dihydro-4H-benzo[b]isoxazolo[4,5-d]azepine-9-carboxylic acid

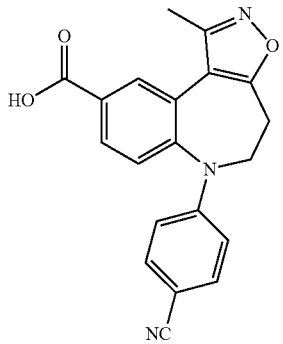 [SMILES: Cc1noc2c1-c1cc(C(=O)O)ccc1N(c1ccc(C#N)cc1)CC2]

A disposable tube was charged with ethyl 6-(4-cyanophenyl)-1-methyl-5,6-dihydro-4H-benzo[b]isoxazolo[4,5-d]azepine-9-carboxylate (20 mg, 0.054 mmol) and a stirbar. 1:1 THF:methanol (1 mL) was added, followed by sodium hydroxide (107 μl, 0.107 mmol), and the solution was stirred at 50° C. At 2 h, the mixture was diluted with dichloromethane, and the aqueous layer was acidified to pH 1 with 1 N HCl. The product was extracted three times from the aqueous layer, dried with sodium sulfate, and concentrated to yield 6-(4-cyanophenyl)-1-methyl-5,6-dihydro-4H-benzo[b]isoxazolo[4,5-d]azepine-9-carboxylic acid (yield not determined) as a milky film. LC/MS: 346 [M+1].

Step 3: Synthesis of 6-(4-cyanophenyl)-1-methyl-5,6-dihydro-4H-benzo[b]isoxazolo[4,5-d]azepine-9-carboxamide

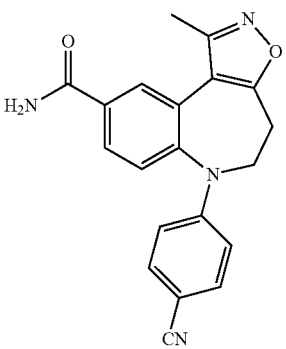 [SMILES: Cc1noc2c1-c1cc(C(N)=O)ccc1N(c1ccc(C#N)cc1)CC2]

A disposable reaction was charged with 6-(4-cyanophenyl)-1-methyl-5,6-dihydro-4H-benzo[b]isoxazolo[4,5-d]azepine-9-carboxylic acid (20 mg, 0.058 mmol), ammonium chloride (21.68 mg, 0.405 mmol), and a stirbar. DMF (5 mL, 0.01 M) was added, followed by Hunig's base (50.6 μl, 0.290 mmol), and the mixture was cooled to 0° C. for the addition of COMU (37.2 mg, 0.087 mmol). The mixture was stirred at room temperature overnight before being diluted with water and purified by reverse-phase HPLC (eluting with water/acetonitrile/0.1% TFA) to yield 6-(4-cyanophenyl)-1-methyl-5,6-dihydro-4H-benzo[b]isoxazolo[4,5-d]azepine-9-carboxamide (3 mg) as a white amorphous solid. ¹H NMR (400 MHz, DMSO-d6) δ 8.29 (d, J=1.87 Hz, 1H), 8.10 (br. s., 1H), 7.89 (dd, J=2.08, 8.31 Hz, 1H), 7.56 (d, J=8.93 Hz, 2H), 7.52 (br. s., 1H), 7.46 (d, J=8.31 Hz, 1H), 6.88 (d, J=8.93 Hz, 2H), 4.03 (br. s., 2H), 3.32 (s, 3H). m/z (ESI) 345 [M+H]⁺.

Example 6

Synthesis of 1,6-dimethyl-5,6-dihydro-4H-benzo[b]isoxazolo[4,5-d]azepine (127)

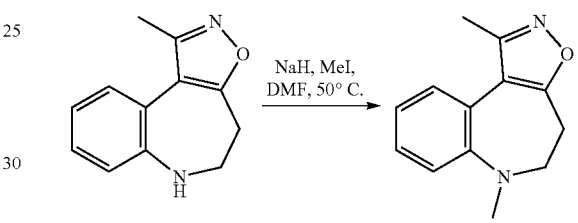

A round bottomed flask was charged with sodium hydride (25 mg, 0.625 mmol) and a stirbar. DMF (3 mL) was added, followed by 1-methyl-5,6-dihydro-4H-benzo[b]isoxazolo[4,5-d]azepine (45 mg, 0.225 mmol) in DMF (1 mL). The mixture was stirred at room temperature 1 h before the addition of excess iodomethane, and the mixture was heated to 50° C. overnight before being diluted with ethyl acetate, washed three times with brine, and dried with sodium sulfate. The residue was purified by silica gel chromatography (eluting with hexanes/ethyl acetate) to yield 1,6-dimethyl-5,6-dihydro-4H-benzo[b]isoxazolo[4,5-d]azepine (23 mg, 0.11 mmol) as a white amorphous solid. ¹H NMR (400 MHz, DMSO-d₆) δ 7.60 (dd, J=1.37, 7.78 Hz, 1H), 7.25-7.19 (m, 1H), 7.06 (d, J=8.24 Hz, 1H), 7.03-6.97 (m, 1H), 3.32 (s, 2H), 3.14 (s, 3H), 2.93 (s, 2H), 2.40 (s, 3H). LC/MS: 215 [M+1].

Example 7

Synthesis of 6-isopropyl-1-methyl-5,6-dihydro-4H-benzo[b]isoxazolo[4,5-d]azepine (128)

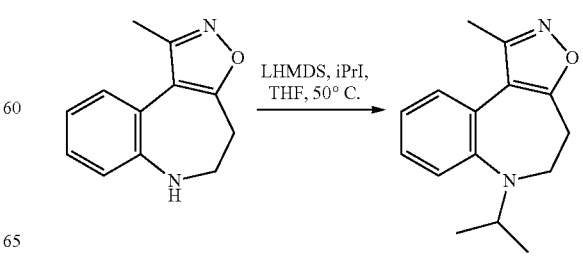

A disposable tube was charged with 1-methyl-5,6-dihydro-4H-benzo[b]isoxazolo[4,5-d]azepine (49 mg, 0.245 mmol) and a stirbar. THF (3 mL) was added and the solution was cooled to −78° C. for the addition of LHMDS (269 µl, 0.269 mmol) in THF. The solution was stirred at that temperature 15 min before being warmed to room temperature for the addition of 2-iodopropane (122 µl, 1.224 mmol). The mixture was stirred at 50° C. overnight before being concentrated in vacuo, purified by reverse phase HPLC (water/acetonitrile/0.1% TFA), and lyophilized to yield 6-isopropyl-1-methyl-5,6-dihydro-4H-benzo[b]isoxazolo[4,5-d]azepine (5 mg, 0.021 mmol) as an off-white amorphous solid. $^1$H NMR (complex due to slowly interconverting conformers) (400 MHz, DMSO-$d_6$) δ 7.59 (dd, J=1.49, 7.90 Hz, 1H), 7.55 (d, J=8.01 Hz, 1H), 7.22-7.15 (m, 1H), 7.08 (d, J=8.47 Hz, 1H), 7.03 (d, J=8.24 Hz, 1H), 6.95 (t, J=7.44 Hz, 1H), 6.87 (d, J=6.87 Hz, 1H), 6.82 (t, J=6.87 Hz, 1H), 3.84 (td, J=6.52, 13.05 Hz, 4H), 4.09-3.73 (m, 11H), 3.20-3.00 (m, 5H), 2.45 (s, 2H), 2.39 (s, 3H), 1.22 (d, J=6.64 Hz, 6H), 0.91 (d, J=6.87 Hz, 3H). LC/MS: 243 [M+1].

Example 8

Synthesis of 1-methyl-6-propyl-5,6-dihydro-4H-benzo[b]isoxazolo[4,5-d]azepine (129)

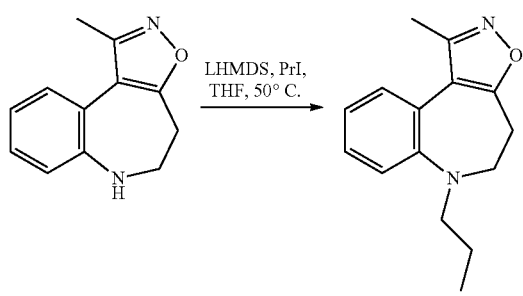 [SMILES: Cc1noc2c1-c1ccccc1NCC2 ; CCCN1CCc2onc(C)c2-c2ccccc21]

A disposable tube was charged with 1-methyl-5,6-dihydro-4H-benzo[b]isoxazolo[4,5-d]azepine (54 mg, 0.270 mmol) and a stirbar. THF (3 mL) was added, followed by LHMDS (337 µl, 0.337 mmol) in THF. The mixture was stirred at room temperature 1 h before the addition of 1-iodopropane (132 µl, 1.348 mmol), and then the mixture was heated to 50° C. 2 h. The reaction was quenched with methanol, diluted with ethyl acetate, washed three times with brine, dried with sodium sulfate, purified by silica gel chromatography, and lyophilized to yield 1-methyl-6-propyl-5,6-dihydro-4H-benzo[b]isoxazolo[4,5-d]azepine (30 mg, 0.124 mmol) as a colorless oil. $^1$H NMR (400 MHz, DMSO-$d_6$) δ 7.60 (dd, J=1.60, 7.78 Hz, 1H), 7.24-7.17 (m, 1H), 7.07 (d, J=7.10 Hz, 1H), 7.03-6.95 (m, 1H), 3.25-3.19 (m, 2H), 3.19-3.13 (m, 2H), 3.11-3.05 (m, 2H), 2.41 (s, 3H), 1.63-1.50 (m, 2H), 0.83 (t, J=7.32 Hz, 3H). LC/MS: 243 [M+1].

Example 9

Synthesis of 6-benzyl-1-methyl-5,6-dihydro-4H-benzo[b]isoxazolo[4,5-d]azepine (130)

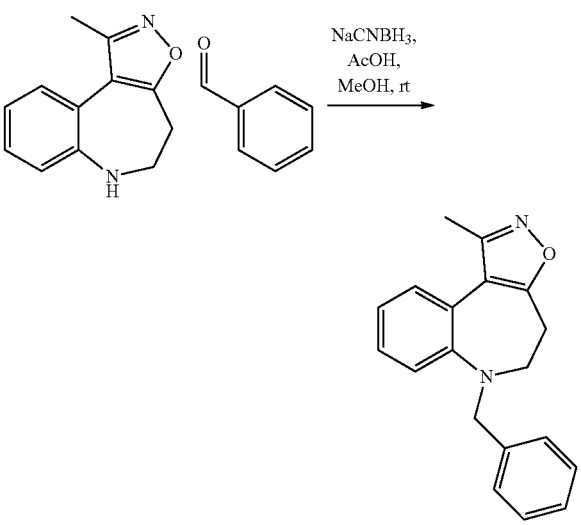

A round bottomed flask was charged with 1-methyl-5,6-dihydro-4H-benzo[b]isoxazolo[4,5-d]azepine (70 mg, 0.350 mmol) and a stirbar. Methanol (3.5 mL, 0.1 M) was added, followed by benzaldehyde (70.7 µl, 0.699 mmol) and acetic acid (40.0 µl, 0.699 mmol). The solution was stirred at room temperature 15 min before the addition of sodium cyanoborohydride (33.0 mg, 0.524 mmol). The reaction was stirred at room temperature 18 h before being concentrated with Celite and purified by silica gel chromatography (eluting with hexanes/ethyl acetate) to yield 6-benzyl-1-methyl-5,6-dihydro-4H-benzo[b]isoxazolo[4,5-d]azepine (19 mg, 0.065 mmol) as a white amorphous solid. $^1$H NMR (400 MHz, DMSO-$d_6$) δ 7.64 (d, J=7.8 Hz, 1H), 7.34-7.24 (m, 5H), 7.20-7.16 (m, 1H), 7.14-7.09 (m, 1H), 7.03-7.00 (m, 1H), 4.51 (s, 2H), 3.19 (t, J=5.7 Hz, 2H), 2.94-2.88 (m, 2H), 2.44 (s, 3H). LC/MS: 291 [M+1].

Example 10

Synthesis of 6-benzyl-1,7-dimethyl-5,6-dihydro-4H-benzo[b]isoxazolo[4,5-d]azepine (131)

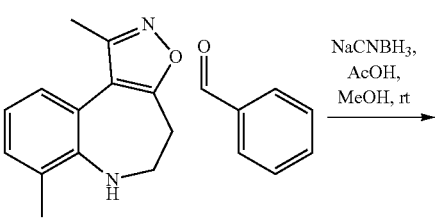

-continued

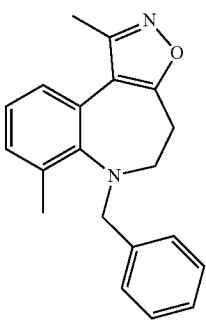

A round bottomed flask was charged with 1,7-dimethyl-5,6-dihydro-4H-benzo[b]isoxazolo[4,5-d]azepine (69 mg, 0.322 mmol) and a stirbar. Methanol (3.5 mL, 0.1 M) was added, followed by benzaldehyde (65.1 μl, 0.644 mmol) and acetic acid (55.3 μl, 0.966 mmol). The solution was stirred at room temperature 15 min before the addition of sodium cyanoborohydride (30.4 mg, 0.483 mmol). The reaction was stirred at room temperature 18 h before being concentrated with Celite and purified by silica gel chromatography (eluting with hexanes/ethyl acetate) to yield 6-benzyl-1,7-dimethyl-5,6-dihydro-4H-benzo[b]isoxazolo[4,5-d]azepine (46 mg, 0.151 mmol) as a white amorphous solid. $^1$H NMR (400 MHz, DMSO-d$_6$) δ 7.47 (dd, J=1.9, 7.0 Hz, 1H), 7.42-7.36 (m, 2H), 7.32 (t, J=7.3 Hz, 2H), 7.29-7.23 (m, 1H), 7.20-7.12 (m, 2H), 4.04 (br. s., 2H), 3.54-3.36 (m, 1H), 2.43 (s, 3H), 2.41 (s, 3H). LC/MS: 305 [M+1].

Example 11

Synthesis of (1-methyl-4H-benzo[b]isoxazolo[4,5-d]azepin-6(5H)-yl)(phenyl)methanone (132)

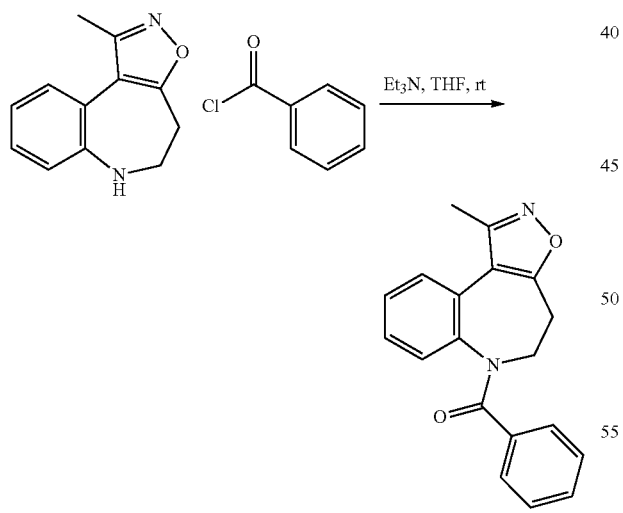

A disposable tube was charged with 1-methyl-5,6-dihydro-4H-benzo[b]isoxazolo[4,5-d]azepine (28 mg, 0.140 mmol) and a stirbar. THF (2.5 mL, 0.1 M) was added, followed by triethylamine (39.0 μl, 0.280 mmol) and benzoyl chloride (19.48 μl, 0.168 mmol), and the mixture was stirred at room temperature until the starting material was completely consumed, as judged by LC/MS. The mixture was concentrated with Celite, purified by silica gel chromatography (eluting with hexanes/ethyl acetate), and lyophilized to yield (1-methyl-4H-benzo[b]isoxazolo[4,5-d]azepin-6(5H)-yl)(phenyl)methanone as an off-white amorphous solid (39 mg, 0.128 mmol). $^1$H NMR (400 MHz, DMSO-d$_6$) δ 7.76 (dd, J=1.26, 7.90 Hz, 2H), 7.33-7.23 (m, 4H), 7.22-7.14 (m, 4H), 7.05 (t, J=7.44 Hz, 2H), 6.98 (d, J=7.32 Hz, 4H), 6.84 (d, J=7.78 Hz, 1H), 4.94 (dd, J=6.18, 13.50 Hz, 1H), 3.48-3.35 (m, 1H), 3.32-3.25 (m, 1H), 3.11 (dt, J=3.89, 13.28 Hz, 1H), 2.54 (s, 3H). LC/MS: 305 [M+1].

Example 12

Synthesis of 8-chloro-1-methyl-6-(phenylsulfonyl)-5,6-dihydro-4H-benzo[b]isoxazolo[4,5-d]azepine (133)

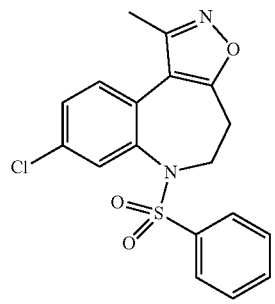 [SMILES: Cc1noc2c1-c1ccc(Cl)cc1N(S(=O)(=O)c1ccccc1)CC2]

To a round-bottomed flask charged with 8-chloro-1-methyl-5,6-dihydro-4H-benzo[b]isoxazolo[4,5-d]azepine (50 mg, 0.21 mmol) and pyridine (1 mL) was added benzensulfonyl chloride (42 mg, 0.24 mmol). The solution was stirred at room temperature for 2 h before concentrating. The crude residue was purified via Biotage (EtOAc/hex) to afford 8-chloro-1-methyl-6-(phenylsulfonyl)-5,6-dihydro-4H-benzo[b]isoxazolo[4,5-d]azepine (50 mg, 0.13 mmol). $^1$H NMR (400 MHz, DMSO-d6) δ 7.64-7.25 (m, 8H), 4.59-4.27 (m, 1H), 3.94-3.80 (m, 1H), 2.86-2.71 (m, 1H), 2.13 (s, 3H). m/z (ESI) 375 [M+H]$^+$.

Example 13

Synthesis of 2-(4-(6-(4-cyanophenyl)-1,4-dimethyl-5,6-dihydro-4H-benzo[b]isoxazolo[4,5-d]azepin-8-yl)-1H-pyrazol-1-yl)acetamide (134)

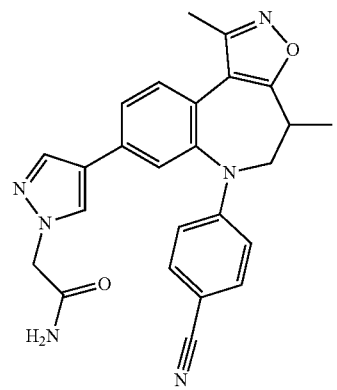 [SMILES: Cc1noc2c1-c1ccc(-c3cnn(CC(N)=O)c3)cc1N(c1ccc(C#N)cc1)CC2C]

To a solution of 2-(4-(6-(4-cyanophenyl)-1,4-dimethyl-5,6-dihydro-4H-benzo[b]isoxazolo[4,5-d]azepin-8-yl)-1H-pyrazol-1-yl)acetic acid (accessible via the general synthetic scheme) (108 mg, 0.246 mmol) in DMAc (3 mL) and DMF (1 mL) was sequentially added ammonium chloride (150 mg, 2.80 mmol) and N,N-diisopropylethylamine (0.400 mL, 2.290 mmol). To the heterogeneous mixture was added COMU (160 mg, 0.374 mmol) in portions. The reaction mixture turned orange in color. After 3 h, the mixture was partitioned between EtOAc and water. The aqueous phase was extracted with EtOAc (3×). The combined organic phases were washed with water (3×), washed with brine, dried over Na$_2$SO$_4$, and concentrated to give a light red oil. The oil was purified via Biotage (gradient elution, 10% EtOAc: 1% IPA: 89% Hexane to 99% EtOAc: 1% IPA) to yield white solids that were contaminated with a urea by-product (from the coupling reagent). The solids were subsequently diluted in EtOAc and washed H$_2$O(3×). The combined organic layers were dried over Na$_2$SO$_4$ and concentrated to deliver 2-(4-(6-(4-cyanophenyl)-1,4-dimethyl-5,6-dihydro-4H-benzo[b]isoxazolo[4,5-d]azepin-8-yl)-1H-pyrazol-1-yl)acetamide (73.8 mg, 0.168 mmol, 68.5% yield) as white solids. $^1$H NMR (400 MHz, DMSO-d6) δ 8.22 (s, 1H), 7.97 (d, J=0.62 Hz, 1H), 7.81 (d, J=8.31 Hz, 1H), 7.65 (dd, J=1.97, 8.21 Hz, 1H), 7.61 (d, J=1.87 Hz, 1H), 7.55 (d, J=9.14 Hz, 2H), 7.52 (br. s., 1H), 7.28 (s, 1H), 6.92 (br. s., 2H), 4.75 (s, 2H), 4.44-4.61 (m, 1H), 3.61 (dd, J=6.13, 12.57 Hz, 1H), 3.30 (s, 1H), 2.47 (s, 3H), 1.32 (d, J=6.86 Hz, 3H) m/z (ESI) 439 [M+H]$^+$.

Example 14

Synthesis of 4-(1-methyl-8-(1-methyl-1H-pyrazol-4-yl)-5-oxo-4H-benzo[b]isoxazolo[4,5-d]azepin-6(5H)-yl)benzonitrile (135)

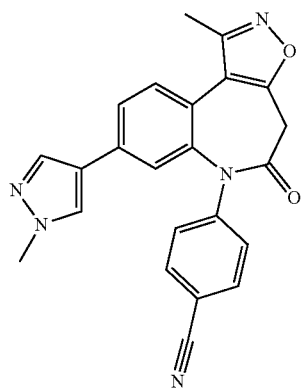 [SMILES: Cc1noc2c1-c1ccc(-c3cnn(C)c3)cc1N(c1ccc(C#N)cc1)C(=O)C2]

Step 1: Synthesis of Ethyl 2-(3-methylisoxazol-5-yl)acetate

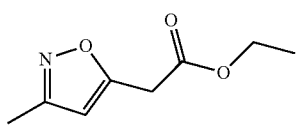

To a solution of 2-(3-methylisoxazol-5-yl)acetic acid (15.3 g, 108 mmol) in ethanol (350 mL) was added concentrated H$_2$SO$_4$ (1.20 mL, 22.51 mmol). The reaction mixture was stirred at room temperature. After 48 h, the brown solution was concentrated in vacuo to give a dark brown oil. The oil was filtered over a plug of silica (50 g) and the product was eluted with 40% Et$_2$O: 60% Hexane (400 mL) to yield ethyl 2-(3-methylisoxazol-5-yl)acetate (17.8 g, 105 mmol, 97% yield) as a clear oil. m/z (ESI) 170 [M+H]$^+$.

Step 2: Synthesis of ethyl 2-(4-bromo-3-methylisoxazol-5-yl)acetate

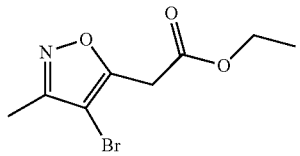

To a round-bottomed flask was added ethyl 2-(3-methylisoxazol-5-yl)acetate (3.77 g, 22.28 mmol), DMF (12 mL), and NBS (5.16 g, 29.0 mmol). The solution was stirred at room temperature overnight. The reaction was quenched via addition of a saturated solution of sodium thiosulfate. The orange solution quickly became yellow and biphasic. Acetonitrile was added (~10 mL) until the solution was homogeneous and the reaction stirred at room temperature for 0.5 h. The solution was diluted with water and EtOAc before the layers were separated. The aqueous layer was extracted with EtOAc and the combined organics layer was washed with water, brine, dried over Na$_2$SO$_4$, filtered, and concentrated. The crude residue was purified via Biotage (100 g, 5% EtOAc/hex to 20% EtOAc/hex) to afford ethyl 2-(4-bromo-3-methylisoxazol-5-yl)acetate (5.10 g, 20.56 mmol, 92% yield). m/z (ESI) 248, 250 [M+H]$^+$.

Step 3: Synthesis of 5-chloro-2-(4,4,5,5-tetramethyl-1,3,2-dioxaborolan-2-yl)aniline

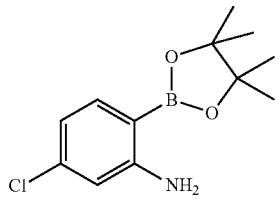 [SMILES: CC1(C)OB(c2ccc(Cl)cc2N)OC1(C)C]

To a round bottomed flask was added PdCl$_2$(dppf)-CH$_2$Cl$_2$ adduct (1.347 g, 1.650 mmol), KOAc (6.48 g, 66.0 mmol), bis(pinacolato)diboron (12.57 g, 49.5 mmol), 2-bromo-5-chloroaniline (6.81 g, 33 mmol), and DMSO (100 mL). The solution was evacuated/backfilled with N$_2$ (3×) before heating to 85° C. overnight. The solution was cooled to room temperature and diluted with MTBE and water. The solution was filtered and the layers were separated. The aqueous phase was extracted with MTBE and the combined organics layer was washed with water, brine, dried over Na$_2$SO$_4$, filtered, and concentrated. The crude residue was purified via Biotage to afford 5-chloro-2-(4,4,5,5-tetramethyl-1,3,2-dioxaborolan-2-yl)aniline (8.06 g, 31.8 mmol, 96% yield). m/z (ESI) 254 [M+H]$^+$.

Step 4: Synthesis of ethyl 2-(4-(2-amino-4-chlorophenyl)-3-methylisoxazol-5-yl)acetate

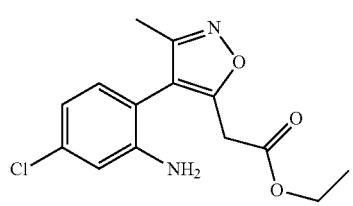 [SMILES: CCOC(=O)Cc1onc(C)c1-c1ccc(Cl)cc1N]

To a round bottomed flask was added tri-tert-butylphosphonium tetrafluoroborate (230 mg, 0.793 mmol), K$_3$PO$_4$ (6.1 g, 26.5 mmol), Pd$_2$(dba)$_3$ (301 mg, 0.329 mmol), and 5-chloro-2-(4,4,5,5-tetramethyl-1,3,2-dioxaborolan-2-yl)aniline (4.2 g, 16.57 mmol). To this flask was added dioxane (100 mL), water (5 mL), and ethyl 2-(4-bromo-3-methylisoxazol-5-yl)acetate (3.42 g, 13.80 mmol). The reaction was evacuated/backfilled with N$_2$ (3×) before heating to 80° C. for 2 h. The reaction was cooled to room temperature and diluted with EtOAc. The reaction was filtered and the filtrate was concentrated. The crude residue was purified via Biotage (EtOAc/hex) to afford ethyl 2-(4-(2-amino-4-chlorophenyl)-3-methylisoxazol-5-yl)acetate (2.243 g, 7.61 mmol, 55% yield). m/z (ESI) 295 [M+H]$^+$.

Step 5: Synthesis of 8-chloro-1-methyl-4H-benzo[b]isoxazolo[4,5-d]azepin-5(6H)-one

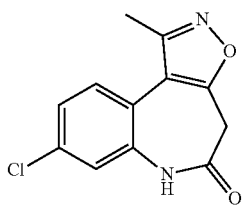 [SMILES: Cc1noc2c1-c1ccc(Cl)cc1NC(=O)C2]

To a resealable vial was added ethyl 2-(4-(2-amino-4-chlorophenyl)-3-methylisoxazol-5-yl)acetate (420 mg, 1.425 mmol), EtOH (7 mL), and HCl (1.06 mL, 4.28 mmol). The solution was stirred at room temperature for 1 h before being heated to 80° C. for 2 days. The solution was cooled to room temperature and concentrated. The crude residue was purified via Biotage (EtOAc/hex) to afford 8-chloro-1-methyl-4H-benzo[b]isoxazolo[4,5-d]azepin-5(6H)-one (169 mg, 0.680 mmol, 48% yield). m/z (ESI) 249 [M+H]$^+$.

Step 6: Synthesis of 4-(8-chloro-1-methyl-5-oxo-4H-benzo[b]isoxazolo[4,5-d]azepin-6(5H)-yl)benzonitrile

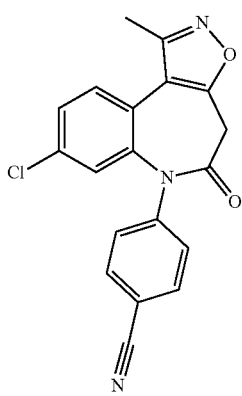 [SMILES: Cc1noc2c1-c1ccc(Cl)cc1N(c1ccc(C#N)cc1)C(=O)C2]

To a resealable vial was added 4-iodobenzonitrile (138 mg, 0.603 mmol), K$_3$PO$_4$ (185 mg, 0.804 mmol), CuI (7.66 mg, 0.040 mmol), and 8-chloro-1-methyl-4H-benzo[b]isoxazolo[4,5-d]azepin-5(6H)-one (100 mg, 0.402 mmol) before the vial was sealed. The vial was evacuated/backfilled with N$_2$ (3×) before addition of dioxane (1 mL) and trans-1,2-diaminocyclohexane (9.67 µl, 0.080 mmol). The solution was heated to 80° C. for 4 h before heating to 110° C. for 1 h. The solution was cooled to room temperature and concentrated. The crude residue was purified via Biotage (10 g, EtOAc/hex) to afford 4-(8-chloro-1-methyl-5-oxo-4H-benzo[b]isoxazolo[4,5-d]azepin-6(5H)-yl)benzonitrile (30.9 mg, 0.088 mmol, 22% yield). m/z (ESI) 350 [M+H]$^+$.

Step 7: Synthesis of 4-(1-methyl-8-(1-methyl-1H-pyrazol-4-yl)-5-oxo-4H-benzo[b]isoxazolo[4,5-d]azepin-6(5H)-yl)benzonitrile

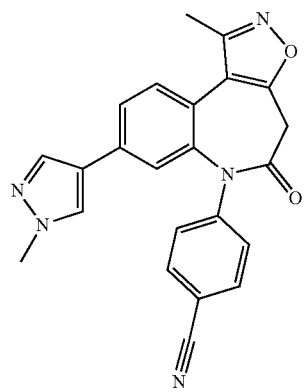

To a resealable vial was added tri-tert-butylphosphonium tetrafluoroborate (3.08 mg, 10.60 µmol), 1-methyl-4-(4,4,5,5-tetramethyl-1,3,2-dioxaborolan-2-yl)-1H-pyrazole (36.8 mg, 0.177 mmol), K$_3$PO$_4$ (40.7 mg, 0.177 mmol), and Pd$_2$(dba)$_3$ (4.04 mg, 4.42 µmol) before the vial was sealed. This vial was evacuated/backfilled with N$_2$ before addition of 4-(8-chloro-1-methyl-5-oxo-4H-benzo[b]isoxazolo[4,5-d]azepin-6(5H)-yl)benzonitrile (30.9 mg, 0.088 mmol) dissolved in Dioxane (1 ml) and addition of water (50 uL). This solution was evacuated/backfilled with N$_2$ (3×) before heating to 110° C. for 1 h. The reaction was cooled to room temperature and diluted with EtOAc. The solids were filtered off and the filtrate concentrated. The crude residue was purified via Biotage to afford 4-(1-methyl-8-(1-methyl-1H-pyrazol-4-yl)-5-oxo-4H-benzo[b]isoxazolo[4,5-d]azepin-6(5H)-yl)benzonitrile. $^1$H NMR (400 MHz, DMSO-d6) δ 8.03 (s, 1H), 7.83-7.89 (m, 2H), 7.74 (d, J=0.62 Hz, 1H), 7.72 (d, J=8.31 Hz, 1H), 7.58 (dd, J=1.77, 8.21 Hz, 1H), 7.32-7.38 (m, 2H), 7.08 (d, J=1.66 Hz, 1H), 3.94 (br. s., 2H), 3.81 (s, 3H), 2.58 (s, 3H). m/z (ESI) 396 [M+H]$^+$.

Example 16

Synthesis of 6-(4-chlorophenyl)-1-methyl-5,6-dihydro-4H-benzo[b]isoxazolo[4,3-d]azepine (136)

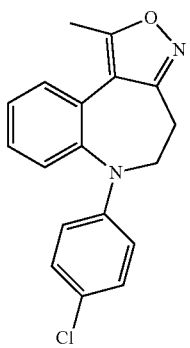 [SMILES: Cc1onc2c1-c1ccccc1N(c1ccc(Cl)cc1)CC2]

Step 1: Synthesis of 2-(5-methylisoxazol-3-yl)acetonitrile

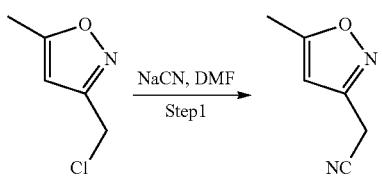

A mixture of 3-(chloromethyl)-5-methylisoxazole (10 g, 76 mmol) and sodium cyanide (5 g, 102 mmol) in dimethyl sulfoxide (60 mL) was stirred at ambient temperature for 16 hours. The mixture was diluted with water (60 mL) and extracted with ethyl acetate (3×100 mL). The combined organics layer was washed with water (50 mL) and brine (50 mL), dried over anhydrous sodium sulfate and filtered. The filtrate was concentrated to give 2-(5-methylisoxazol-3-yl)acetonitrile as a yellow oil which was used in the next step without further purification (10 g). $^1$H NMR (300 MHz, CDCl$_3$): δ 6.10 (s, 1H), 3.77 (s, 2H), 2.45 (s, 3H). LRMS (M+H$^+$) m/z: calcd 122.05. found 122.

Step 2: Synthesis of 2-(4-bromo-5-methylisoxazol-3-yl)acetonitrile

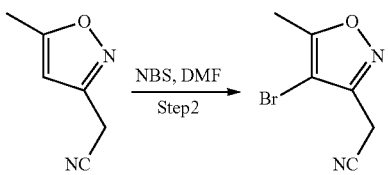

A mixture of 2-(5-methylisoxazol-3-yl)acetonitrile (10 g, 82 mmol) and N-bromosuccinimide (14.5 g, 82 mmol) in N,N-dimethylformamide (100 mL) was stirred at 30° C. for 24 hours. After cooling, the mixture was diluted with water (100 mL) and extracted with ethyl acetate (3×100 mL). The combined organics layer was washed with water (50 mL), brine (50 mL), dried over anhydrous sodium sulfate and filtered. The filtrate was concentrated to give a residue which was purified by column chromatography (silica-gel, petroleum ether: ethyl acetate=5:1) to afford 2-(4-bromo-5-methylisoxazol-3-yl)acetonitrile as a colorless oil (1 g, 6% yield). $^1$H NMR (300 MHz, CDCl$_3$): δ 3.71 (s, 2H), 2.41 (s, 3H). LRMS (M+H$^+$) m/z: calcd 199.96. found 200.

Step 3: Synthesis of tert-butyl 2-(3-(cyanomethyl)-5-methylisoxazol-4-yl)phenylcarbamate

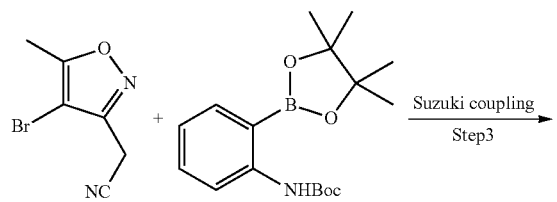

A mixture of 2-(4-bromo-5-methylisoxazol-3-yl)acetonitrile (1 g, 5 mmol), tert-butyl 2-(4,4,5,5-tetramethyl-1,3,2-dioxaborolan-2-yl)phenylcarbamate (2.4 g, 7.5 mmol), 1,1'-bis(diphenylphosphino)ferrocene-palladium(II)dichloride (36.6 mg, 0.05 mmol), cesium carbonate (3.3 g, 10 mmol), water (4 mL) and toluene (20 mL) was heated in a microwave at 130° C. for 1 hour. The mixture was filtered and the filter cake was washed with ethyl acetate (50 mL). The combined organics layer was dried over anhydrous sodium sulfate and filtered. The filtrate was concentrated to give a residue which was purified by column chromatography (silica-gel, petroleum ether: ethyl acetate=4:1) to give tert-butyl 2-(3-(cyanomethyl)-5-methylisoxazol-4-yl)phenylcarbamate as a brown solid (500 mg, 32% yield). $^1$H NMR (300 MHz, CDCl$_3$): δ 8.05 (d, J=3 Hz, 1H), 7.46-7.41 (m, 1H), 7.20-7.10 (m, 2H), 6.06 (s, 1H), 3.62 (d, J=3 Hz, 2H), 2.35 (s, 3H), 1.47 (s, 9H). LRMS (M+H$^+$) m/z: calcd 313.14. found 313.

Step 4: Synthesis of 2-(4-(2-(tert-butoxycarbonylamino)phenyl)-5-methylisoxazol-3-yl)acetic acid

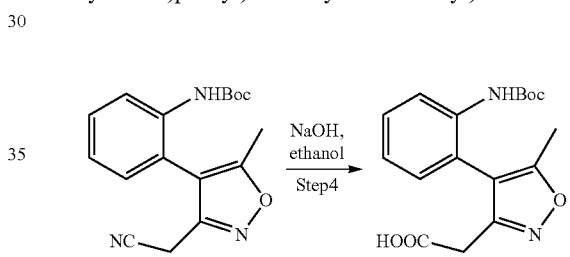

A mixture of tert-butyl 2-(3-(cyanomethyl)-5-methylisoxazol-4-yl)phenylcarbamate (450 mg, 1.4 mmol), sodium hydroxide (112 mg, 2.8 mmol), water (1 mL) and ethanol (5 mL) was refluxed for 3 hours. The solvent was removed in vacuo and the residue was neutralized with 1 N HCl. The mixture was extracted with ethyl acetate (5×30 mL). The combined organics layer was washed with water (50 mL), brine (50 mL), dried over anhydrous sodium sulfate and filtered. The filtrate was concentrated to give 24442-(tert-butoxycarbonylamino)phenyl)-5-methylisoxazol-3-yl)acetic acid as a white solid which was used in the next step without further purification (320 mg, 67% yield). LRMS (M+H$^+$) m/z: calcd 332.14. found 332.

Step 5: Synthesis of methyl 2-(4-(2-(tert-butoxycarbonylamino)phenyl)-5-methylisoxazol-3-yl)acetate

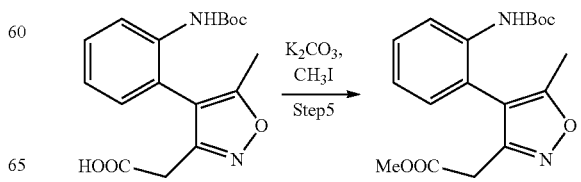

To a mixture of 2-(4-(2-(tert-butoxycarbonylamino)phenyl)-5-methylisoxazol-3-yl)acetic acid (320 mg, 0.9 mmol) and potassium carbonate (265 mg, 1.9 mmol) in N,N-dimethylformamide (5 mL) was added iodomethane (142 mg, 1 mmol). After addition, the mixture was stirred at ambient temperature for 10 hours. The mixture was diluted with water (30 mL) and extracted with ethyl acetate (5×30 mL). The combined organics layer was washed with water (50 mL), brine (50 mL), dried over anhydrous sodium sulfate and filtered. The filtrate was concentrated to give a residue which was purified by column chromatography (silica-gel, petroleum ether: ethyl acetate=6:1) to give 2-(4-(2-(tert-butoxycarbonylamino)phenyl)-5-methylisoxazol-3-yl)acetate as an off-white solid (250 mg, 75% yield). $^1$H NMR (300 MHz, CDCl$_3$): δ 8.02 (d, J=6 Hz, 1H), 7.41-7.25 (m, 1H), 7.12-6.33 (m, 2H), 6.33 (s, 1H), 3.66-3.56 (m, 3H), 3.56 (s, 1H), 2.28 (s, 3H), 1.49 (s, 9H). LRMS (M+H$^+$) m/z: calcd 346.15. found 346.

Step 6: Synthesis of methyl 2-(4-(2-aminophenyl)-5-methylisoxazol-3-yl)acetate

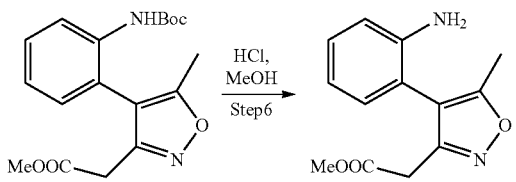 [SMILES: COC(=O)Cc1noc(C)c1-c1ccccc1NC(=O)OC(C)(C)C ; COC(=O)Cc1noc(C)c1-c1ccccc1N]

A mixture of methyl 2-(4-(2-(tert-butoxycarbonylamino)phenyl)-5-methylisoxazol-3-yl)acetate (250 mg, 0.72 mmol) in hydrochloric acid/methanol (2 N) (10 mL) was stirred at ambient temperature for 16 hours. The solvent was removed in vacuo and the residue was dissolved in water (3 mL). The solution was neutralized with 1 N sodium hydroxide and extracted with dichloromethane (3×30 mL). The combined organics layer was washed with water (50 mL), brine (50 mL), dried over anhydrous sodium sulfate and filtered. The filtrate was concentrated to give methyl 2-(4-(2-aminophenyl)-5-methylisoxazol-3-yl)acetate as a yellow solid which was used in the next step without further purification (180 mg). LRMS (M+H$^+$) m/z: calcd 246.1. found 246.

Step 7: Synthesis of 1-methyl-4H-benzo[b]isoxazolo[4,3-d]azepin-5(6H)-one

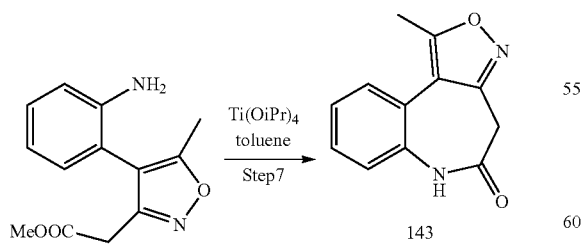

A mixture of methyl 2-(4-(2-aminophenyl)-5-methylisoxazol-3-yl)acetate (180 mg, 0.73 mmol) and Ti(OiPr)$_4$ (415 g, 1.46 mmol) in t (10 mL) was heated at 80° C. for 16 hours. The mixture was cooled to room temperature before addition of water (1 mL). The mixture was filtered and the filter cake was washed with CH$_2$Cl$_2$ (5×10 mL). The solvent was evaporated to dryness and the residue was purified by column chromatography (silica-gel, petroleum ether: ethyl acetate=5:1) to give 1-methyl-4H-benzo[b]isoxazolo[4,3-d]azepin-5(6H)-one as a colorless oil (90 mg, 58% yield). $^1$H NMR (300 MHz, CDCl$_3$): δ 8.15 (s, 1H), 7.45-7.26 (m, 3H), 7.14-7.11 (m, 1H), 3.72 (s, 2H), 2.63 (s, 3H). LRMS (M+H$^+$) m/z: calcd 214.07. found 214.

Step 8: Synthesis of 1-methyl-5,6-dihydro-4H-benzo[b]isoxazolo[4,3-d]azepine (143)

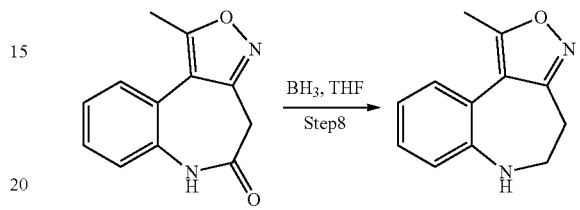

To a solution of 1-methyl-4H-benzo[b]isoxazolo[4,3-d]azepin-5(6H)-one (90 mg, 0.42 mmol) in THF (10 mL) was added borane tetrahydrofuran complex (1 N, 4.2 mL, 4.2 mmol) under nitrogen atmosphere at ambient temperature. After addition, the mixture was stirred at ambient temperature for 30 minutes. To the mixture was added dropwise 0.3 N hydrochloric acid. The mixture was stirred for 20 min and extracted with ethyl acetate (3×30 mL). The combined organics layer was washed with water (10 mL), brine (10 mL), dried over anhydrous sodium sulfate and filtered. The filtrate was concentrated to give a residue which was purified by column chromatography (silica-gel, petroleum ether: ethyl acetate=2:1) to give 1-methyl-5,6-dihydro-4H-benzo[b]isoxazolo[4,3-d]azepine as a white solid (75 mg, 89% yield). $^1$H NMR (300 MHz, CDCl$_3$): δ 7.38-7.35 (m, 1H), 7.14-7.09 (m, 1H), 6.95-6.92 (m, 1H), 6.78 (d, J=6 Hz, 2H), 3.53-3.49 (m, 2H), 3.13-3.09 (m, 2H), 2.63 (s, 3H). LRMS (M+H$^+$) m/z: calcd 200.09. found 200.

Step 9: Synthesis of 6-(4-chlorophenyl)-1-methyl-5,6-dihydro-4H-benzo[b]isoxazolo[4,3-d]azepine

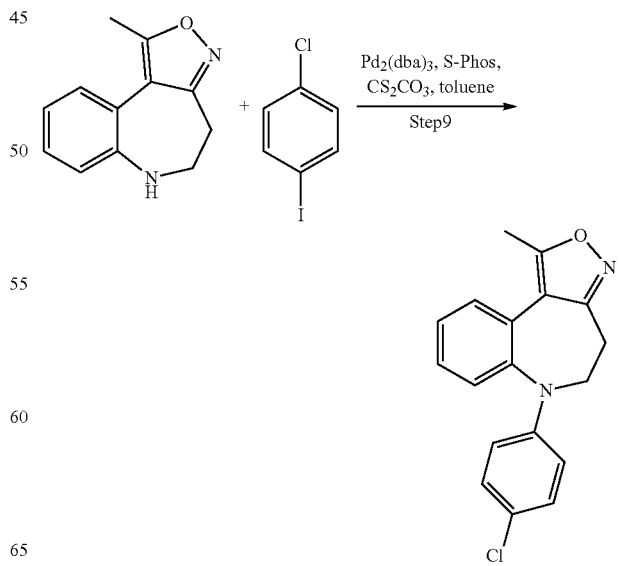

A mixture of 1-methyl-5,6-dihydro-4H-benzo[b]isoxazolo[4,3-d]azepine (20 mg, 0.1 mmol), tris(dibenzylideneacetone)dipalladium (9 mg, 0.01 mmol), 2-dicyclohexylphosphino-2',6'-dimethoxybiphenyl (S-Phos, CAS 657408-07-6, 8 mg, 0.02 mmol), cesium carbonate (65 mg, 0.2 mmol) and toluene (10 mL) was heated at 110° C. for 16 hours under a nitrogen atmosphere. The mixture was cooled to room temperature and filtered. The filter cake was washed with ethyl acetate (50 mL). The combined organics layer was dried over anhydrous sodium sulfate and filtered. The filtrate was concentrated to give a residue which was purified by column chromatography (silica-gel, petroleum ether:ethyl acetate=5:1) to give 6-(4-chlorophenyl)-1-methyl-5,6-dihydro-4H-benzo[b]isoxazolo[4,3-d]azepine as an off-white solid (10 mg, 32% yield). $^1$H NMR (300 MHz, DMSO-d$_6$): δ 7.53-7.50 (m, 1H), 7.34-7.27 (m, 3H), 7.09 (d, J=9 Hz, 2H), 6.62 (d, J=9 Hz, 2H), 3.98-3.94 (m, 2H), 3.22-3.18 (m, 2H), 2.63 (s, 3H). LRMS (M+H$^+$) m/z: calcd 310.09. found 310.

Example 17

Synthesis of 2-(6-(4-cyanophenyl)-1-methyl-8-(1-methyl-1H-pyrazol-4-yl)-5,6-dihydro-4H-benzo[b]isoxazolo[4,5-d]azepin-4-yl)acetamide (137) and 4-(4-(2-hydroxyethyl)-1-methyl-8-(1-methyl-1H-pyrazol-4-yl)-4H-benzo[b]isoxazolo[4,5-d]azepin-6(5H)-yl)benzonitrile (138)

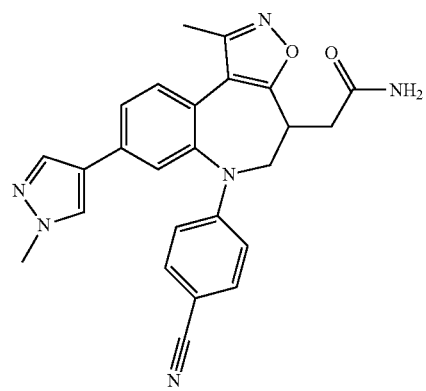

137

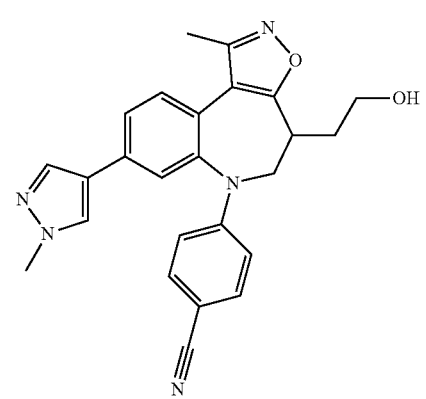

138

Step 1: Synthesis of tert-butyl 4-((2-bromo-5-chlorophenyl)amino)-3-(3-methylisoxazol-5-yl)-4-oxobutanoate

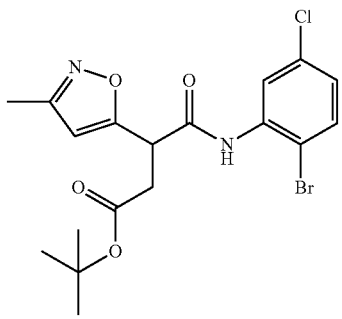 [SMILES: Cc1cc(C(CC(=O)OC(C)(C)C)C(=O)Nc2cc(Cl)ccc2Br)on1]

To a round bottomed flask was added 2-(3-methylisoxazol-5-yl)acetic acid (3.15 g, 22.32 mmol) and THF (60 mL) before the reaction was cooled to −78° C. To this solution was added nBuLi (19.64 ml, 49.1 mmol) and the solution stirred at −78° C. for 5 min before warming to 0° C. for 20 min. After 20 min, the solution was cooled to −78° C. and tert-butyl 2-bromoacetate (6.59 ml, 44.6 mmol) was added and the solution stirred for 1 h at −78° C. This solution was then quenched via the addition of sat. aq. NaHCO$_3$ and diluted with ether. The layers were separated and the aqueous washed with ether (1×). The ether layer was discarded and the aqueous was acidified with 1N HCl. The aqueous was extracted with EtOAc and the combined organics layer was washed with brine, dried over Na$_2$SO$_4$, filtered, and concentrated. The crude residue was then taken up in DMF (40 mL) and 2-bromo-5-chloroaniline (4.61 g, 22.32 mmol), EDC (6.42 g, 33.5 mmol), and 3H-[1,2,3]triazolo[4,5-b]pyridin-3-ol (3.34 g, 24.55 mmol) were added. The solution was stirred overnight before diluting with water and extracting with EtOAc. The combined organics layer was washed with water, brine, dried over Na$_2$SO$_4$, filtered, and concentrated. The crude residue was purified via Biotage (EtOAc/hex) to afford tert-butyl 4-(2-bromo-5-chlorophenylamino)-3-(3-methylisoxazol-5-yl)-4-oxobutanoate (5.878 g, 13.25 mmol, 59% yield). m/z (ESI) 443, 445 [M+H]$^+$.

Step 2: Synthesis of tert-butyl 4-(2-bromo-5-chlorophenylamino)-3-(3-methylisoxazol-5-yl)butanoate and 2-bromo-N-(4-tert-butoxy-2-(3-methylisoxazol-5-yl)butyl)-5-chloroaniline

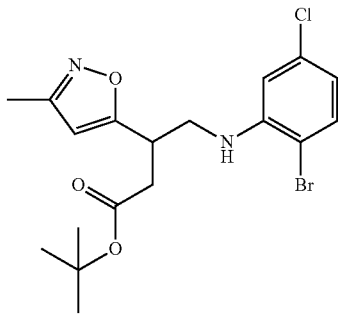

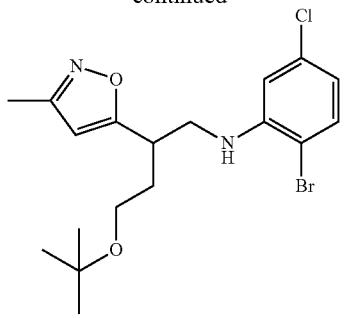

To a round bottomed flask was added tert-butyl 4-(2-bromo-5-chlorophenylamino)-3-(3-methylisoxazol-5-yl)-4-oxobutanoate (5.878 g, 13.25 mmol), THF (50 mL), and BH3.THF (26.5 ml, 26.5 mmol). The solution was then heated to reflux for 3 h before cooling to 0° C. and addition of MeOH (50 mL). The solution was stirred at 0° C. for 10 min before heating to reflux for 1 h. The solution was cooled to room temperature and concentrated. The crude residues was purified via Biotage (EtOAc/hex) to afford tert-butyl 4-(2-bromo-5-chlorophenylamino)-3-(3-methylisoxazol-5-yl)butanoate (m/z (ESI) 429, 431 [M+H]$^+$) and 2-bromo-N-(4-tert-butoxy-2-(3-methylisoxazol-5-yl)butyl)-5-chloroaniline as a ~1:1 mixture (m/z (ESI) 415, 417 [M+H]$^+$) (3.96 g).

Step 3: Synthesis of tert-butyl 2-(8-chloro-1-methyl-5,6-dihydro-4H-benzo[b]isoxazolo[4,5-d]azepin-4-yl)acetate and 4-(2-tert-butoxyethyl)-8-chloro-1-methyl-5,6-dihydro-4H-benzo[b]isoxazolo[4,5-d]azepine

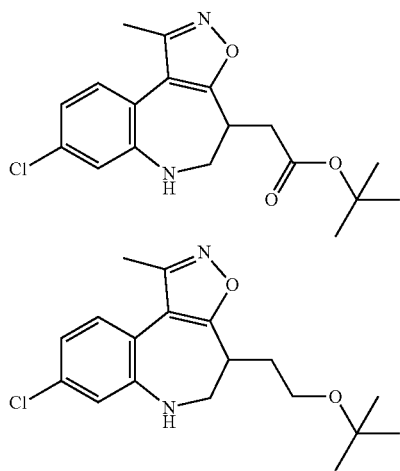

To a round bottomed flask was added palladium(II) chloride (40.9 mg, 0.230 mmol), KOAc (904 mg, 9.21 mmol), and tetrabutylammonium chloride (1280 mg, 4.61 mmol). The flask was evacuated/backfilled with N$_2$ (3×) before addition of a 1:1 mixture of 2-bromo-N-(4-tert-butoxy-2-(3-methylisoxazol-5-yl)butyl)-5-chloroaniline and tert-butyl 4-(2-bromo-5-chlorophenylamino)-3-(3-methylisoxazol-5-yl)butanoate (1.98 g, 4.61 mmol) dissolved in DMA (20 mL). The reaction was evacuated/backfilled with N$_2$ (3×) before heating to 130° C. overnight. The solution was cooled to room temperature, diluted with water and EtOAc, and the layers separated. The aqueous phase was extracted with EtOAc and the combined organics layer was washed with water, brine, dried over Na$_2$SO$_4$, filtered, and concentrated. The crude residue was purified via Biotage (EtOAc/hex) to afford a 1:1 mixture of tert-butyl 2-(8-chloro-1-methyl-5,6-dihydro-4H-benzo[b]isoxazolo[4,5-d]azepin-4-yl)acetate (m/z (ESI) 349 [M+H]$^+$) and 4-(2-tert-butoxyethyl)-8-chloro-1-methyl-5,6-dihydro-4H-benzo[b]isoxazolo[4,5-d]azepine (m/z (ESI) 335 [M+H]$^+$) (710 mg).

Step 4: Synthesis of tert-butyl 2-(8-chloro-6-(4-cyanophenyl)-1-methyl-5,6-dihydro-4H-benzo[b]isoxazolo[4,5-d]azepin-4-yl)acetate and 4-(4-(2-tert-butoxyethyl)-8-chloro-1-methyl-4H-benzo[b]isoxazolo[4,5-d]azepin-6(5H)-yl)benzonitrile

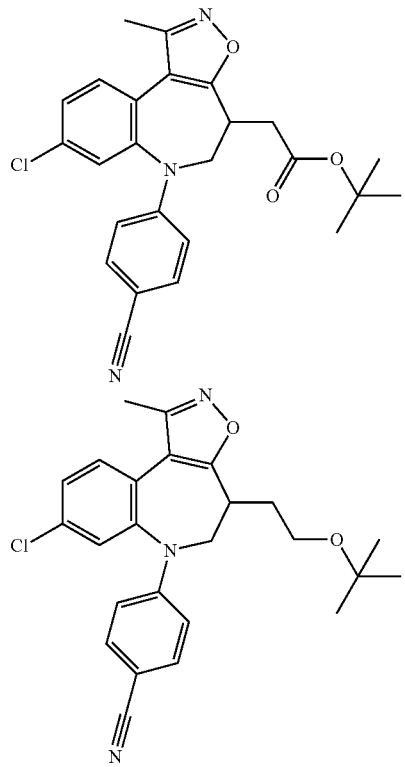

To a resealable vial was added Cs$_2$CO$_3$ (180 mg, 0.552 mmol), chloro(2-dicyclohexylphosphino-2',6'-di-i-propoxy-1,1'-biphenyl)[2-(2-aminoethylphenyl)]palladium(II) [CAS 1028206-60-1] (3.22 mg, 4.41 µmol), and 4-iodobenzonitrile (76 mg, 0.331 mmol) before the vial was sealed and evacuated/backfilled with N$_2$ (3×). To this vial was added a 1:1 mixture of 4-(2-tert-butoxyethyl)-8-chloro-1-methyl-5,6-dihydro-4H-benzo[b]isoxazolo[4,5-d]azepine and tert-butyl 2-(8-chloro-1-methyl-5,6-dihydro-4H-benzo[b]isoxazolo[4,5-d]azepin-4-yl)acetate (77 mg, 0.221 mmol) dissolved in dioxane (2 mL). The solution was evacuated/backfilled with N$_2$ (3×) before heating to 110° C. for 3 h. The solution was cooled to room temperature and diluted with EtOAc. The solution was filtered and the filtrate concentrated. The crude residue was purified via Biotage (EtOAc/hex) to afford a ~1:1 mixture of tert-butyl 2-(8-chloro-6-(4-cyanophenyl)-1-methyl-5,6-dihydro-4H-benzo[b]isoxazolo[4,5-d]azepin-4-yl)acetate (m/z (ESI) 450 [M+H]$^+$) and 4-(4-(2-tert-butoxyethyl)-8-chloro-1-methyl-4H-benzo[b]
isoxazolo[4,5-d]azepin-6(5H)-yl)benzonitrile (m/z (ESI)
436 [M+H]⁺) (79.1 mg).

Step 5: Synthesis of tert-butyl 2-(6-(4-cyanophe-
nyl)-1-methyl-8-(1-methyl-1H-pyrazol-4-yl)-5,6-
dihydro-4H-benzo[b]isoxazolo[4,5-d]azepin-4-yl)
acetate and 4-(4-(2-tert-butoxyethyl)-1-methyl-8-(1-
methyl-1H-pyrazol-4-yl)-4H-benzo[b]isoxazolo[4,5-
d]azepin-6(5H)-yl)benzonitrile

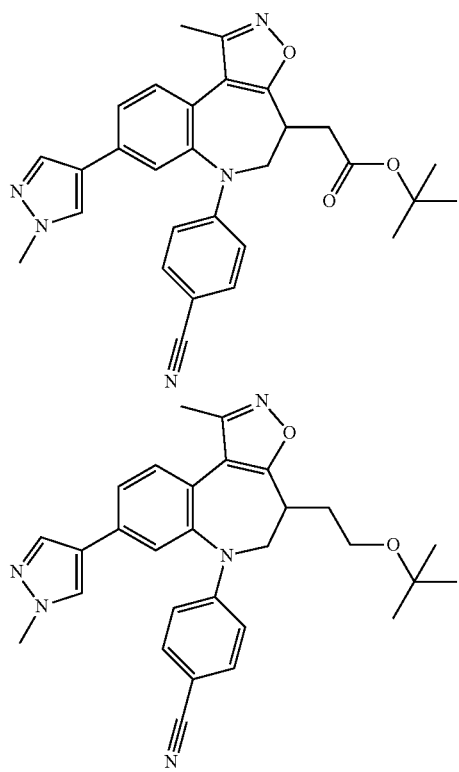

To a resealable vial was added K₃PO₄ (119 mg, 0.516 mmol), tri-tert-butylphosphonium tetrafluoroborate (8.98 mg, 0.031 mmol), Pd₂(dba)₃ (11.80 mg, 0.013 mmol), and 1-methyl-4-(4,4,5,5-tetramethyl-1,3,2-dioxaborolan-2-yl)-1H-pyrazole (107 mg, 0.516 mmol). The vial was sealed and evacuated/backfilled with N₂ (3×) before addition of a 1:1 mixture of tert-butyl 2-(8-chloro-6-(4-cyanophenyl)-1-methyl-5,6-dihydro-4H-benzo[b]isoxazolo[4,5-d]azepin-4-yl)acetate and 4-(4-(2-tert-butoxyethyl)-8-chloro-1-methyl-4H-benzo[b]isoxazolo[4,5-d]azepin-6(5H)-yl)benzonitrile (116 mg, 0.258 mmol) dissolved in dioxane (2 mL). The vial was evacuated/backfilled with N₂ (3×) before heating to 110° C. for 1.5 h. The reaction was then cooled to room temperature, diluted with EtOAc, and filtered. The filtrate was concentrated and the crude residue was purified via Biotage (EtOAc/hex) to afford a 1:1 mixture of tert-butyl 2-(6-(4-cyanophenyl)-1-methyl-8-(1-methyl-1H-pyrazol-4-yl)-5,6-dihydro-4H-benzo[b]isoxazolo[4,5-d]azepin-4-yl) acetate (m/z (ESI) 496 [M+H]⁺) and 4-(4-(2-tert-butoxyethyl)-1-methyl-8-(1-methyl-1H-pyrazol-4-yl)-4H-benzo[b]isoxazolo[4,5-d]azepin-6(5H)-yl)benzonitrile (m/z (ESI) 482 [M+H]⁺) (96 mg).

Step 6: Synthesis of 2-(6-(4-cyanophenyl)-1-
methyl-8-(1-methyl-1H-pyrazol-4-yl)-5,6-dihydro-
4H-benzo[b]isoxazolo[4,5-d]azepin-4-yl)acetamide
and 4-(4-(2-hydroxyethyl)-1-methyl-8-(1-methyl-
1H-pyrazol-4-yl)-4H-benzo[b]isoxazolo[4,5-d]aze-
pin-6(5H)-yl)benzonitrile

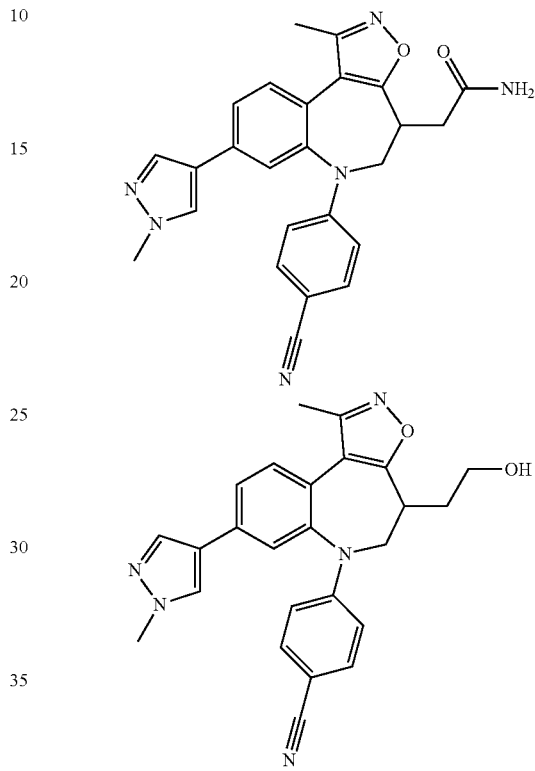

To a round-bottomed flask was added a mixture of 4-(4-(2-tert-butoxyethyl)-1-methyl-8-(1-methyl-1H-pyrazol-4-yl)-4H-benzo[b]isoxazolo[4,5-d]azepin-6(5H)-yl)benzonitrile and tert-butyl 2-(6-(4-cyanophenyl)-1-methyl-8-(1-methyl-1H-pyrazol-4-yl)-5,6-dihydro-4H-benzo[b]isoxazolo[4,5-d]azepin-4-yl)acetate (96 mg, 0.194 mmol), CH₂Cl₂ (2 mL), and TFA (1 mL). The solution was stirred at room temperature for 1 h before concentrating. To the crude residue was added ammonium chloride (62.2 mg, 1.162 mmol), DMF (2 mL), N,N-diisopropylethylamine (0.271 mL, 1.550 mmol), and COMU (141 mg, 0.329 mmol). The solution was stirred at room temperature for 1 h before another portion of N,N-diisopropylethylamine (0.271 mL, 1.550 mmol) was added. The reaction was stirred for an additional 30 min before the solution was diluted with water and EtOAc. The layers were separated and the aqueous phase was extracted with EtOAc. The combined organics layer was washed with water, brine, dried over Na₂SO₄, filtered, and concentrated. The crude residue was purified via biotage (10 g, 10% (3:2 CH₂Cl₂:IPA): 90% hexanes to 60% (3:2 CH₂Cl₂:IPA): 40% hex) to afford 2-(6-(4-cyanophenyl)-1-methyl-8-(1-methyl-1H-pyrazol-4-yl)-5,6-dihydro-4H-benzo[b]isoxazolo[4,5-d]azepin-4-yl)acetamide (43.5 mg, 0.099 mmol, 51% yield). ¹H NMR (400 MHz, DMSO-d6) δ 8.23 (s, 1H), 7.93 (s, 1H), 7.81 (d, J=8.31 Hz, 1H), 7.64 (dd, J=1.87, 8.31 Hz, 1H), 7.53-7.61 (m, 3H), 7.44-7.51 (m, 1H), 6.99 (br. s., 1H), 6.85-6.95 (m, 2H), 4.54

(dd, J=6.02, 16.00 Hz, 1H), 3.86-3.95 (m, 1H), 3.84 (s, 3H), 3.36-3.49 (m, 1H), 2.71 (dd, J=4.15, 16.00 Hz, 1H), 2.47 (s, 3H), 2.44-2.49 (m, 1H). m/z (ESI) 439 [M+H]⁺.

Fractions containing the primary alcohol were concentrated and repurified via RP-HPLC to afford 4-(4-(2-hydroxyethyl)-1-methyl-8-(1-methyl-1H-pyrazol-4-yl)-4H-benzo[b]isoxazolo[4,5-d]azepin-6(5H)-yl)benzonitrile (18.6 mg, 0.044 mmol, 23% yield). ¹H NMR (400 MHz, DMSO-d6) δ 8.23 (s, 1H), 7.93 (s, 1H), 7.80 (d, J=8.10 Hz, 1H), 7.63 (d, J=8.10 Hz, 1H), 7.50-7.61 (m, 3H), 6.79-6.91 (m, 2H), 4.75 (t, J=4.99 Hz, 1H), 4.60 (dd, J=6.65, 14.75 Hz, 1H), 3.85 (s, 3H), 3.67-3.77 (m, 1H), 3.58-3.63 (m, 1H), 3.34-3.44 (m, 1H), 2.45 (s, 3H), 1.95-2.07 (m, 1H), 1.71-1.82 (m, 1H). m/z (ESI) 426 [M+H]⁺.

Example 18

Synthesis of 2-(8-(6-aminopyridin-3-yl)-6-(4-cyanophenyl)-1-methyl-5,6-dihydro-4H-benzo[b]isoxazolo[4,5-d]azepin-4-yl)-N,N-dimethylacetamide (139)

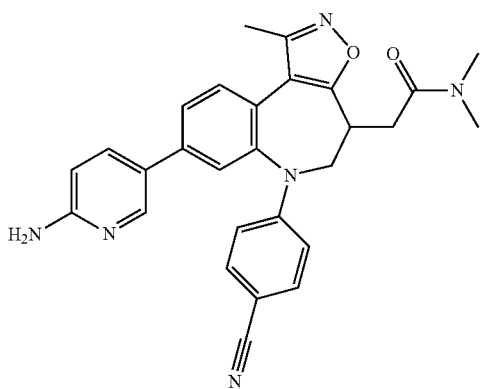 [SMILES: Cc1noc2c1-c1ccc(-c3ccc(N)nc3)cc1N(c1ccc(C#N)cc1)CC2CC(=O)N(C)C]

To a round bottomed flask was added a 1:1 mixture of 4-(8-(6-aminopyridin-3-yl)-4-(2-tert-butoxyethyl)-1-methyl-4H-benzo[b]isoxazolo[4,5-d]azepin-6(5H)-yl)benzonitrile and tert-butyl 2-(8-(6-aminopyridin-3-yl)-6-(4-cyanophenyl)-1-methyl-5,6-dihydro-4H-benzo[b]isoxazolo[4,5-d]azepin-4-yl)acetate (115 mg, 0.227 mmol), CH₂Cl₂ (5 ml), and TFA (1 mL, 12.98 mmol). The solution was stirred at room temperature for 2 h before concentrating and placing on a high vacuum line. The crude reside was purified via biotage to afford the carboxylic acid. To this material was added Et₃N (0.221 mL, 1.586 mmol), dimethylamine hydrochloride (107 mg, 1.312 mmol), DMF, and COMU (165 mg, 0.385 mmol). The solution was stirred at room temperature for 3 h. To this solution was added additional Et₃N (0.221 mL, 1.586 mmol) and COMU (165 mg, 0.385 mmol). The solution was stirred over 2 days before being diluted with water and EtOAc. The layers were separated and the aqueous phase was extracted with EtOAc. The combined organics layer was washed with brine, dried over Na₂SO₄, filtered, and concentrated. The crude residue was purified via Biotage to afford impure material. The residue was then purified via RPHPLC to afford 2-(8-(6-aminopyridin-3-yl)-6-(4-cyanophenyl)-1-methyl-5,6-dihydro-4H-benzo[b]isoxazolo[4,5-d]azepin-4-yl)-N,N-dimethylacetamide. m/z (ESI) 479 [M+H]⁺.

Example 19

Synthesis of 4-(4-(cyanomethyl)-1-methyl-8-(1-methyl-1H-pyrazol-4-yl)-4H-benzo[b]isoxazolo[4,5-d]azepin-6(5H)-yl)benzonitrile (140)

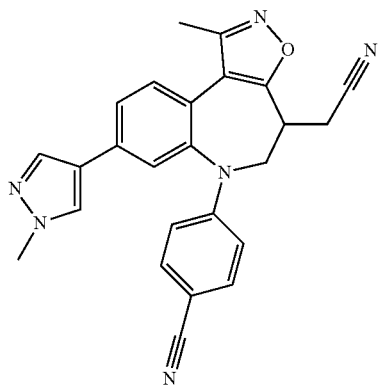 [SMILES: Cc1noc2c1-c1ccc(-c3cnn(C)c3)cc1N(c1ccc(C#N)cc1)CC2CC#N]

To a round bottomed flask was added 2-(6-(4-cyanophenyl)-1-methyl-8-(1-methyl-1H-pyrazol-4-yl)-5,6-dihydro-4H-benzo[b]isoxazolo[4,5-d]azepin-4-yl)acetamide (22 mg, 0.050 mmol), N,N-diisopropylethylamine (0.1 mL, 0.573 mmol), CH₂Cl₂ (1 mL), and TFAA (0.014 mL, 0.100 mmol). The solution was stirred at room temperature overnight before diluting with CH₂Cl₂ and sat. aq. NaHCO₃. The layers were separated and the aqueous phase was extracted with CH₂Cl₂. The combined organics layer was dried over Na₂SO₄, filtered, and concentrated. The crude residue was purified via RP-HPLC to afford 4-(4-(cyanomethyl)-1-methyl-8-(1-methyl-1H-pyrazol-4-yl)-4H-benzo[b]isoxazolo[4,5-d]azepin-6(5H)-yl)benzonitrile (3 mg, 7.13 μmol, 14% yield). ¹H NMR (400 MHz, DMSO-d6) δ 8.24 (s, 1H), 7.94 (s, 1H), 7.85 (d, J=8.10 Hz, 1H), 7.67 (dd, J=1.87, 8.31 Hz, 1H), 7.62 (d, J=1.66 Hz, 1H), 7.58 (d, J=8.93 Hz, 2H), 6.91 (d, J=7.69 Hz, 2H), 4.66 (dd, J=5.82, 9.56 Hz, 1H), 4.00-3.90 (m, 1H), 3.85 (s, 3H), 3.44-3.33 (m, 1H), 3.18 (dd, J=5.40, 17.24 Hz, 1H), 3.09 (dd, J=5.40, 17.45 Hz, 1H), 2.50 (s, 3H). m/z (ESI) 421 [M+H]⁺.

Example 20

Synthesis of 4-(1,5-dimethyl-4H-benzo[b]isoxazolo[4,5-d]azepin-6(5H)-yl)benzonitrile (141)

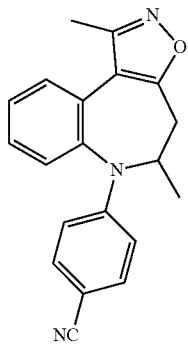 [SMILES: Cc1noc2c1-c1ccccc1N(c1ccc(C#N)cc1)C(C)C2]

Step 1: Synthesis of N-methoxy-N-methyl-2-(3-methylisoxazol-5-yl)acetamide

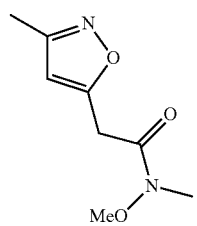

A round bottomed flask was charged with 2-(3-methylisoxazol-5-yl)acetic acid (2 g, 14.17 mmol) and a stirbar. Dichloromethane (50 mL, 0.3 M) was added, followed by CDI (2.76 g, 17.01 mmol), portionwise. Stirred at room temperature 1 h. O,N-dimethylhydroxylamine hydrochloride (1.797 g, 18.42 mmol) was added, and the reaction stirred at room temperature 2.5 d. The reaction was quenched with NH$_4$Cl (aq., sat.) and the product was extracted with ethyl acetate. The organic layer was dried with sodium sulfate and purified by silica gel chromatography (eluting with hexanes/ethyl acetate) to yield N-methoxy-N-methyl-2-(3-methylisoxazol-5-yl)acetamide (1.64 g, 8.89 mmol) as a colorless oil that was used in the subsequent reaction. LC/MS: 185 [M+1].

Step 2: Synthesis of 1-(3-methylisoxazol-5-yl)propan-2-one

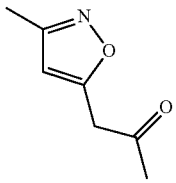

A round bottomed flask was charged with N-methoxy-N-methyl-2-(3-methylisoxazol-5-yl)acetamide (1.637 g, 8.89 mmol) and a stirbar before being purged with N$_2$. THF (100 mL, 0.1 M) was added, and the solution was cooled to −78° C. for the dropwise addition of methylmagnesium bromide (7.62 ml, 10.66 mmol). The solution was stirred at −78° C. 1 h before being quenched into NH$_4$Cl and extracted with ethyl acetate. The aqueous layer was extracted three times with ethyl acetate, and the combined organic layers were washed with brine before being dried with sodium sulfate. The residue was purified by silica gel chromatography (eluting with hexanes/ethyl acetate) to provide 1-(3-methylisoxazol-5-yl)propan-2-one (898 mg, 6.45 mmol) as a light yellow oil that was used in the subsequent reaction. LC/MS: 140 [M+1].

Step 3: Synthesis of 2-bromo-N-(1-(3-methylisoxazol-5-yl)propan-2-yl)aniline

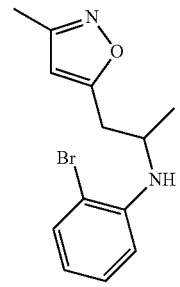 [SMILES: Cc1cc(CC(C)Nc2ccccc2Br)on1]

A round bottomed flask was charged with 1-(3-methylisoxazol-5-yl)propan-2-one (898 mg, 6.45 mmol) and a stirbar before the addition of methanol (65 mL, 0.1 M). 2-bromoaniline (2220 mg, 12.91 mmol) and acetic acid (1108 µl, 19.36 mmol) were added, and the solution was stirred at room temperature 15 min before the addition of sodium cyanoborohydride (608 mg, 9.68 mmol). The mixture was stirred at room temperature overnight before being concentrated with Celite and purified by silica gel chromatography (eluting with hexanes/ethayl acetate) to yield 2-bromo-N-(1-(3-methylisoxazol-5-yl)propan-2-yl)aniline (378 mg, 1.281 mmol) as a brownish oil that was used in the subsequent reaction. LC/MS: 296 [M+1].

Step 4: Synthesis of 1,5-dimethyl-5,6-dihydro-4H-benzo[b]isoxazolo[4,5-d]azepine (144)

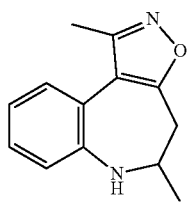

144

A disposable tube was charged with palladium (II) chloride (11.35 mg, 0.064 mmol), potassium acetate (251 mg, 2.56 mmol), tetrabutylammonium chloride (356 mg, 1.281 mmol), and a stirbar before being evac/purged with nitrogen. 2-bromo-N-(1-(3-methylisoxazol-5-yl)propan-2-yl)aniline (378 mg, 1.281 mmol) was added, followed by dimethylacetamide (6 mL, 0.2 M), and the mixture was stirred at 130° C. 2 h before being diluted with ethyl acetate, washed three times with brine, dried with sodium sulfate, and purified by silica gel chromatography (eluting with hexanes/ethyl acetate) to yield 1,5-dimethyl-5,6-dihydro-4H-benzo[b]isoxazolo[4,5-d]azepine (yield not determined) as an off-white amorphous solid that was used in the subsequent reaction. LC/MS: 215 [M+1].

Step 5: Synthesis of 4-(1,5-dimethyl-4H-benzo[b]isoxazolo[4,5-d]azepin-6(5H)-yl)benzonitrile

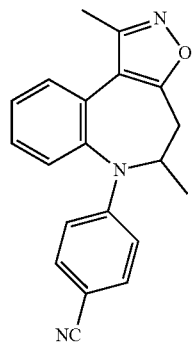 [SMILES: Cc1noc2c1-c1ccccc1N(c1ccc(C#N)cc1)C(C)C2]

A disposable tube was charged with 1,5-dimethyl-5,6-dihydro-4H-benzo[b]isoxazolo[4,5-d]azepine (50 mg, 0.233 mmol), 4-chlorobenzonitrile (48.2 mg, 0.350 mmol), RuPhos precatalyst (8.50 mg, 0.012 mmol), RuPhos (5.44 mg, 0.012 mmol), sodium tertbutoxide (33.6 mg, 0.350 mmol), and a stirbar before being evac/purged three times with nitrogen. Toluene (2 mL, 0.1 M) was added, and the mixture was stirred at 90° C. for 3.5 h. The mixture was diluted with ethyl acetate, filtered, purified by silica gel chromatography, and lyophilized from dioxane to yield 4-(1,5-dimethyl-4H-benzo[b]isoxazolo[4,5-d]azepin-6(5H)-yl)benzonitrile as a white amorphous solid. LC/MS: 316 [M+1]. $^1$H NMR (400 MHz, DMSO-$d_6$) δ 7.87-7.77 (m, 1H), 7.54-7.41 (m, 3H), 7.32 (d, J=7.55 Hz, 1H), 6.74 (d, J=8.24 Hz, 2H), 4.95 (t, J=6.64 Hz, 1H), 3.61-3.51 (m, 1H), 3.10 (d, J=18.31 Hz, 1H), 2.46 (s, 3H), 0.94 (d, J=6.87 Hz, 3H).

Example 21

Synthesis of 4-amino-1-methyl-4H-benzo[b]isoxazolo[4,5-d]azepin-5(6H)-one (142)

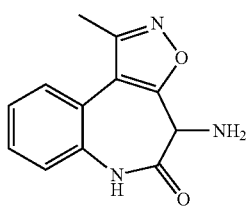 [SMILES: Cc1noc2c1-c1ccccc1NC(=O)C2N]

Step 1: Synthesis of (4-bromo-3-methylisoxazol-5-yl)methyl acetate

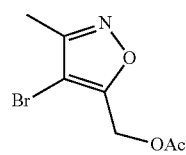

To a solution of (3-methylisoxazol-5-yl)methyl acetate (0.979 g, 6.31 mmol) in AcOH (10 mL, 175 mmol) was added N-bromosuccinimide (1.30 g, 7.30 mmol) and $H_2SO_4$ (0.65 mL, 12.19 mmol). The reaction was heated to 110° C. After 1 h, the reaction mixture was cooled to room temperature and carefully poured into a beaker containing ice and saturated $NaHCO_3$. The bi-phasic mixture was vigorously stirred and basic solution (pH~8-9) was extracted with EtOAc (2×15 mL). The organic layer was washed with 2% sodium thiosulfate, washed with brine (20 mL), dried over $Na_2SO_4$, and concentrated to give a light yellow oil. The oil was purified on Biotage system (isocratic elution 10% EtOAc: 90% Hexanes) to give the titled compound (1.30 g, 5.55 mmol, 88% Yield) as a colorless yellow oil. LC/MS m/z 234 [M+H]$^+$.

Step 2: Synthesis of (3-methyl-4-(4,4,5,5-tetramethyl-1,3,2-dioxaborolan-2-yl)isoxazol-5-yl)methyl acetate

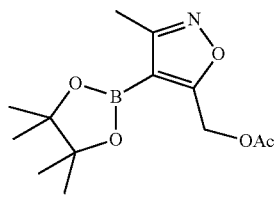 [SMILES: CC(=O)OCc1onc(C)c1B1OC(C)(C)C(C)(C)O1]

A disposable tube was charged with $PdCl_2(CH_3CN)_2$ (0.113 g, 0.437 mmol), SPhos (0.717 g, 1.747 mmol), and a stirbar before being evacuated and purged with nitrogen. (4-bromo-3-methylisoxazol-5-yl)methyl acetate (5.11 g, 21.83 mmol), 4,4,5,5-tetramethyl-1,3,2-dioxaborolane (4.75 ml, 32.7 mmol), and dioxane (10 mL) were added, followed by triethylamine (9.13 ml, 65.5 mmol) (gas evolution!), and the mixture was stirred at 110° C. overnight. The mixture was cooled, diluted with ethyl acetate, filtered, and concentrated to give a residue that was used crude in the subsequent reaction.

Step 3: Synthesis of tert-butyl (2-(5-(hydroxymethyl)-3-methylisoxazol-4-yl)phenyl)carbamate

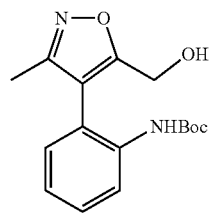

A disposable tube was charged with Pd(Ph$_3$P)$_4$ (0.841 g, 0.728 mmol), potassium phosphate (6.18 g, 29.1 mmol), (3-methyl-4-(4,4,5,5-tetramethyl-1,3,2-dioxaborolan-2-yl)isoxazol-5-yl)methyl acetate (6.14 g, 21.83 mmol) (crude), and a stirbar before being evacuated and purged with nitrogen three times.tert-butyl 2-bromophenylcarbamate (2.95 ml, 14.55 mmol) was added, followed by methanol (10 mL, 2 M), and the reaction was stirred at 70° C. 3 h. The mixture was cooled, diluted with ethyl acetate, filtered, washed three times with brine, dried with magnesium sulfate, and purified by silica gel chromatography (eluting with hexanes/ethyl acetate) to yield tert-butyl (2-(5-(hydroxymethyl)-3-methylisoxazol-4-yl)phenyl)carbamate as a yellow oil. LC/MS: 305 [M+1].

Step 4: Synthesis of tert-butyl (2-(5-formyl-3-methylisoxazol-4-yl)phenyl)carbamate

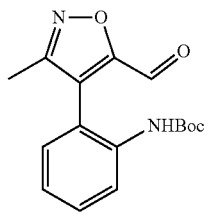 [SMILES: Cc1noc(C=O)c1-c1ccccc1NC(=O)OC(C)(C)C]

A round bottomed flask was charged with dichloromethane (50 mL) and oxalyl chloride (1.474 ml, 16.84 mmol), and the solution was cooled to −78° C. for the dropwise addition of DMSO (1.594 ml, 22.46 mmol) in dichloromethane (50 mL). The solution was stirred at −78° C. for 15 min before the dropwise addition of tert-butyl 2-(5-(hydroxymethyl)-3-methylisoxazol-4-yl)phenylcarbamate (3.417 g, 11.23 mmol) in dichloromethane (50 mL). The mixture was stirred at −78° C. 15 min before the dropwise addition of triethylamine (4.69 ml, 33.7 mmol) before being warmed to room temperature. The mixture was diluted with water, separated, the aqueous layer was extracted with dichloromethane, and the combined organic washes were dried with magnesium sulfate. The residue was purified by silica gel chromatography (eluting with hexanes/ethyl acetate) to yield tert-butyl (2-(5-formyl-3-methylisoxazol-4-yl)phenyl)carbamate (1.4 g, 4.64 mmol) as a solid. LC/MS: 303.

Step 5: Synthesis of (E)-tert-butyl (2-(5-((benzhydrylimino)methyl)-3-methylisoxazol-4-yl)phenyl)carbamate

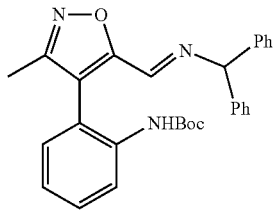 [SMILES: Cc1noc(/C=N/C(c2ccccc2)c2ccccc2)c1-c1ccccc1NC(=O)OC(C)(C)C]

A round bottomed flask was charged with tert-butyl 2-(5-formyl-3-methylisoxazol-4-yl)phenyl)carbamate (1.4 g, 4.63 mmol) and a stirbar. Dichloromethane (50 mL, 0.1 M) was added, followed by diphenylmethanamine (3.19 ml, 18.52 mmol) and sodium sulfate (6.58 g, 46.3 mmol), and the mixture was stirred at room temperature 3 d. The mixture was filtered, concentrated with Celite, and purified by silica gel chromatography (eluting with hexanes/ethyl acetate) to provide (E)-tert-butyl (2-(5-((benzhydrylimino)methyl)-3-methylisoxazol-4-yl)phenyl)carbamate (0.98 g, 2.1 mmol) as a white amorphous solid.

Step 6: Synthesis of (2-(5-((benzhydrylamino)(cyano)methyl)-3-methylisoxazol-4-yl)phenyl)carbamate

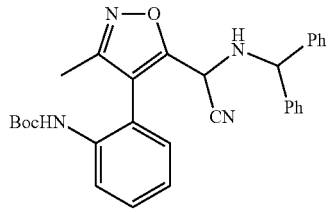 [SMILES: Cc1noc(C(C#N)NC(c2ccccc2)c2ccccc2)c1-c1ccccc1NC(=O)OC(C)(C)C]

A disposable tube was charged with (E)-tert-butyl 2-(5-((benzhydrylimino)methyl)-3-methylisoxazol-4-yl)phenyl)carbamate (52.5 mg, 0.112 mmol), Ytterbium(III)trifluoromethanesulfonate (6.96 mg, 0.011 mmol), and a stirbar. Dichloromethane (2 mL, 0.05 M) was added, followed by trimethylsilanecarbonitrile (28.1 µl, 0.225 mmol), and the solution was stirred at room temperature overnight. The reaction was washed with sodium bicarbonate (aq., sat.), dried with magnesium sulfate, concentrated with Celite, purified by silica gel chromatography (eluting with hexanes/ethyl acetate/1% isopropanol), and lyophilized to yield tert-butyl (2-(5-((benzhydrylamino)(cyano)methyl)-3-methylisoxazol-4-yl)phenyl)carbamate (25 mg, 0.05 mmol) as a white amorphous solid. LC/MS: 490/495.

Step 7: Synthesis of 4-amino-1-methyl-4H-benzo[b]isoxazolo[4,5-d]azepin-5(6H)-one

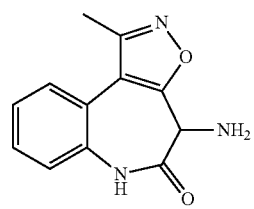 [SMILES: Cc1noc2c1-c1ccccc1NC(=O)C2N]

A disposable tube was charged with tert-butyl 2-(5-((benzhydrylamino)(cyano)methyl)-3-methylisoxazol-4-yl)phenyl)carbamate (159 mg, 0.321 mmol) and a stirbar. Concentrated sulfuric acid (1 mL, 18.76 mmol) was added, and the solution was stirred at 90° C. for 1 h, at which point the mixture was cooled and quenched dropwise into ice water. The pH was brought to ~8 with a 50% NaOH (aq.) solution. The product was extracted three times, purified by silica gel chromatography (eluting with dichloromethane/methanol/ 1% ammonium hydroxide), and lyophlized to yield 4-amino-1-methyl-4H-benzo[b]isoxazolo[4,5-d]azepin-5 (6H)-one (33 mg, 0.144 mmol) as a yellow amorphous solid. LC/MS: [M+1]. $^1$H NMR (400 MHz, DMSO-$d_6$) 11.06 (s, 1H), 9.28 (br. s., 2H), 7.73 (dd, J=1.25, 7.89 Hz, 1H), 7.45-7.52 (m, 1H), 7.30-7.42 (m, 2H), 5.43 (s, 1H), 2.51 (s, 3H).
LC/MS: 230 [M+1].

Example 22

IC50 Measurements for Inhibitors Using BRD4 AlphaLisa Binding Assay

His/Flag epitope tagged BRD4 BD1$_{42-168}$ was cloned, expressed and purified to homogeneity. BRD4 binding and inhibition was assessed by monitoring the engagement of biotinylated H4-tetraacetyl peptide (Millipore #12-379) with the target using the AlphaLisa technology (Perkin-Elmer). Specifically, in a 384 well ProxiPlate BRD4(BD1) (30 nM final) was combined with peptide (200 nM final) in 40 mM HEPES (pH 7.0), 40 mM NaCl, 1 mM DTT, 0.01% (w/v) BSA, and 0.008% (w/v) Brij-35 either in the presence of DMSO (final 1.2% DMSO) or compound dilution series in DMSO. After 20 minute incubation at room temperature Alpha streptavidin donor beads and AlphaLisa anti-Flag acceptor beads were added to a final concentration of 10 ug/mL each. After three hours equilibration plates were read on an Envision instrument and $IC_{50}$s calculated using a four parameter non-linear curve fit. The results of this assay are set forth in Table 2, below.

Example 23

Cell-Based Assays cMyc RNA Quantification Assay (QuantiGene® Assay):
MV4:11 (AML) or Raji (Burkitt's lymphoma) cells were seeded in a 96-well plate and incubated in the presence of various concentrations of compounds for 4 h. Relative mRNA levels were quantitated by using QuantiGene 2.0 assay (Affymetrix) according to the manufacturer's recommendation. Signals were detected by using an Envision plate reader (Perkin-Elmer). Biological duplicates were averaged and normalized to vehicle (DMSO) control to calculate percent MYC mRNA levels.

Cell-Based IL-6 Quantification Assay (ELISA, Mesoscale Assay):
100,000 THP-1 cells were seeded in RPMI1640-10% FBS in 96-well plates. LPS (E. Coli Invitrogen) in RPMI-10% FBS at a final concentration of 4 µg/mL was added to the wells and the cells are then incubated in the presence of various concentrations of compounds for 16 h. Plates are spun (2 rpm, 5 min), an aliquot of 25 uL supernatant is transferred in to an ELISA plate (Mesoscale technology, MSD) and the detection of IL-6 is performed using manufacturer's instructions. The amount of cells in each well is assessed using CellTiter-Glo® (Promega). The ratio of ELISA value/CellTiter-Glo value is used to calculate the percent of inhibition of IL-6 secretion. The result of these assays for certain compounds of the invention are set forth in Table 1 below.

TABLE 1

Activity for exemplified compounds

| Cmpd No. | AS $IC_{50}$ (µM) | IL-6 $IC_{50}$ (µM) | MYC $EC_{50}$ (µM) |
|---|---|---|---|
| 142 | >80 | >1 | n.t. |
| 143 | 39.6 | n.t. | n.t. |
| 144 | 24 | >15 | n.t. |
| 100 | 29.8 | >15 | n.t. |
| 101 | 2.68 | 11.9 | n.t. |
| 102 | 0.43 | 4.57 | n.t. |
| 132 | 8.14 | 3.11 | n.t. |
| 103 | 0.50 | 3.18 | n.t. |
| 127 | 9.87 | >15.0 | n.t. |
| 128 | 8.10 | >15.0 | n.t. |
| 129 | 7.90 | >15.0 | n.t. |
| 107 | >4.0 | >15.0 | n.t. |
| 141 | 0.56 | 4.39 | n.t. |
| 130 | 12.9 | 5.9 | >4.0 |
| 131 | 20.7 | 8.5 | >4.0 |
| 116 | 0.06 | 0.38 | 0.55 |
| 115 | 0.03 | 0.53 | 2.12 |

TABLE 1-continued

Activity for exemplified compounds

| Cmpd No. | AS $IC_{50}$ (µM) | IL-6 $IC_{50}$ (µM) | MYC $EC_{50}$ (µM) |
|---|---|---|---|
| 114 | 3.8 | >15 | >4.0 |
| 113 | 8.9 | 7.4 | >4.0 |
| 106 | 0.23 | >1.0 | 1.98 |
| 136 | 4.77 | 7.70 | >4.0 |
| 112 | 50.0 | >15.0 | n.t. |
| 104 | 0.75 | n.t. | n.t. |
| 105 | 3.38 | n.t. | n.t. |
| 108 | 0.57 | n.t. | n.t. |
| 126 | 1.41 | 5.28 | 1.79 |
| 111 | 0.30 | >1.0 | 3.33 |
| 110 | 0.08 | >1.0 | 0.78 |
| 109 | 0.35 | >1.0 | 2.04 |
| 119 | 0.15 | 0.61 | 0.46 |
| 117 | 0.04 | 0.15 | 0.61 |
| 120 | 0.24 | >1.0 | 1.46 |
| 122 | 0.04 | 0.12 | 0.24 |
| 121 | 0.08 | 0.15 | 0.46 |
| 125 | 0.04 | 0.09 | 0.17 |
| 124 | 0.04 | 0.12 | 0.26 |
| 123 | 0.04 | 0.08 | 0.20 |
| 134 | 0.03 | 0.07 | 0.12 |
| 133 | >4 | >1.0 | >4.0 |
| 137 | 0.42 | >1.0 | 1.84 |
| 138 | 0.08 | 0.34 | 0.31 |
| 118 | 0.16 | 0.52 | 0.83 |
| 139 | 1.0 | >1.0 | >4.0 |
| 140 | 0.5 | >1.0 | n.t. |
| 135 | 0.49 | 0.65 | 1.32 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

We claim:

1. A compound of Formula (Ia) or (Ib):

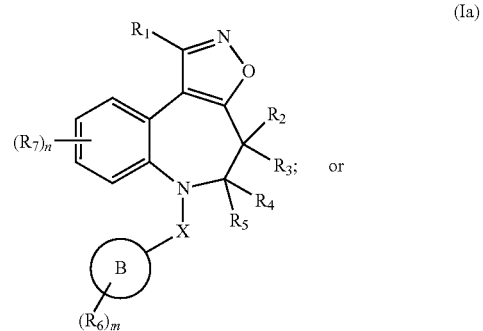

-continued (Ib)

[Chemical structure showing a tricyclic system with R1, R2, R3, R4, R5, (R7)n, (R6)m, X, and ring B]

or a pharmaceutically acceptable salt thereof, wherein:

Ring B is a 3-7 membered saturated or partially unsaturated carbocyclic ring, phenyl, an 8-10 membered bicyclic saturated or partially unsaturated carbocyclic ring, a 4-7 membered saturated or partially unsaturated heterocyclic ring having 1-2 heteroatoms independently selected from nitrogen, oxygen, and sulfur, a 5-6 membered monocyclic heteroaryl ring having 1-3 heteroatoms independently selected from nitrogen, oxygen, and sulfur, a 7-10 membered bicyclic saturated or partially unsaturated heterocyclic ring having 1-4 heteroatoms independently selected from nitrogen, oxygen, and sulfur, or an 8-10 membered bicyclic heteroaryl ring having 1-4 heteroatoms independently selected from nitrogen, oxygen, and sulfur;

$R_1$ is hydrogen or $C_{1-6}$ aliphatic;

$R_2$ and $R_4$ are each independently hydrogen, $(C_1-C_6)$alkyl, $(C_1-C_6)$haloalkyl, $(C_1-C_6)$alkoxy, $(C_1-C_6)$haloalkoxy, —N(R')$_2$, -halogen, —CN, —SR, —OH, or —(CH$_2$)$_b$R$^x$;

$R_3$ and $R_5$ are each independently hydrogen or $(C_1-C_6)$alkyl; or each of $R_2$ and $R_3$ or $R_4$ and $R_5$ are taken together with their intervening atoms to form CO or an optionally substituted 3-7 membered cycloalkyl;

X is CO, a covalent bond, or $(C_1-C_3)$alkyl;

each R and R' are independently hydrogen, $(C_1-C_3)$alkyl, halogen, $(C_1-C_3)$haloalkyl, $(C_1-C_3)$alkoxy, $(C_1-C_3)$haloalkoxy, or phenyl optionally substituted with one or more halogen, $(C_1-C_6)$alkyl, $(C_1-C_6)$haloalkyl, $(C_1-C_6)$alkoxy, $(C_1-C_6)$haloalkoxy, —CN, —C(O)R", or —CO$_2$R";

each R" is independently hydrogen, $(C_1-C_3)$alkyl, halogen, $(C_1-C_3)$haloalkyl, $(C_1-C_3)$alkoxy, $(C_1-C_3)$haloalkoxy, or phenyl optionally substituted with one or more halogen, $(C_1-C_6)$alkyl, $(C_1-C_6)$haloalkyl, $(C_1-C_6)$alkoxy, $(C_1-C_6)$haloalkoxy, or —CN $R^x$ is halogen, $(C_1-C_6)$alkoxy, $(C_1-C_6)$haloalkoxy, —OR, —SR, —CN, —N(R')$_2$, —C(O)R, —CO$_2$R, —C(O)N(R')$_2$, —C(O)C(O)R, —C(O)CH$_2$C(O)R, —N(R')C(O)R, —N(R')C(O)N(R')$_2$, —OC(O)R, or —OC(O)N(R')$_2$;

b is 0-3;

each of m and n is independently 0-4, as valency permits; and each of $R_6$ and $R_7$ are independently optionally substituted phenyl, halogen, $(C_1-C_3)$alkyl, $(C_1-C_3)$haloalkyl, $(C_1-C_3)$alkoxy, $(C_1-C_3)$haloalkoxy, —OR, —SR, —N(R')$_2$, —CN, —NO$_2$, —C(O)R, —C(S)R, —CO$_2$R, —C(O)N(R')$_2$, —C(O)SR, —C(O)C(O)R, —C(O)CH$_2$C(O)R, —C(S)N(R')$_2$, —C(S)OR, —S(O)R, —SO$_2$R, —SO$_2$N(R')$_2$, —N(R')C(O)R, —N(R')C(O)N(R')$_2$, —N(R')C(S)N(R')$_2$, —N(R')SO$_2$R, —N(R')SO$_2$N(R')$_2$, —N(R')N(R')$_2$, —N(R')C(=N(R'))N(R')$_2$, —C=NN(R')$_2$, —C=NOR, —C(=N(R'))N(R')$_2$, —OC(O)R, or —OC(O)N(R')$_2$.

2. The compound of claim 1, wherein the compound is of Formula (II):

(II)

[Chemical structure]

or a pharmaceutically acceptable salt thereof.

3. The compound of claim 2, wherein the compound is of Formula (VIII) or (IX):

(VIII)

[Chemical structure]

(IX)

[Chemical structure]

or a pharmaceutically acceptable salt thereof, wherein $R_2$ is hydrogen, $(C_1-C_3)$alkyl, —N(R')$_2$, (CH$_2$)OH, (CH$_2$)CN, or (CH$_2$)CON(R')$_2$;

$R_3$ is hydrogen; or $R_2$ and $R_3$ taken together with their intervening atoms to form CO or a 3-7 membered cycloalkyl;

$R_6$ is halogen, —CN, $(C_1-C_3)$alkyl, —C(O)N(R')$_2$, or —SO$_2$R;

$R_7$ is $(C_1-C_3)$alkyl, halogen, $(C_1-C_3)$haloalkyl, $(C_1-C_3)$alkoxy, $(C_1-C_3)$haloalkoxy —C(O)N(R')$_2$, or —CN;

p is 0-2;
R$_8$ is (C$_1$-C$_3$)alkyl, halogen, (C$_1$-C$_3$)haloalkyl, (C$_1$-C$_3$)alkoxy, (C$_1$-C$_3$)haloalkoxy, —CN, —(CH$_2$)NH$_2$, (CH$_2$)OH, (CH$_2$)CN, (CH$_2$)CON(Me)$_2$, or (CH$_2$)CONH$_2$; and
each R and R' are independently hydrogen or (C$_1$-C$_3$)alkyl.
4. A compound selected from the formula:
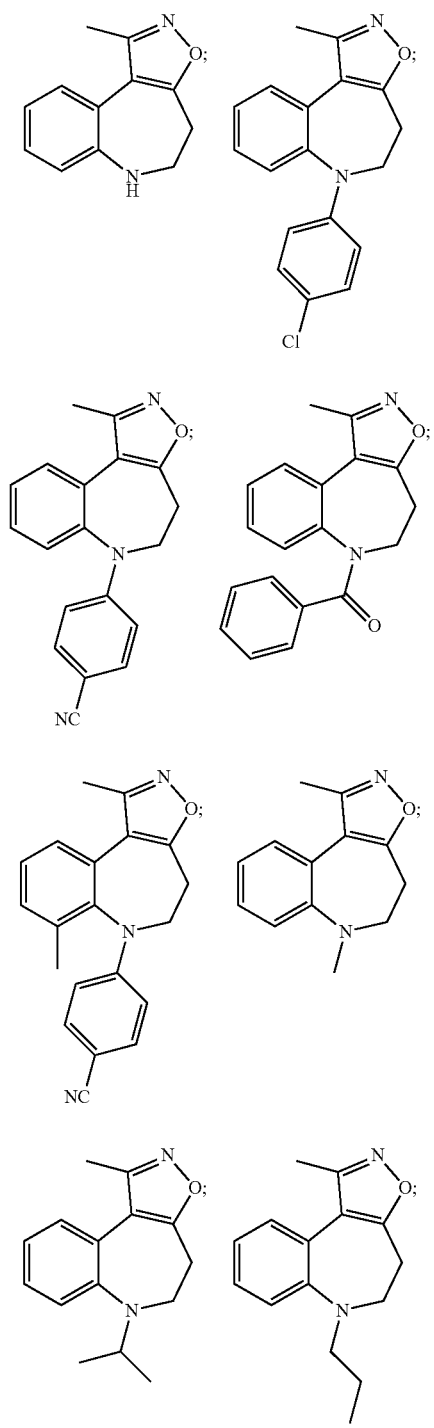
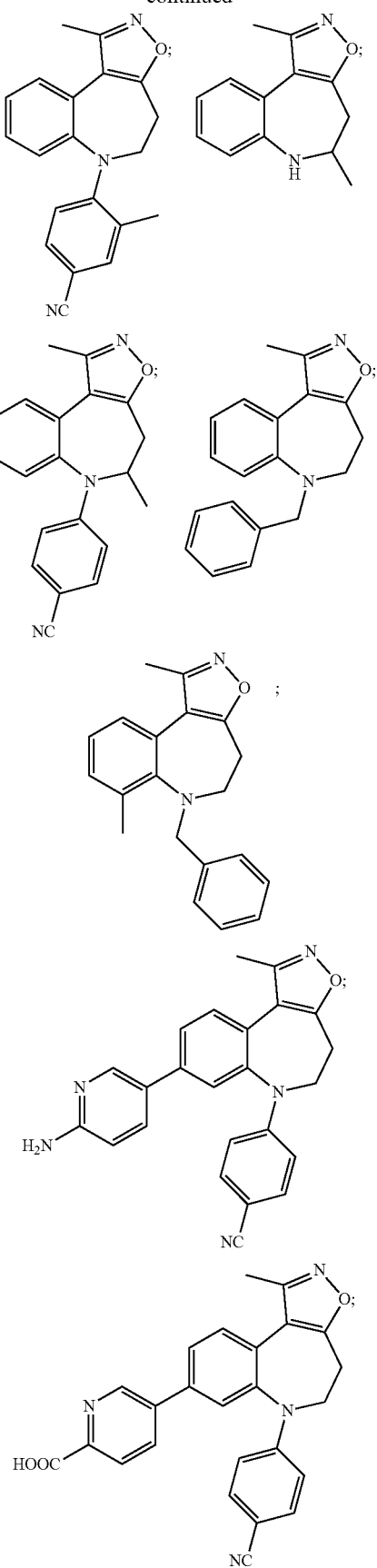

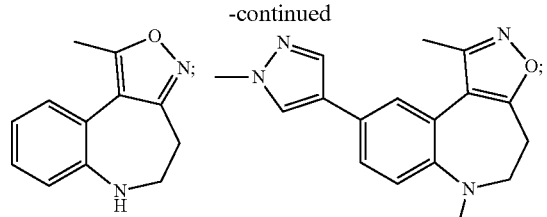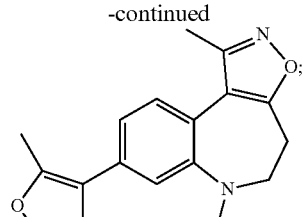
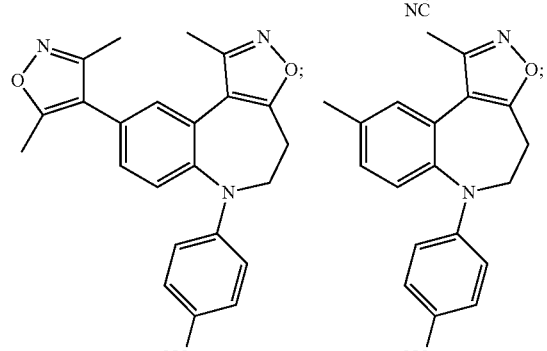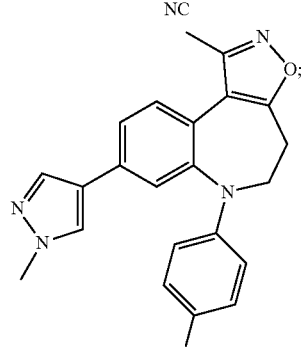
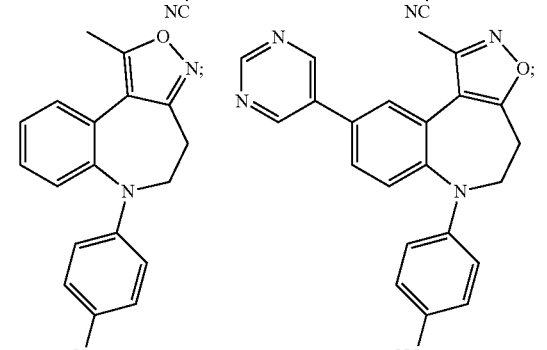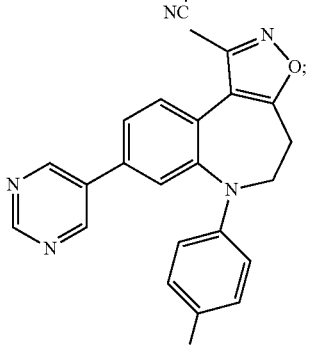
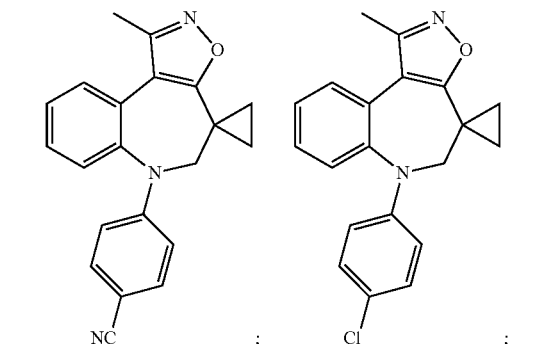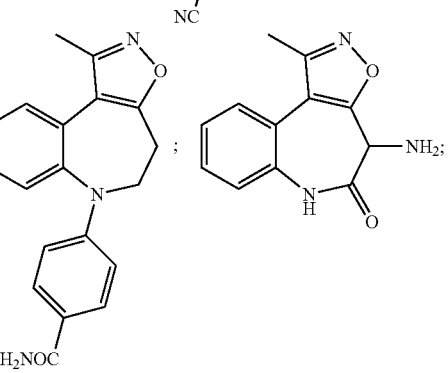
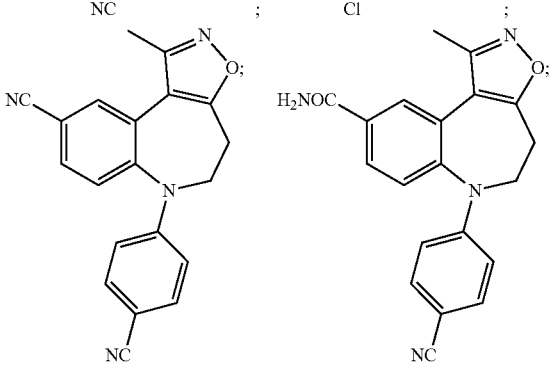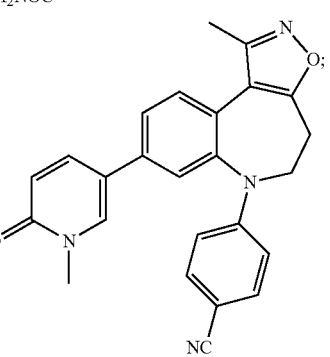

91
-continued
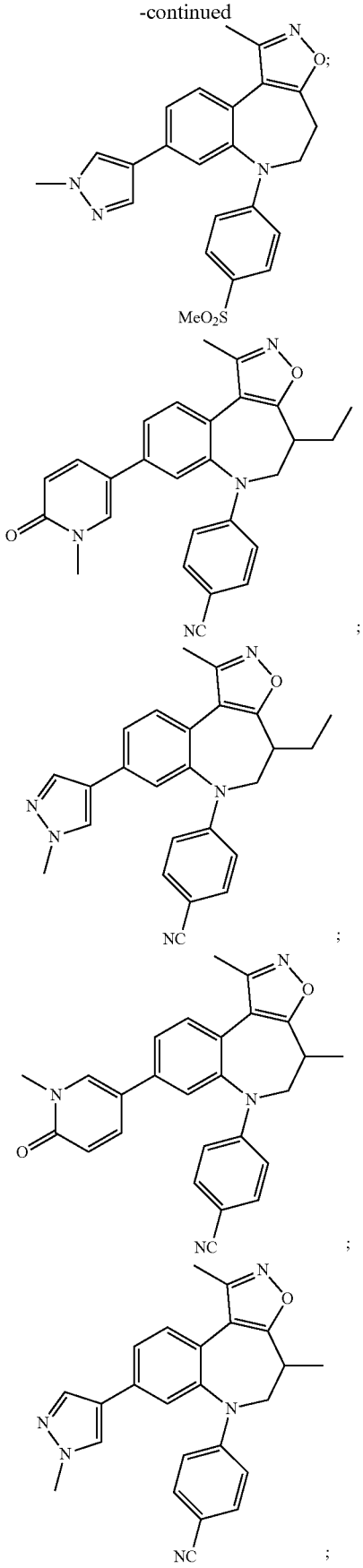
92
-continued
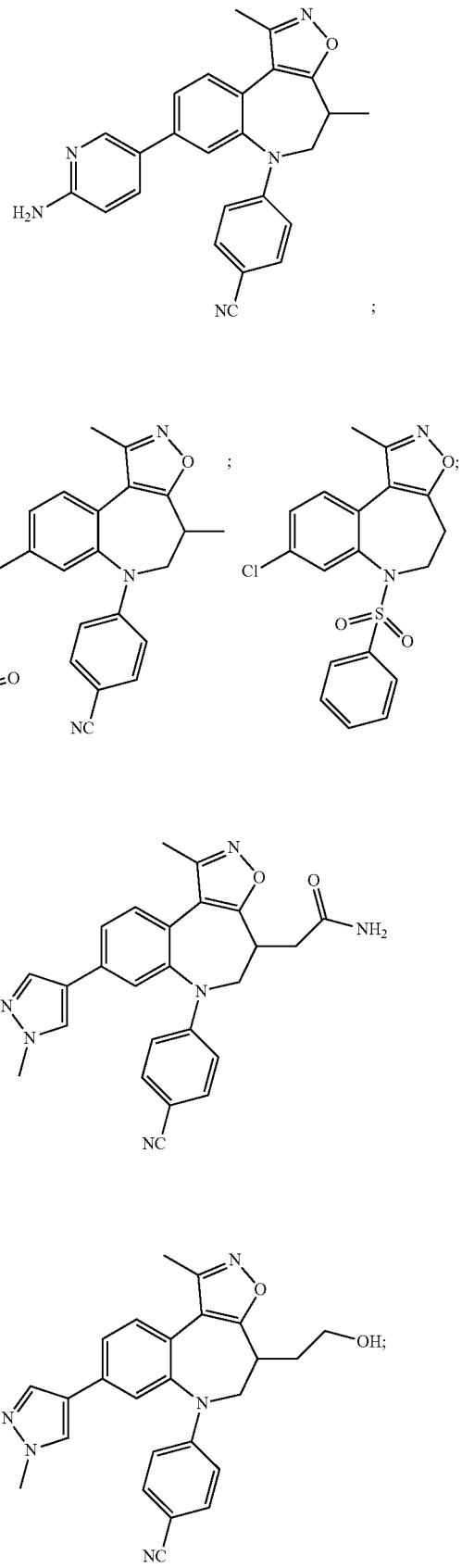

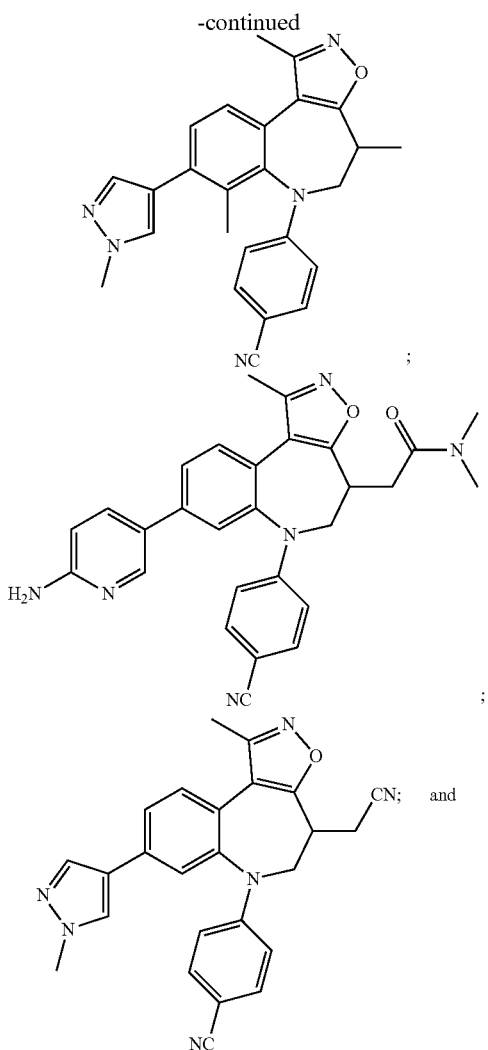

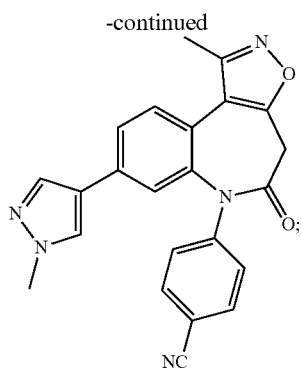

or a pharmaceutically acceptable salt thereof.

5. A composition comprising a compound according to claim 1 and a pharmaceutically acceptable adjuvant, carrier, or vehicle.

6. A method of treating adenocarcinoma, hematological malignancies, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor in a patient in need thereof, comprising the step of administering to said patient a compound according to claim 1.

* * * * *

UNITED STATES PATENT AND TRADEMARK OFFICE
CERTIFICATE OF CORRECTION

PATENT NO.       : 9,624,244 B2
APPLICATION NO.  : 14/405211
DATED            : April 18, 2017
INVENTOR(S)      : Albrecht et al.

Page 1 of 1

It is certified that error appears in the above-identified patent and that said Letters Patent is hereby corrected as shown below:

Column 88, Claim 4, Lines 53-67, please replace " 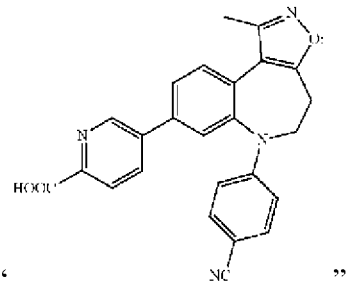 "

with -- 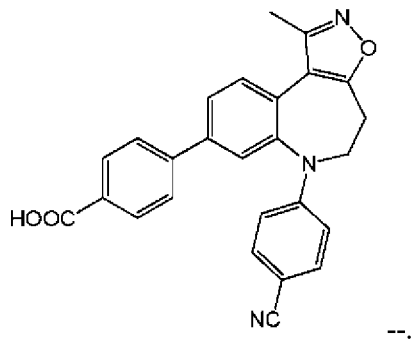 --.

Signed and Sealed this
Twenty-first Day of November, 2017

Joseph Matal
*Performing the Functions and Duties of the
Under Secretary of Commerce for Intellectual Property and
Director of the United States Patent and Trademark Office*